(12) United States Patent
Bagnoli et al.

(10) Patent No.: US 11,426,455 B2
(45) Date of Patent: Aug. 30, 2022

(54) IMMUNOGENIC COMPOSITION COMPRISING STAPHYLOCOCCAL ANTIGENS

(71) Applicant: GLAXOSMITHKLINE BIOLOGICALS SA, Rixensart (BE)

(72) Inventors: Fabio Bagnoli, Siena (IT); Carine Goraj, Wavre (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 69 days.

(21) Appl. No.: 16/968,895

(22) PCT Filed: Feb. 12, 2019

(86) PCT No.: PCT/EP2019/053463
§ 371 (c)(1),
(2) Date: Aug. 11, 2020

(87) PCT Pub. No.: WO2019/158537
PCT Pub. Date: Aug. 22, 2019

(65) Prior Publication Data
US 2021/0023192 A1    Jan. 28, 2021

(30) Foreign Application Priority Data

Feb. 13, 2018 (GB) .................................... 1802339

(51) Int. Cl.
| A61K 39/385 | (2006.01) |
| A61K 39/09 | (2006.01) |
| A61K 39/085 | (2006.01) |
| A61K 45/00 | (2006.01) |
| A61K 47/00 | (2006.01) |
| A61P 31/04 | (2006.01) |
| A61K 39/00 | (2006.01) |

(52) U.S. Cl.
CPC ............ *A61K 39/085* (2013.01); *A61P 31/04* (2018.01); *A61K 2039/55505* (2013.01); *A61K 2039/55577* (2013.01); *A61K 2039/575* (2013.01); *A61K 2039/6031* (2013.01); *A61K 2039/70* (2013.01)

(58) Field of Classification Search
CPC .................................................. A61K 39/085
See application file for complete search history.

(56) References Cited

U.S. PATENT DOCUMENTS

2014/0037650 A1    2/2014   Kim et al.

FOREIGN PATENT DOCUMENTS

| AU | 2015202532 A1 | 6/2015 |
| WO | 2006032472 A2 | 3/2006 |
| WO | 2007071692 A2 | 6/2007 |
| WO | WO 2009/095453 | * 8/2009 |
| WO | 2010151544 A1 | 12/2010 |
| WO | 2011138361 A1 | 11/2011 |
| WO | 2012003474 A2 | 1/2012 |
| WO | 2012034067 A1 | 3/2012 |
| WO | 2012085872 A2 | 6/2012 |
| WO | WO 2013/025834 | * 2/2013 |
| WO | 2015082571 A1 | 6/2015 |
| WO | 2015144653 A1 | 10/2015 |
| WO | WO 2019/121924 | * 6/2019 |
| WO | WO 2019/121926 | * 6/2019 |

OTHER PUBLICATIONS

Houghten et al. (Vaccines, 1986, Edited by Fred Brown: Cold Spring Harbor Laboratory) (Year: 1986).*
Whisstock et al., (Quarterly Reviews of Biophysics 2003, vol. 36 (3): 307-340 (Year: 2003).*
Witkowski et al Biochemistry 38:11643-11650, 1999). (Year: 1999).*
Seffernick et al., (J. Bacteriol. 183(8): 2405-2410, 2001), (Year: 2001).*
Broun et al (Science 282:1315-1317, 1998) (Year: 1998).*
International Search Report and Written Opinion in corresponding International Application No. PCT/EP2019/053463 dated May 10, 2019 (5 pages).
Bagnoli et al., Proceedings of the National Academy of Sciences of the United States of America, 112: 3680-3685 (2015).
Nissen et al., Vaccine, 33: 1846-1854 (2015).

* cited by examiner

*Primary Examiner* — Gary B Nickol
*Assistant Examiner* — Lakia J Jackson-Tongue

(57) ABSTRACT

The invention provides an immunogenic composition comprising staphylococcal antigens, containing protein antigens and conjugates of capsular polysaccharides, n particular Hla, ClfA, SpA and conjugates of capsular polysaccharides. Adjuvanted formulations are also provided. The invention may find use in the prevention and treatment of staphylococcal infections, in particular *S. aureus* infection and disease.

16 Claims, 23 Drawing Sheets

Specification includes a Sequence Listing.

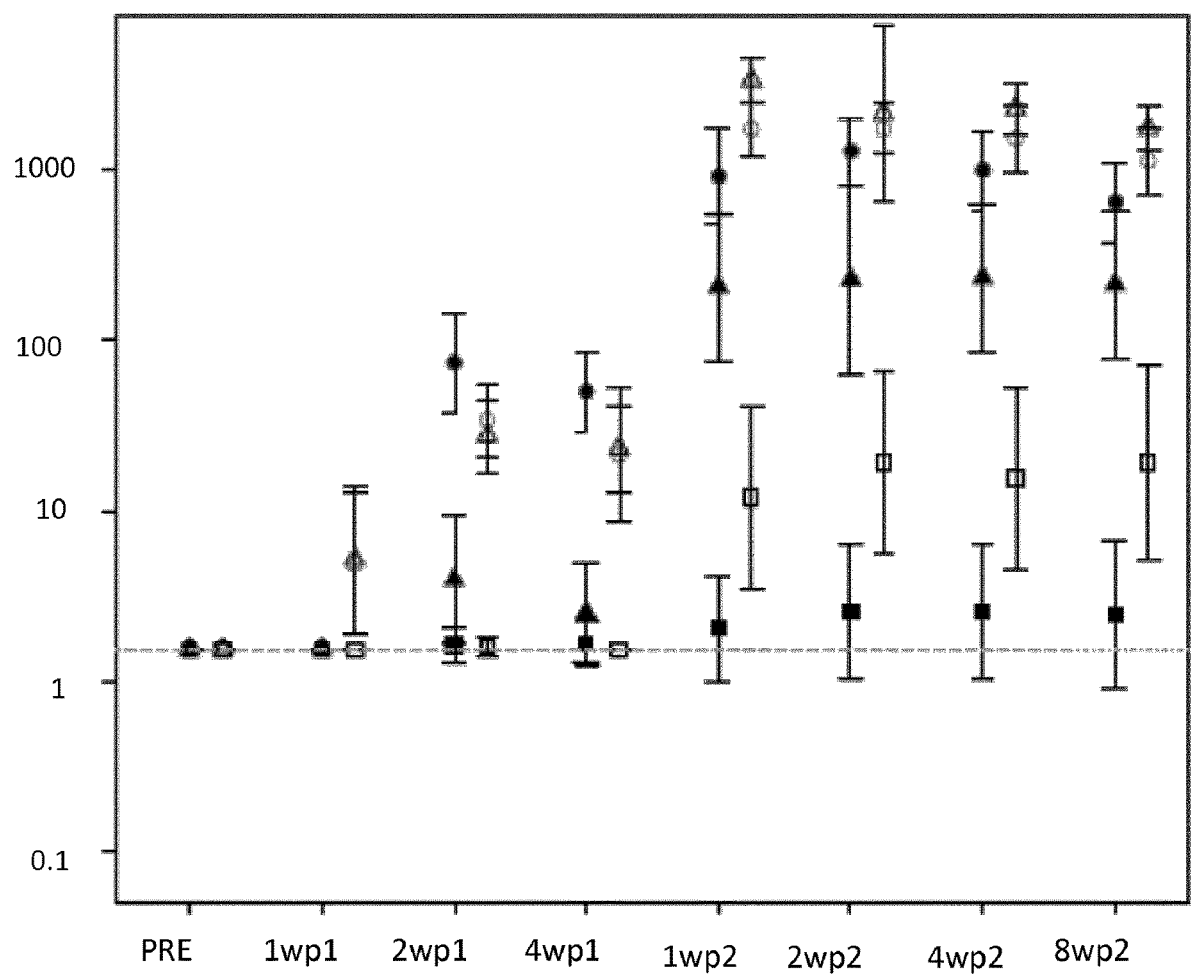

IMMUNOGENIC COMPOSITION COMPRISING STAPHYLOCOCCAL ANTIGENS

FIELD OF THE INVENTION

The invention relates to immunogenic compositions for the prevention and treatment of staphylococcal infection and disease, in particular *S. aureus* infection and disease. The invention provides an immunogenic composition comprising staphylococcal antigens, in particular Hla, ClfA, SpA and conjugates of capsular polysaccharides. Adjuvanted formulations are also provided, as are uses of such compositions in the prevention and treatment of staphylococcal infections.

BACKGROUND TO THE INVENTION

*S. aureus* is a Gram-positive spherical bacterium which is the leading cause of bloodstream, lower respiratory tract, skin & soft tissue infections in the US and Europe. It is also the predominant cause of bone infections worldwide, and these infections are painful, debilitating and difficult to treat.

Treatment of *S. aureus* is becoming increasingly challenging due to the development of antibiotic resistance by many strains of *S. aureus*. Methicillin-resistant *S. aureus* (MRSA) is endemic in hospitals, and community-associated MRSA strains are spreading worldwide, posing a major global challenge. MRSA is found in over half of all community and hospital infections. Recent years have seen the emergence of MRSA strains which are also resistant to vancomycin, the antibiotic of last resort, and which are essentially untreatable.

There is currently no authorised vaccine. The need for a vaccine is particularly acute due to the problem of antibiotic resistance and the fact that *S. aureus* infection does not provide immunity from future infection thanks to its well-developed immune evasion capabilities. The immune evasion properties of *S. aureus* in turn render the development of effective vaccines more difficult. The mechanisms of immune evasion are not fully understood, but are at least in part due to staphylococcal protein A (SpA), an *S. aureus* surface molecule that binds to Fcγ of immunoglobulin (Ig) and to the Fab portion of $V_H3$-type B cell receptors. Interaction of SpA with B cell receptors influences B cell development during infection, interfering with development of the adaptive immune response. SpA binding to Ig Fc interferes with opsonophagocytic clearance of staphylococci by polymorphonuclear leukocytes.

There is thus an urgent need for a vaccine to prevent staphylococcal disease. Several vaccines have been tested in clinical trials, including capsular polysaccharide (CPS) conjugates, individual protein antigens, and monoclonal antibodies (mAbs) to lipoteichoic acid. However, all have failed at various developmental stages, and to date there is no vaccine against *S. aureus* on the market.

A multicomponent vaccine comprising *S. aureus* CPS, ClfA and MntC (Anderson et al 2012, Hum Vaccine Immunother 8: 1585-1594) has been tested in PhI human trials. The vaccine induced opsonic anti-CP antibodies and inhibitory anti-ClfA antibodies in PhI, and was subsequently tested in PhIIb efficacy trials for prophylactic use in elective spinal fusion surgery patients, but the PhIIb trial was stopped for futility.

However, no vaccine against *S. aureus* has yet been found to have protective efficacy in PhIII trials. A vaccine containing conjugates of *S. aureus* Type 5 and Type 8 capsular polysaccharides conjugated to *Pseudomonas* exoprotein A (StaphVAX—Nabi Biopharmaceuticals) has been tested in clinical trials, where it demonstrated safety in PhI and II but failed to achieve the required endpoint in PhIII, as described in WO 03/61558.

Similarly, a vaccine based on the IsdB protein antigen (the V710 vaccine; Kuklin et al, Infect Immun, 2006, 74: 2215-23), failed to meet efficacy endpoints in a PhIII trial conducted in cardiothoracic *S. aureus* infections.

There is thus an ongoing need for an effective vaccine against staphylococcal infection, in particular *S. aureus* infection.

SUMMARY OF THE INVENTION

The present invention provides an immunogenic composition comprising staphylococcal antigens. In one aspect, the immunogenic composition comprises two or more of (a) a ClfA antigen; (b) a Hla antigen; (c) a SpA antigen; and/or (d) a staphylococcal capsular polysaccharide. The ClfA antigen, the Hla antigen and the SpA antigen are preferably staphylococcal antigens, suitably *S. aureus* antigens.

In an embodiment, the immunogenic composition comprises a ClfA antigen; a Hla antigen; a SpA antigen; and a staphylococcal capsular polysaccharide. The capsular polysaccharide may suitably be a *S. aureus* serotype 5 and/or type 8 capsular polysaccharide. In a preferred embodiment, the immunogenic composition comprises a ClfA antigen; a Hla antigen; a SpA antigen; a capsular polysaccharide from *S. aureus* serotype 5 and a capsular polysaccharide from *S. aureus* serotype 8.

In an embodiment, the capsular polysaccharide is conjugated to a carrier protein. The capsular polysaccharide protein may be conjugated to one of the antigens (a)-(c) above. In a preferred embodiment, the composition comprises a *S. aureus* serotype 5 capsular polysaccharide conjugated to a Hla antigen and/or a type 8 capsular polysaccharide conjugated to a ClfA antigen.

In an embodiment, the ClfA antigen is a ClfA protein comprising the amino acid sequence of SEQ ID NO. 2 or an amino acid sequence at least 80%, 85%, 90%, 92%, 95%, 96%, 97%, 98% or 99% identical to SEQ ID NO. 2, or immunogenic fragment thereof.

The ClfA antigen may comprise at least one amino acid substitution selected from P116 to S and Y118 to A with reference to the amino acid sequence of SEQ ID NO. 2 (or an equivalent position in an amino acid sequence at least 80%, 85%, 90%, 92%, 95%, 96%, 97%, 98% or 99% identical to SEQ ID NO. 2), optionally comprising the sequence of any one of SEQ ID NOs 5-7 or 32.

The ClfA antigen may comprise one or more consensus sequence(s) selected from: D/E-X-N-Z-S/T (SEQ ID NO. 28) and K-D/E-X-N-Z-S/T-K (SEQ ID NO. 29), wherein X and Z are independently any amino acid apart from proline. Said consensus sequence may been added at, or substituted for, one or more amino acids between amino acid residues 313-342 of SEQ ID NO: 2, optionally substituted for the amino acid at position 1337, or at an equivalent position within an amino acid sequence at least 80%, 85%, 90%, 92%, 95%, 96%, 97%, 98% or 99% identical to SEQ ID NO: 2. In an embodiment, X is Q (glutamine) and Z is A (alanine) (e.g. K-D-Q-N-A-T-K, SEQ ID NO: 31).

In a preferred embodiment, the ClfA antigen comprises or consists of the sequence of SEQ ID NO: 7 or SEQ ID NO: 32.

In an embodiment, the Hla antigen is a Hla protein having the amino acid sequence of SEQ ID NO. 3 or an amino acid sequence at least 80%, 85%, 90%, 92%, 95%, 96%, 97%, 98% or 99% identical to SEQ ID NO. 3 or immunogenic fragment thereof.

The Hla antigen may comprise an amino acid substitution at position H35 of SEQ ID NO. 3 or at an equivalent position within an amino acid sequence at least 80%, 85%, 90%, 92%, 95%, 96%, 97%, 98% or 99% identical to SEQ ID NO. 3. In an embodiment, said amino acid substitution is optionally H to L.

The Hla antigen may comprise one or more consensus sequence(s) selected from: D/E-X-N-Z-S/T (SEQ ID NO. 28) and K-D/E-X-N-Z-S/T-K (SEQ ID NO. 29), wherein X and Z are independently any amino acid apart from proline. Said consensus sequence may be added at, or substituted for one or more amino acids of the amino acid sequence of SEQ ID NO. 3 or an amino acid sequence at least 80%, 85%, 90%, 92%, 95%, 96%, 97%, 98% or 99% identical to SEQ ID NO. 3. In an embodiment, said consensus sequence has been substituted for the amino acid at position K131 of SEQ ID NO. 3 of SEQ ID NO: 3, or at an equivalent position within an amino acid sequence at least 80%, 85%, 90%, 92%, 95%, 96%, 97%, 98% or 99% identical to SEQ ID NO: 3. In an embodiment, X is Q (glutamine) and Z is R (arginine) (e.g. K-D-Q-N-R-T-K (SEQ ID NO 30).

In a preferred embodiment, the Hla antigen comprises or consists of the sequence of SEQ ID NO: 11 or SEQ ID NO 12.

In an embodiment, the SpA antigen is a SpA protein comprising an amino acid sequence at least 80%, 85%, 90%, 92%, 95%, 96%, 97%, 98% or 99% identical to SEQ ID NO. 13, SEQ ID NO: 26 or SEQ ID NO: 27, or immunogenic fragment thereof.

The SpA antigen may comprise (a) one or more amino acid substitutions in a $V_H3$-binding sub-domain of domain E, D, A, B or C that disrupts or decreases binding to $V_H3$, and (b) one or more amino acid substitutions in an IgG Fc binding sub-domain of domain E, D, A, B or C that disrupts or decreases binding to IgG Fc.

In an embodiment, the SpA antigen comprises (i) a domain E with an amino acid substitution at the amino acid positions 34 and 35 of SEQ ID NO: 14 or at an equivalent position within an amino acid sequence at least 80%, 85%, 90%, 92%, 95%, 96%, 97%, 98% or 99% identical to SEQ ID NO: 14; a domain D with an amino acid substitution at amino acid positions 39 and 40 of SEQ ID NO: 15 or at an equivalent position within an amino acid sequence at least 80%, 85%, 90%, 92%, 95%, 96%, 97%, 98% or 99% identical to SEQ ID NO: 15; a domain A with an amino acid substitution at positions 36 and 37 of SEQ ID NO: 16 or at an equivalent position within an amino acid sequence at least 80%, 85%, 90%, 92%, 95%, 96%, 97%, 98% or 99% identical to SEQ ID NO: 16; a domain B with an amino acid substitution at positions amino acid positions 36 and 37 of SEQ ID NO: 17 or at an equivalent position within an amino acid sequence at least 80%, 85%, 90%, 92%, 95%, 96%, 97%, 98% or 99% identical to SEQ ID NO: 17, and/or a domain C with an amino acid substitution at positions amino acid positions 36 and 37 of SEQ ID NO: 18 or at an equivalent position within an amino acid sequence at least 80%, 85%, 90%, 92%, 95%, 96%, 97%, 98% or 99% identical to SEQ ID NO: 18; and/or (ii) comprises a domain E with an amino acid substitution at amino acid positions 7 and 8 of SEQ ID NO: 14 or at an equivalent position within an amino acid sequence at least 80%, 85%, 90%, 92%, 95%, 96%, 97%, 98% or 99% identical to SEQ ID NO: 14; a domain D with an amino acid substitution at amino acid positions 12 and 13 of SEQ ID NO: 15 or at an equivalent position within an amino acid sequence at least 80%, 85%, 90%, 92%, 95%, 96%, 97%, 98% or 99% identical to SEQ ID NO: 15; a domain A with an amino acid substitution at positions 9 and 10 of SEQ ID NO: 16 or at an equivalent position within an amino acid sequence at least 80%, 85%, 90%, 92%, 95%, 96%, 97%, 98% or 99% identical to SEQ ID NO: 16; a domain B with an amino acid substitution at positions amino acid positions 9 and 10 of SEQ ID NO: 17 or at an equivalent position within an amino acid sequence at least 80%, 85%, 90%, 92%, 95%, 96%, 97%, 98% or 99% identical to SEQ ID NO: 17, and/or a domain C with an amino acid substitution at positions amino acid positions 9 and 10 of SEQ ID NO: 18 or at an equivalent position within an amino acid sequence at least 80%, 85%, 90%, 92%, 95%, 96%, 97%, 98% or 99% identical to SEQ ID NO: 18. In an embodiment, said amino acid substitutions are substitution of lysine for glutamine and/or substitution of alanine for aspartic acid. Exemplary sequences are SEQ ID NOs: 19-23, 24 and 25.

In an embodiment, the SpA antigen comprises a domain D with an amino acid substitution at amino acid positions 4 and 5 of SEQ ID NO: 15 or at an equivalent position within an amino acid sequence at least 80%, 85%, 90%, 92%, 95%, 96%, 97%, 98% or 99% identical to SEQ ID NO: 15. Said amino acid substitution may suitably be glutamine to lysine and/or glutamine to arginine, e.g. QQ to KR (e.g. SEQ ID NO 24 and SEQ ID NO: 25).

In an embodiment, the SpA antigen comprises an amino acid sequence of SEQ ID NOs: 19-23, 26 or 27, or an amino acid sequence at least 80%, 85%, 90%, 92%, 95%, 96%, 97%, 98% or 99% identical to SEQ ID NOs: 19-23, 26 or 27. In a preferred embodiment, the SpA antigen comprises the amino acid sequence of SEQ ID NO: 27.

In an embodiment, the immunogenic composition comprises (i) a ClfA antigen comprising the amino acid sequence of SEQ ID NO: 7 or SEQ ID NO: 32; (ii) a Hla antigen comprising the amino acid sequence of SEQ ID NO: 11 or SEQ ID NO: 12; (iii) an SpA antigen comprising the amino acid sequence of SEQ ID NO: 27; (iv) a S. aureus serotype 5 capsular polysaccharide, and (v) a S. aureus serotype type 8 capsular polysaccharide. The ClfA antigen may be conjugated to the S. aureus serotype type 8 capsular polysaccharide, and the Hla antigen may be conjugated to the S. aureus serotype 5 capsular polysaccharide. Said ClfA-CP8 and Hla-CP5 conjugates may suitably be bioconjugates.

In an embodiment, the immunogenic composition comprises (i) a ClfA antigen comprising the amino acid sequence of SEQ ID NO: 7 or SEQ ID NO: 32; (ii) a Hla antigen comprising the amino acid sequence of SEQ ID NO: 11 or SEQ ID NO: 12; (iii) an SpA antigen comprising the amino acid sequence of SEQ ID NO: 27; (iv) a S. aureus serotype 5 capsular polysaccharide conjugated to the Hla antigen, and (v) a S. aureus serotype type 8 capsular polysaccharide conjugated to the ClfA antigen. Preferably, said ClfA-CP8 and Hla-CP5 conjugates are bioconjugates. The immunogenic composition may additionally comprise an adjuvant as described herein.

One aspect of the invention provides a vaccine comprising an immunogenic composition of the invention and a pharmaceutically acceptable excipient or carrier.

One aspect of the invention provides a kit comprising (i) a first container comprising an immunogenic composition or a vaccine of the invention; and (ii) a second container comprising an adjuvant.

One aspect of the invention provides an immunogenic composition or vaccine of the invention for use in a method of prevention or treatment of staphylococcal infection, for example *S. aureus* infection. In an embodiment, said immunogenic composition or vaccine is administered in combination with an adjuvant.

In one aspect of the invention, the immunogenic composition of the invention comprises an adjuvant. In another aspect, the immunogenic composition is for administration in combination with an adjuvant. The adjuvant may be administered concomitantly with the immunogenic composition, for example it may be mixed with the immunogenic composition before administration.

In an embodiment, the adjuvant comprises a saponin and a TLR4 agonist, suitably in liposomal formation. In an embodiment, the adjuvant further comprises a sterol. The saponin may be an immunologically active saponin fraction derived from the bark of *Quillaja Saponaria Molina*, preferably QS21. In an embodiment, the TLR4 agonist is a lipopolysaccharide. The lipopolysaccharide may be a lipid A derivative, preferably 3D-MPL. The sterol may be cholesterol. In an embodiment, the adjuvant comprises QS21 at a level of 25 μg per human dose and/or 3D-MPL at a level of 25 μg per human dose (e.g. $AS01_E$).

In one aspect, the invention provides a method of prevention or treatment of staphylococcal infection, for example *S. aureus* infection, comprising administering to a subject in need thereof an immunogenic composition or vaccine of the invention. The method may further comprise administering an adjuvant to said subject. The adjuvant may be administered concomitantly with the immunogenic composition, for example it may be mixed with the immunogenic composition before administration.

In a further aspect, the invention provides a method of making an immunogenic composition or vaccine according to any one of claims, comprising the steps of mixing antigens, and optionally an adjuvant, with a pharmaceutically acceptable excipient.

A further aspect of the invention provides a polynucleotide encoding an antigen of the immunogenic composition of the invention. Vectors comprising such a polynucleotide are also provided. Also provided is a host cell comprising a vector or polynucleotide of the invention.

Open symbols: no adjuvant, Filled symbols: AS01$_E$. Buffer control shown as filled diamonds.

Figure 6A:
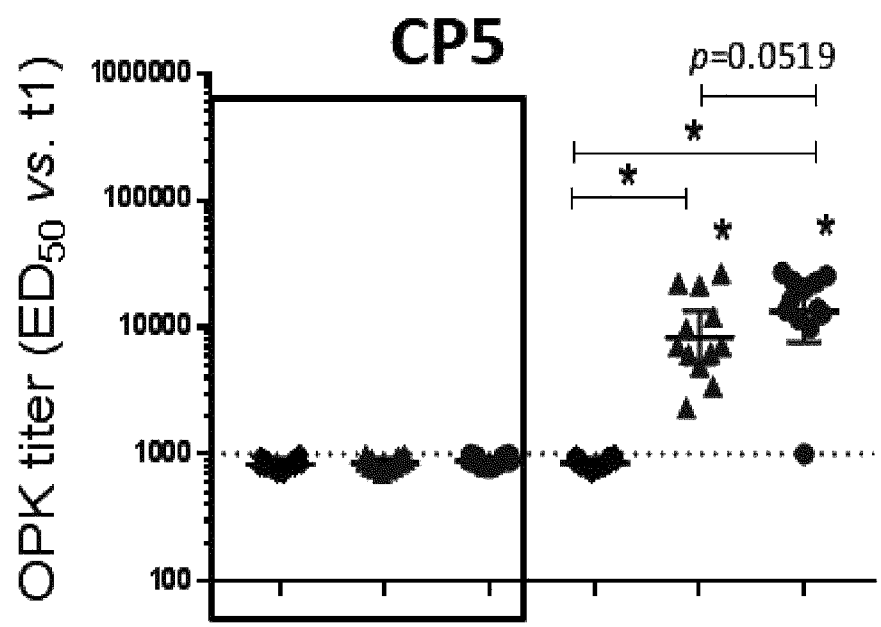
Figure 6B:
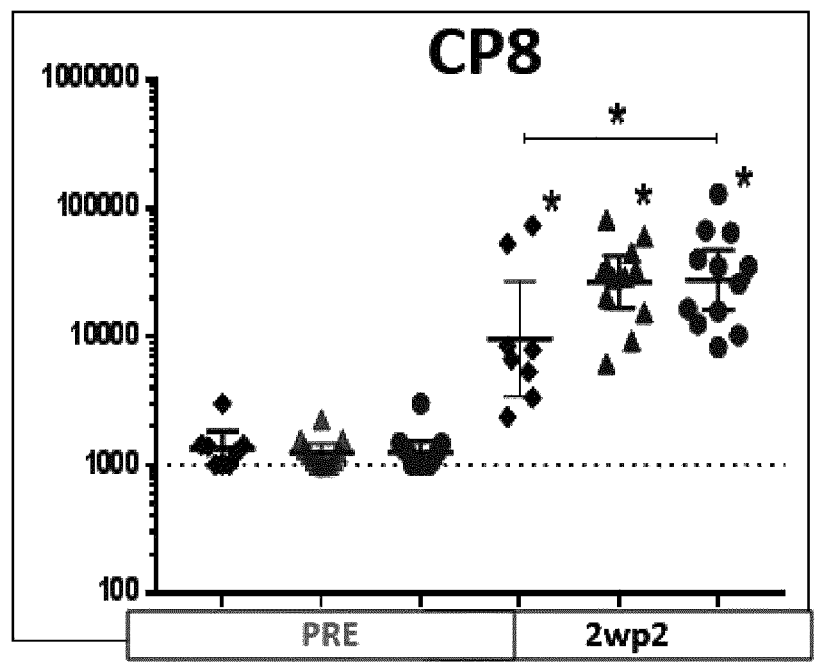

FIG. 6: Vaccine induces antibodies with OPK activity against serotype 5 (FIG. 6A) and 8 (FIG. 6B) *S. aureus* strains in pre-exposed rabbits. OPK titres of 12 individual sera were measured pre-vaccination and at 2wp2. GMTs expressed with 95% confidence intervals. Triangles: No adjuvant. Circles: AS01$_E$ adjuvant. Diamond: Buffer only.

Figure 7:
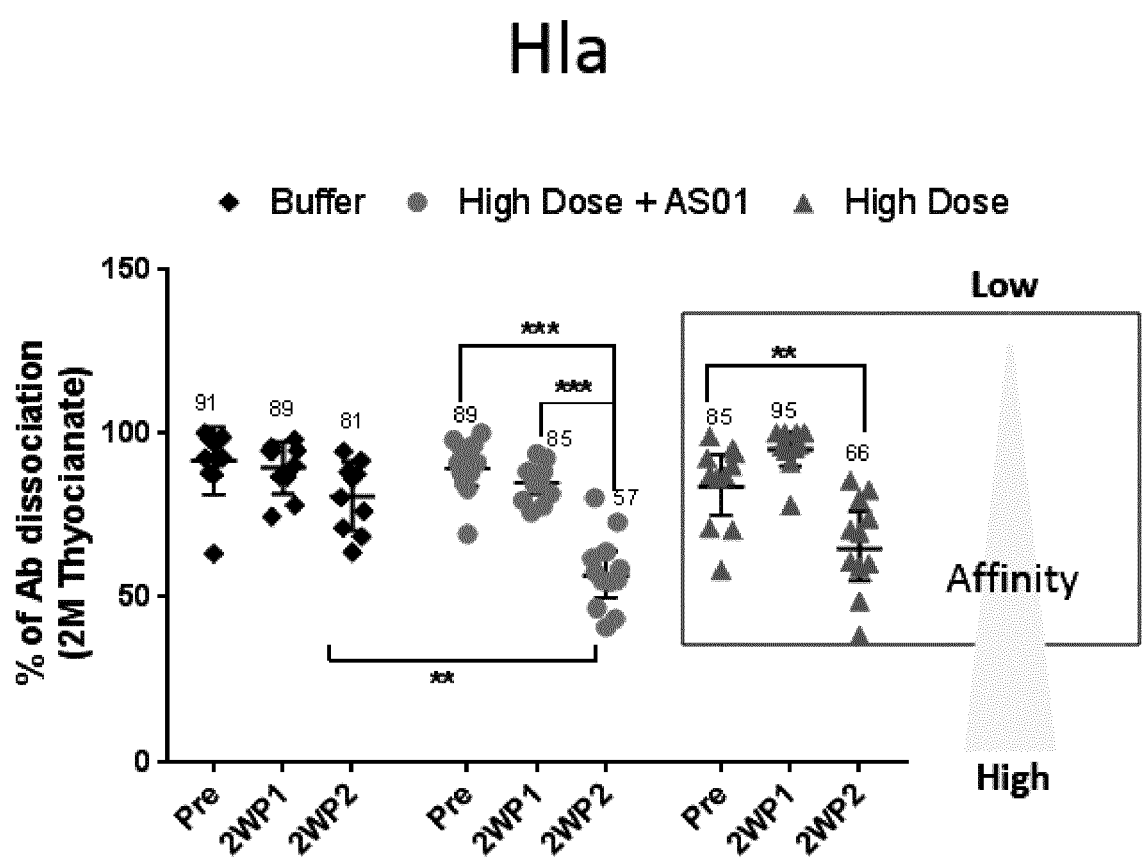

FIG. 7: Vaccination increases anti-Hla antibodies with greater affinity in pre-exposed rabbits. Percent antibody dissociation assayed in individual sera pre-vaccination, at 2wp1 and at 2wp2. GMTs expressed with 95% confidence intervals. Triangles: No adjuvant. Circles: AS01$_E$ adjuvant. Diamond: Buffer only.

Figure 8:
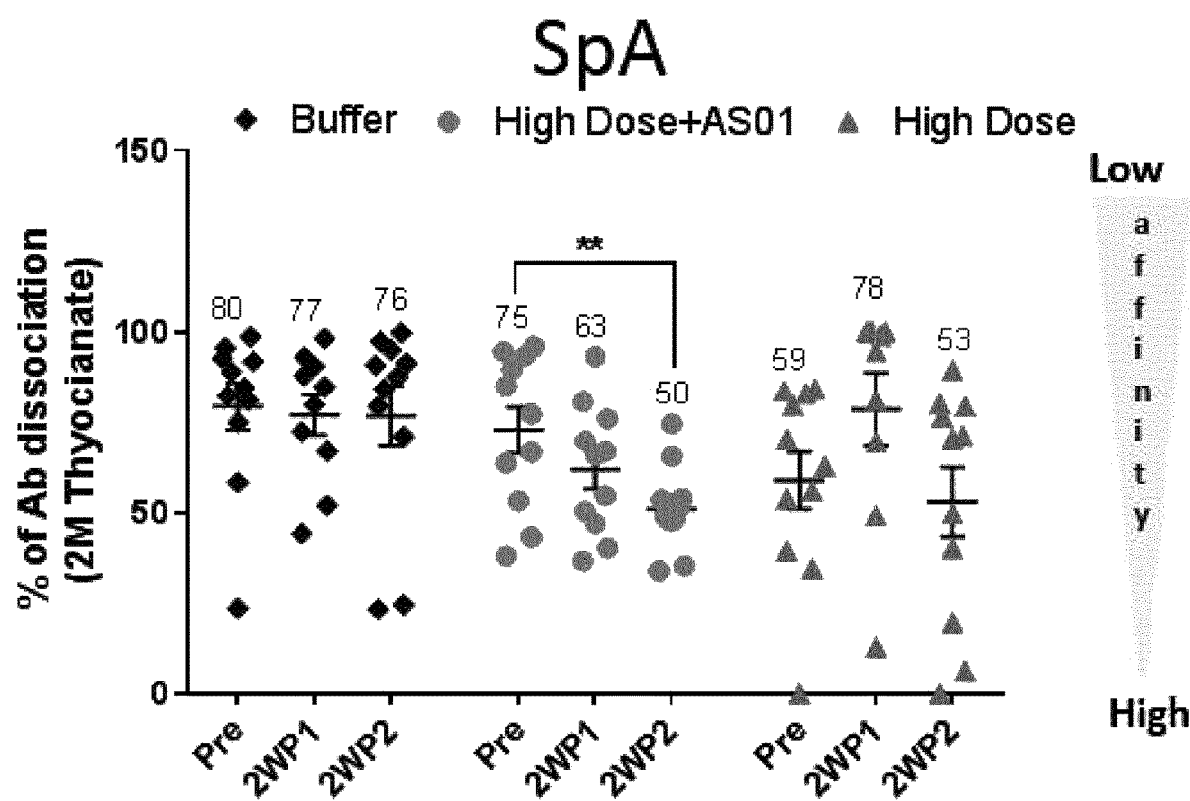

FIG. 8: Vaccination increases anti-SpA$_{mut}$ antibodies with greater affinity in pre-exposed rabbits. Percent antibody dissociation assayed in individual sera pre-vaccination, at 2wp1 and at 2wp2. GMTs expressed with 95% confidence intervals. Triangles: No adjuvant. Circles: AS01$_E$ adjuvant. Diamond: Buffer only.

Figure 9:
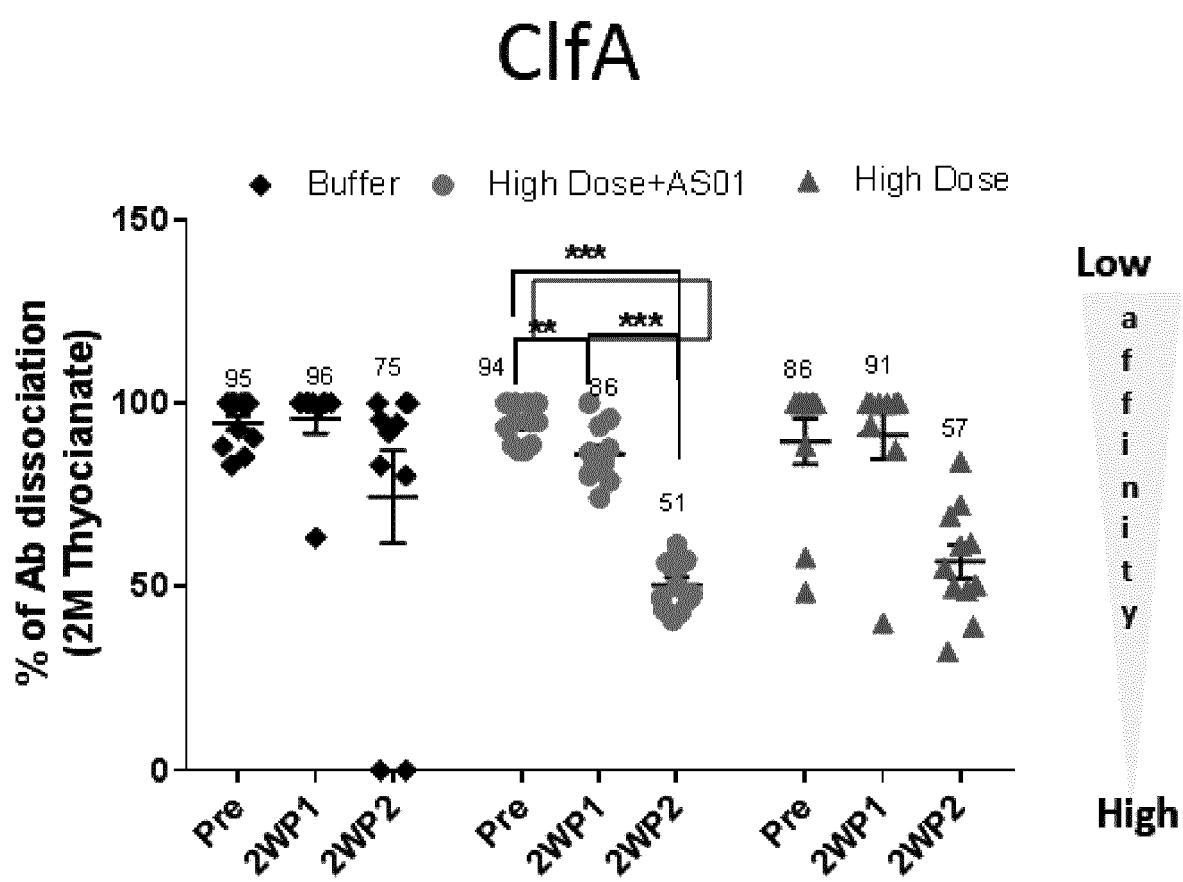

FIG. 9: Vaccination increases anti-ClfA antibodies with greater affinity in pre-exposed rabbits. Percent antibody dissociation assayed in individual sera pre-vaccination, at 2wp1 and at 2wp2. GMTs expressed with 95% confidence intervals. Triangles: No adjuvant. Circles: AS01$_E$ adjuvant. Diamond: Buffer only.

Figure 10:
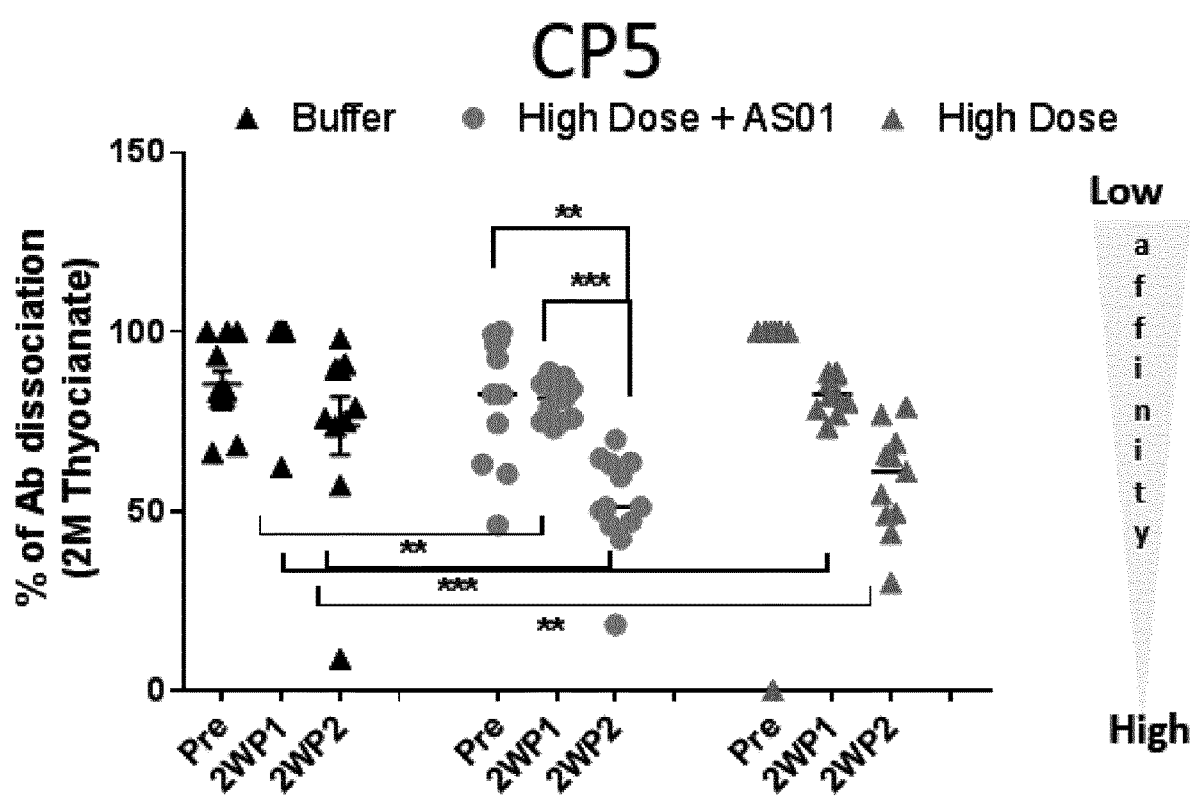

FIG. 10: Vaccination increases anti-CP5 antibodies with greater affinity in pre-exposed rabbits. Percent antibody dissociation assayed in individual sera pre-vaccination, at 2wp1 and at 2wp2. GMTs expressed with 95% confidence intervals. Triangles: No adjuvant. Circles: AS01$_E$ adjuvant. Diamond: Buffer only.

DETAILED DESCRIPTION OF THE INVENTION

Definitions

Terminology

Carrier protein: a protein covalently attached to an antigen (e.g. saccharide antigen) to create a conjugate (e.g. bioconjugate). A carrier protein activates T-cell mediated immunity in relation to the antigen to which it is conjugated.

Conjugate: saccharide (such as a capsular polysaccharide) covalently linked to a carrier protein.

Bioconjugate: a conjugate which is produced recombinantly, by expressing the enzymes required for saccharide synthesis, the carrier protein and the enzymes required for conjugation in a host cell, resulting in a conjugate in which the saccharide is N-linked to the carrier protein via N-linked protein glycosylation—the addition of carbohydrate molecules to an asparagine residue in the polypeptide chain of the target protein by enzymatic action.

Any amino acid apart from proline (pro, P): refers to an amino acid selected from the group consisting of alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), serine (ser, S), threonine (thr, T), tryptophan (trp, W), tyrosine (tyr, Y), and valine (val, V).

ClfA: Clumping factor A from *S. aureus*
Hla: Alpha-haemolysin, also known as alpha-toxin, from *S. aureus*
ClfA: Staphylococcal protein A from *S. aureus*
CP: Capsular polysaccharide
LPS: lipopolysaccharide.

Reducing end: the reducing end of an polysaccharide is the monosaccharide with a free anomeric carbon that is not involved in a glycosidic bond and is thus capable of converting to the open-chain form.

As used herein, the term "bioconjugate" refers to conjugate between a protein (e.g. a carrier protein) and an antigen (e.g. a saccharide) prepared in a host cell background, wherein host cell machinery links the antigen to the protein (e.g. N-links).

As used herein, the term "effective amount," in the context of administering a therapy (e.g. an immunogenic composition or vaccine of the invention) to a subject refers to the amount of a therapy which has a prophylactic and/or therapeutic effect(s). In certain embodiments, an "effective amount" refers to the amount of a therapy which is sufficient to achieve one, two, three, four, or more of the following effects: (i) reduce or ameliorate the severity of a bacterial infection or symptom associated therewith; (ii) reduce the duration of a bacterial infection or symptom associated therewith; (iii) prevent the progression of a bacterial infection or symptom associated therewith; (iv) cause regression of a bacterial infection or symptom associated therewith; (v) prevent the development or onset of a bacterial infection, or symptom associated therewith; (vi) prevent the recurrence of a bacterial infection or symptom associated therewith; (vii) reduce organ failure associated with a bacterial infection; (viii) reduce hospitalization of a subject having a bacterial infection; (ix) reduce hospitalization length of a subject having a bacterial infection; (x) increase the survival of a subject with a bacterial infection; (xi) eliminate a bacterial infection in a subject; (xii) inhibit or reduce a bacterial replication in a subject; and/or (xiii) enhance or improve the prophylactic or therapeutic effect(s) of another therapy.

As used herein, the term "subject" refers to an animal, in particular a mammal such as a primate (e.g. human).

As used herein, the term "immunogenic fragment" is a portion of an antigen smaller than the whole, that is capable of eliciting a humoral and/or cellular immune response in a host animal, e.g. human, specific for that fragment. Fragments of a protein can be produced using techniques known in the art, e.g. recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Typically, fragments comprise at least 10, 20, 30, 40, or 50 contiguous amino acids of the full length sequence. However, fragments may also be 100 or more, 200 or more, 300 or more or 400 or more amino acids in length. Fragments may be readily modified by adding or removing 1, 2, 3, 4, 5, 6, 7, 8, 9, 10, 20, 30, 40 or 50 amino acids from either or both of the N and C termini.

As used herein, the term "conservative amino acid substitution" involves substitution of a native amino acid residue with a non-native residue such that there is little or no effect on the size, polarity, charge, hydrophobicity, or hydrophilicity of the amino acid residue at that position, and without resulting in decreased immunogenicity. For example, these may be substitutions within the following groups: valine, glycine; glycine, alanine; valine, isoleucine, leucine; aspartic acid, glutamic acid; asparagine, glutamine;

serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

As used herein, the term "deletion" is the removal of one or more amino acid residues from the protein sequence.

As used herein, the term "insertion" is the addition of one or more non-native amino acid residues in the protein sequence.

As used herein, reference to "between amino acids . . . " (for example "between amino acids 313-342") is referring to the amino acid number counting consecutively from the N-terminus of the amino acid sequence, for example "between amino acids 313-342 . . . of SEQ ID NO. 2" refers to any position in the amino acid sequence between the $313^{rd}$ and $342^{nd}$ amino acid of SEQ ID NO. 2

Reference to "sequence identity" may be calculated over the full length of the reference sequence, or over the full length of the query sequence. Sequence alignment tools include, but are not limited to Clustal Omega (www(.)ebi (.)ac(.)ac(.)uk) MUSCLE (www(.)ebi(.)ac(.)uk), or T-coffee (www(.)tcoffee(.)org). In one aspect, the sequence alignment tool used is Clustal Omega (www(.)ebi(.)ac(.)ac(.)uk).

STATEMENT OF THE INVENTION

SpA Antigen

The wild-type SpA (staphylococcal protein A) is a cell wall-anchored surface protein which is a crucial virulence factor for lung infections, septicaemia, and abscess development and is expressed by most clinical S. aureus isolates. Wild-type SpA binds to the Fc portion of human IgG, to $V_H3$-containing B cell receptors, to von Willebrand factor at its A1 domain, and to the TNF-α receptor 1. Interaction of SpA with B cell receptors affects B cell development with effects on adaptive and innate immune responses, whereas its binding to the Fcγ of IgG interferes with opsonophagocytic clearance of staphylococci by polymorphonuclear leukocytes. The N-terminal part of mature SpA is comprised of four or five 56-61-residue Ig-binding domains, which fold into triple helical bundles connected by short linkers, and are designated in order E, D, A, B, and C. These domains display ~80% identity at the amino acid level, are 56 to 61 residues in length, and are organized as tandem repeats. The C-terminal region is comprised of "Xr", a highly repetitive yet variable octapeptide, and "Xc", a domain which abuts the cell wall anchor structure of SpA.

In the NCTC 8325 strain SpA is SAOUHSC_00069 and has amino acid sequence SEQ ID NO: 4 (GI:88193885). In the Newman strain it is nwmn_0055 (GI:151220267). A useful fragment of SEQ ID NO: 4 is amino acids 37 to 325 (SEQ ID No: 13). This fragment contains all the five SpA Ig-binding domains (which are naturally arranged from N- to C-terminus in the order E, D, A, B, C, with sequence of SEQ ID NO: 14, 15, 16, 17 and 18 respectively) and includes the most exposed domain of SpA. It also reduces the antigen's similarity with human proteins. Other useful fragments may omit 1, 2, 3 or 4 of the natural A, B, C, D and/or E domains to prevent the excessive B cell expansion which might occur if SpA functions as a B cell superantigen. Other useful fragments may include only 1, 2, 3 or 4 of the natural A, B, C, D and/or E domains e.g. comprise only the SpA(A) domain but not B to E, or comprise only the SpA(D) domain but not A, B, C or E, etc. Thus a SpA antigen useful with the invention may include 1, 2, 3, 4 or 5 IgG-binding domains.

In an embodiment, a SpA antigen of the invention can elicit an antibody (e.g. when administered to a human) that recognises SEQ ID NO: 13 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13 or amino acid sequence at least 80%, 85%, 90%, 92%, 95%, 96%, 97%, 98% or 99% identical to SEQ ID NO:13 wherein 'n' is 7 or more (e.g. 8, 10, 12, 14, 16, 18, 20, 25, 30, 35, 40, 50, 60, 70, 80, 90, 100, 150, 200, 250 or more). These SpA antigens include variants of SEQ ID NO: 13. Preferred fragments of (b) comprise an epitope from SEQ ID NO: 13 or an amino acid sequence at least 80%, 85%, 90%, 92%, 95%, 96%, 97%, 98% or 99% identical to SEQ ID NO: 13. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 13 while retaining at least one epitope of SEQ ID NO: 13. Individual IgG-binding domains might be useful immunogens, alone or in combination.

If an antigen includes only one type of SpA domain (e.g. only the Spa(A), SpA(D) or Spa(E) domain), it may include more than one copy of this domain e.g. multiple SpA(D) domains in a single polypeptide chain. It may also include one type of SpA domain and another protein or polypeptide. Thus, an antigen of the invention may be a fusion protein comprising only one type of SpA domain, such as the SpA(D) domain.

SpA antigens used with the invention may be mutated relative to SEQ ID NO: 13, such that they have decreased affinity for the Fcγ portion of human IgG and/or for the Fab portion of $V_H3$-containing human B cell receptors. This can be achieved and assessed by, for instance, following the guidance in WO2011/005341, WO12/003474 and WO2015/144653. Thus at least one Gln-Gln dipeptide in wild-type SpA can be mutated (e.g. to Lys-Lys; other possible mutations include Arg-Arg, Arg-Lys, Lys-Arg, Ala-Ala, Ser-Ser, Ser-Thr, Thr-Thr, etc.) and/or at least one Asp-Asp dipeptide in wild-type SpA can be mutated (e.g. to Ala-Ala; other possible mutations include Lys-Lys, Arg-Arg, Lys-Arg, Arg-Lys, His-His, Val-Val, etc.). These target sequences for mutation are the residues corresponding to amino acids 43, 44, 70, 71, 96, 97, 104, 105, 131, 132, 162, 163, 189, 190, 220, 221, 247, 248, 278, 279, 305 and/or 306 of SEQ ID NO: 4.

An individual domain within the antigen may be mutated at 1, 2, 3, 4, 5, 6, 7, 8, 9, 10 or more amino acids relative to SEQ ID NO: 4 (e.g. see above in relation to Gln-Gln and Asp-Asp sequences, but also see WO2011/005341 which discloses mutations at residues 3 and/or 24 of domain D, at residue 46 and/or 53 of domain A, etc.). Such mutations should not remove the antigen's ability to elicit an antibody that recognises SEQ ID NO: 13, but will reduce or remove the antigen's binding to IgG and/or other human proteins (such as human blood proteins) as noted above. In an embodiment, the mutant SpA antigen is of sequence comprising or consisting of SEQ ID NO:13 mutated in at least 1, more particularly at least 2, 3, 4, 5, 6, 7, 8, 9, 10, 11, 12, 13, 14, 15, 16, 17, 18, 19 and even more particularly 20 amino acids at the amino acids corresponding to positions 43, 44, 70, 71, 96, 97, 104, 105, 131, 132, 162, 163, 189, 190, 220, 221, 247, 248, 278, 279, 305 and/or 306 of SEQ ID NO: 4. Useful substitutions for these positions are mentioned above. For example, a SpA Domain E may be mutated at positions corresponding to amino acid residues 43, 44, 70 and/or 71 of SEQ ID NO: 1 (eg SEQ ID NO: 19). A SpA Domain D may be mutated at positions corresponding to amino acid residues 96, 97, 104, 105, 131 and/or 132 of SEQ ID NO: 4 (eg SEQ ID NO: 20 or 24). A SpA Domain A may be mutated at positions corresponding to amino acid residues 162, 163, 189 and/or 190 of SEQ ID NO: 4 (eg SEQ ID NO: 21). A SpA Domain B may be mutated at positions corresponding to amino acid residues 220, 221, 247 and/or 248 of SEQ ID NO: 4 (eg SEQ ID NO: 22). A SpA Domain C may be mutated at positions corresponding to amino acid residues 278, 279, 305 and/or 306 of SEQ ID NO: 4 (eg SEQ ID NO: 23). It is thought that the mutations at positions corresponding to positions 43, 44, 96, 97, 104, 105, 162, 163, 220, 221, 278 and/or 279 of SEQ ID NO: 4 decrease or eliminate binding to the Fcγ portion of human IgG, while those at positions corresponding to positions 70, 71, 131, 132, 189, 190, 247, 248, 305 and/or 306 of SEQ ID NO: 4. decrease or eliminate binding to the Fab portion of $V_H3$-containing human B cell receptors.

Thus, the SpA antigen preferably comprises (a) one or more amino acid substitutions in a $V_H3$-binding sub-domain of SpA domain E, D, A, B or C that disrupts or decreases binding to $V_H3$, and (b) one or more amino acid substitutions in an IgG Fc binding sub-domain of SpA domain E, D, A, B or C that disrupts or decreases binding to IgG Fc. The E/D, D/A, NB and B/C domain borders may be based on the domains described in Kim et al, 2014. Vaccine 32: 464-469.

In an embodiment, the SpA antigen comprises a domain E with an amino acid substitution at amino acid positions 7 and 8 of SEQ ID NO: 14 or at an equivalent position within an amino acid sequence at least 80%, 85%, 90%, 92%, 95%, 96%, 97%, 98% or 99% identical to SEQ ID NO: 14; a domain D with an amino acid substitution at amino acid positions 12 and 13 of SEQ ID NO: 15 or at an equivalent position within an amino acid sequence at least 80%, 85%, 90%, 92%, 95%, 96%, 97%, 98% or 99% identical to SEQ ID NO: 15; a domain A with an amino acid substitution at positions 9 and 10 of SEQ ID NO: 16 or at an equivalent position within an amino acid sequence at least 80%, 85%, 90%, 92%, 95%, 96%, 97%, 98% or 99% identical to SEQ ID NO: 16; a domain B with an amino acid substitution at positions amino acid positions 9 and 10 of SEQ ID NO: 17 or at an equivalent position within an amino acid sequence at least 80%, 85%, 90%, 92%, 95%, 96%, 97%, 98% or 99% identical to SEQ ID NO: 17, and/or a domain C with an amino acid substitution at positions amino acid positions 9 and 10 of SEQ ID NO: 18 or at an equivalent position within an amino acid sequence at least 80%, 85%, 90%, 92%, 95%, 96%, 97%, 98% or 99% identical to SEQ ID NO: 18. Preferably, said amino acid substitution is substitution of lysine for glutamine, as in for example SEQ ID NOs: 19-24. In a preferred embodiment, the SpA antigen further comprises a domain D with an amino acid substitution at amino acid positions 4 and 5 of SEQ ID NO: 15, for example a substitution of lysine or arginine for glutamine, eg KR (e.g. SEQ ID NO: 24 or SEQ ID NO: 25).

In an embodiment, the SpA antigen comprises a domain E with an amino acid substitution at the amino acid positions 34 and 35 of SEQ ID NO: 14 or at an equivalent position within an amino acid sequence at least 80%, 85%, 90%, 92%, 95%, 96%, 97%, 98% or 99% identical to SEQ ID NO: 14; a domain D with an amino acid substitution at amino acid positions 39 and 40 of SEQ ID NO: 15 or at an equivalent position within an amino acid sequence at least 80%, 85%, 90%, 92%, 95%, 96%, 97%, 98% or 99% identical to SEQ ID NO: 15; a domain A with an amino acid substitution at positions 36 and 37 of SEQ ID NO: 16 or at an equivalent position within an amino acid sequence at least 80%, 85%, 90%, 92%, 95%, 96%, 97%, 98% or 99% identical to SEQ ID NO: 16; a domain B with an amino acid substitution at positions amino acid positions 36 and 37 of SEQ ID NO: 17 or at an equivalent position within an amino acid sequence at least 80%, 85%, 90%, 92%, 95%, 96%, 97%, 98% or 99% identical to SEQ ID NO: 17, and/or a domain C with an amino acid substitution at positions amino acid positions 36 and 37 of SEQ ID NO: 18 or at an equivalent position within an amino acid sequence at least 80%, 85%, 90%, 92%, 95%, 96%, 97%, 98% or 99% identical to SEQ ID NO: 18. Preferably, said amino acid substitution is substitution of alanine for aspartic acid, as in for example SEQ ID NOs: 19-24.

Exemplary SpA antigens of the invention may comprise or consist of the sequence of SEQ ID NO: 26 or, more preferably, SEQ ID NO: 27. Other exemplary SpA antigens may have 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 26 or SEQ ID NO: 27; and/or may comprise a fragment of at least 'n' consecutive amino acids of SEQ ID NO: 26 or SEQ ID NO: 27, wherein 'n' is 7 or more (e.g. 8, 10, 12, 14, 16, 18, 20, 25, 30, 35, 40, 50, 60, 70, 80, 90, 100, 150, 200, 250 or more).

ClfA Antigen

Adherence of bacteria to host extracellular matrix components is a critical initial phase in bacterial infection. Clumping factor A (ClfA) is an important *S. aureus* adhesin which is required for virulence and helps the bacteria evade host defence mechanisms. It binds to fibrinogen in the ECM, aiding in adherence and colonisation of host tissues and additionally causing cell clumping and coating of the bacterial cells in fibrinogen, which promotes immune evasion by impairing deposition of opsonins on the bacteria.

ClfA is present in nearly all *S. aureus* strains. It is an important virulence factor, contributing to the pathogenesis of septic arthritis and endocarditis. ClfA binds to the C-terminus of the γ-chain of fibrinogen, and is thereby able to induce clumping of bacteria in fibrinogen solution. Expression of ClfA on *S. aureus* hampers phagocytosis by both macrophages and neutrophils. In neutrophils this is due to both a fibrinogen-dependent and to a fibrinogen-independent mechanism. In contrast, platelets are activated by bacteria expressing ClfA through its interaction with GPIIb/IIIa leading to aggregation. This is most efficiently executed when fibrinogen is present, but there is also a fibrinogen-independent pathway for platelet activation.

ClfA contains a 520 amino acid N-terminal A domain (the Fibrinogen Binding Region), which comprises three separately folded subdomains N1, N2 and N3. The A domain is followed by a serine-aspartate dipeptide repeat region and a cell wall- and membrane-spanning region, which contains the LPDTG-motif for sortase-promoted anchoring to the cell wall. The amino acid sequence of the A domain (subdomains N1-3) is shown in SEQ ID NO: 1. The amino acid sequence of the A domain subdomains N2N3 is shown in SEQ ID NO: 2.

In an embodiment, the ClfA antigen of the invention comprises an amino acid sequence at least 80%, 85%, 90%, 92%, 95%, 96%, 97%, 98% or 99% identical to SEQ ID NO. 1 or SEQ ID NO: 2, or is an immunogenic fragment and/or a variant of SEQ ID NO. 1 or SEQ ID NO: 2 (e.g. SEQ ID NOs 5-7) or an amino acid sequence at least 80%, 85%, 90%, 92%, 95%, 96%, 97%, 98% or 99% identical to SEQ ID NO. 1 or SEQ ID NO: 2. In an embodiment, the ClfA antigen of the invention may comprise an immunogenic fragment of SEQ ID NO. 2 or SEQ ID NOs: 5-8 comprising at least about 15, at least about 20, at least about 40, at least about 60, at least about 100, at least about 300, or at least about 400 contiguous amino acid residues of the full length sequence, wherein said polypeptide is capable of eliciting an immune response specific for said amino acid sequence.

In some embodiments, the ClfA antigen of the invention may comprise (or consist of) subdomains N1, N2 and N3 of ClfA (SEQ ID NO: 1) or an amino acid sequence at least 80%, 85%, 90%, 91%, 92%, 93%, 94%, 95%, 96%, 97%, 98% or 99% identical to SEQ ID NO: 1. In other embodiments, the modified ClfA antigen of the invention may comprise (or consist of) subdomains N2 and N3 (SEQ ID NO: 2) or an amino acid sequence at least 80%, 85%, 90%, 91%, 92%, 93%, 94%, 95%, 96%, 97%, 98% or 99% identical to SEQ ID NO: 2.

The present invention thus provides a ClfA antigen comprising (or consisting of) an amino acid sequence of SEQ ID NO. 2 or an amino acid sequence at least 80%, 85%, 90%, 91%, 92%, 93%, 94%, 95%, 96%, 97%, 98% or 99% identical to SEQ ID NO. 2 (e.g. SEQ ID NO. 5). In an embodiment, the ClfA antigen comprises one or more consensus sequence(s) for a glycosyltransferase enzyme, e.g. PglB, selected from: D/E-X-N-Z-SIT (SEQ ID NO. 28) and K-D/E-X-N-Z-SIT-K (SEQ ID NO. 29), wherein X and Z are independently any amino acid apart from proline. In an embodiment, the consensus sequence is K-D/E-X-N-Z-SIT-K (SEQ ID NO. 28), wherein X is Q (glutamine) and Z is R (arginine), e.g. K-D-Q-N-R-T-K (SEQ ID NO. 30). In a preferred embodiment, the consensus sequence is K-D/E-X-N-Z-S/T-K (SEQ ID NO. 29), wherein X is Q (glutamine) and Z is A (alanine), e.g. K-D-Q-N-A-T-K (SEQ ID NO. 31). The ClfA antigen may be additionally modified by addition of an N-terminal serine for cloning purposes, e.g. SEQ ID NO: 7. The ClfA antigen may further be modified to contain mutations which abrogate fibrinogen binding, as described below, e.g. SEQ ID NOs 5-7.

In an embodiment, the ClfA antigen of the invention comprises an amino acid sequence at least 80%, 85%, 90%, 92%, 95%, 96%, 97%, 98% or 99% identical to SEQ ID NO. 2, which sequence is a variant of SEQ ID NO. 2 which has been modified by the deletion and/or addition and/or substitution of one or more amino acids (e.g. 1, 2, 3, 4, 5, 6, 7, 8, 9, 10, 11 or 12 amino acids). Amino acid substitution may be conservative or non-conservative. In one aspect, amino acid substitution is conservative. Substitutions, deletions, additions or any combination thereof may be combined in a single variant so long as the variant is an immunogenic polypeptide. In an embodiment, the ClfA antigen of the present invention may be derived from a variant in which 1 to 10, 5 to 10, 1 to 5, 1 to 3, 1 to 2 or 1 amino acids are substituted, deleted, or added in any combination. For example, the ClfA antigen of the invention may be derived from an amino acid sequence which is a variant of SEQ ID NO. 2 in that it comprises an additional N-terminal serine (e.g. SEQ ID NO: 7).

In an embodiment, the present invention includes fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]).

In an embodiment of the invention, one or more amino acids (e.g. 1-7 amino acids, e.g. one amino acid) of the ClfA amino acid sequence (for example, having an amino acid sequence of SEQ ID NO. 2 or a ClfA amino acid sequence at least 80%, 85%, 90%, 91%, 92%, 93%, 94%, 95%, 96%, 97%, 98% or 99% identical to SEQ ID NO. 2) have been substituted by a D/E-X-N-Z-SIT (SEQ ID NO. 28) or K-D/E-X-N-Z-SIT-K (SEQ ID NO. 29) (e.g. K-D-Q-N-A-T-K (SEQ ID NO. 31)) consensus sequence. For example, a single amino acid in the ClfA amino acid sequence (e.g. SEQ ID NO. 2 or 5) may be replaced with a D/E-X-N-Z-SIT (SEQ ID NO. 28) or K-D/E-X-N-Z-SIT-K (SEQ ID NO. 29) (e.g. K-D-Q-N-A-T-K (SEQ ID NO. 31)) consensus sequence. Alternatively, 2, 3, 4, 5, 6 or 7 amino acids in the ClfA amino acid sequence (e.g. SEQ ID NO. 2 or a ClfA amino acid sequence at least 80%, 85%, 90%, 92%, 95%, 96%, 97%, 98% or 99% identical to SEQ ID NO. 2) may be replaced with a D/E-X-N-Z-S/T (SEQ ID NO. 28) or K-D/E-X-N-Z-SIT-K (SEQ ID NO. 29) (e.g. K-D-Q-N-A-T-K (SEQ ID NO. 31)) consensus sequence.

In an embodiment, a consensus sequence has been added or substituted for one or more amino acids residues 313-340 (e.g. in place of one or more amino acid residue(s) 330-340, or in place of amino acid residue Q327, D329, P331 or 1337, preferably I337) of SEQ ID NO. 2 or in an equivalent position in an amino acid sequence at least 80%, 85%, 90%, 92%, 95%, 96%, 97%, 98% or 99% identical to SEQ ID NO. 2 (e.g. SEQ ID NOS. 5-7).

Introduction of a consensus sequence(s) selected from: D/E-X-N-Z-SIT (SEQ ID NO. 28) and K-D/E-X-N-Z-S/T-K (SEQ ID NO. 29) enables the ClfA antigen to be glycosylated. Thus, the present invention also provides a ClfA antigen of the invention wherein the ClfA antigen is glycosylated.

Because the fibrinogen-binding activity of ClfA is required for it to act as a virulence factor, the ClfA antigen may be modified to reduce or eliminate fibrinogen-binding activity in order that it may be administered in vivo. Such a modified ClfA antigen may have one of the mutations described in WO2011/007004, for example mutations at one or preferably both of the amino acids corresponding to residues P116 and Y118 of SEQ ID NO: 2, for example P116S and/or Y118A. Exemplary sequences are those of SEQ ID NOs: 5-7. In an embodiment, in one aspect, the ClfA antigen of the invention comprises (or consists of) an amino acid sequence which is at least 80%, 85%, 90%, 95%, 96%, 97%, 98%, 99% or 100% identical to the sequence of SEQ ID NO. 2, said amino acid sequence comprising: the amino acid substitutions P116 to S and Y118 to A, e.g. SEQ ID NOS. 5-7 or 32.

In an embodiment, an additional amino acid residue (for example, serine or alanine) is added at the N-terminus of the mature antigen, as in for example SEQ ID NO: 7. Such a residue has the advantage of leading to more efficient cleavage of the leader sequence.

In one aspect, the ClfA antigen of the invention comprises (or consists of) an amino acid sequence which is at least 80%, 85%, 90%, 95%, 96%, 97%, 98%, 99% or 100% identical to the sequence of SEQ ID NO. 2, said amino acid sequence comprising: the amino acid substitutions P116 to S and Y118 to A, a K-D/E-X-N-Z-SIT-K (SEQ ID NO. 29) consensus sequence wherein X and Z are independently any amino acid apart from proline (preferably K-D-Q-N-A-T-K (SEQ ID NO. 31), e.g. SEQ ID NO: 6) optionally with an additional serine residue at the N-terminus (e.g. SEQ ID NO: 7). In an embodiment, a ClfA antigen of the invention has an amino acid sequence at least 97%, 98%, 99% or 100% identical to an amino acid sequence selected from SEQ ID NOs 1, 2 or 5-7. In another embodiment, the ClfA antigen of the invention has an amino acid sequence selected from SEQ ID NOs 1, 2 or 5-7.

Hla Antigen

Hla is an important secreted staphylococcal toxin. It creates a lipid-bilayer penetrating pore in the membrane of human erythrocytes and other cells, resulting in cell lysis.

In an embodiment, the Hla antigen of the invention comprises (or consists of) an amino acid sequence of SEQ ID NO. 3 or an amino acid sequence at least 80%, 85%, 90%, 91%, 92%, 93%, 94%, 95%, 96%, 97%, 98% or 99% identical to SEQ ID NO.3.

In an embodiment, the Hla antigen comprises amino acid substitutions at positions H48 and G122 of SEQ ID NO. 3 or at equivalent positions within an amino acid sequence at least 80%, 85%, 90%, 92%, 95%, 96%, 97%, 98% or 99% identical to SEQ ID NO. 3, wherein said substitutions are respectively H to C and G to C (e.g. H48C and G122C, for example SEQ ID NOs: 10-12). Said substitutions serve to introduce a disulphide bridge into the Hla antigen, which may improve stability and yield of the protein when produced recombinantly.

Hence, the Hla antigen of the invention may demonstrate a reduced tendency to aggregate compared to Hla lacking disulphide bridges, e.g. wild-type or detoxified Hla (for example, Hla H35L, e.g. SEQ ID NO: 8) For example, a suitable modified Hla antigen of the invention may be one that exhibits lower aggregation than wild-type Hla or HlaH35L (e.g. as detectable on Western blots or measured via chromatographic techniques, e.g IMAC or size exclusion chromatography), as described in the Examples. For instance, a suitable modified Hla antigen may show aggregation levels (as determined using any of the methods described herein) of 0%, 0.0005%, 0.001%, 0.005%, 0.01%, 0.05%, 0.1%, 0.5%, 1%, or 5%; about 0%, 0.0005%, 0.001%, 0.005%, 0.01%, 0.05%, 0.1%, 0.5%, 1% or 5%; less than 0.0005%, 0.001%, 0.005%, 0.01%, 0.05%, 0.1%, 0.5%, 1% or 5%; <10%, <20%, <30%, <40%, <50%, <60%, <70%, <80% or <90% of that the wild-type, detoxified (e.g. HlaH35L) Hla or other cross-linked Hla. For example, when using size exclusion chromatography or IMAC the peak representing monomeric Hla may be higher than wild-type Hla or HlaH35L or other Hla which has not been modified to reduce cross-linking, and/or the peak representing aggregated Hla may be lower.

The Hla antigen of the invention may be produced with a greater overall yield than Hla lacking disulphide bridges, e.g. wild-type or detoxified Hla (for example, Hla H35L, e.g. SEQ ID NO: 8). Where the overall yield is not greater, the modified Hla antigen may be produced with a greater yield of Hla monomer than Hla lacking disulphide bridges, e.g. wild-type or detoxified Hla (for example, Hla H35L, e.g. SEQ ID NO: 8). For instance, yield of the modified Hla antigen may be increased by 10%, 20%, 30%, 40%, 50%, 60%, 70%, 80% 90%, 110%, 120%, 150%, 200% or more, or about 10%, 20%, 30%, 40%, 50%, 60%, 70%, 80% 90%, 110%, 120%, 150%, 200% or more, compared to that of the wild-type, detoxified (e.g. HlaH35L) Hla or other cross-linked Hla. Protein yield may be determined as described below.

In an embodiment, the Hla antigen of the invention may be an immunogenic fragment and/or a variant of SEQ ID NO. 3 or an amino acid sequence at least 80%, 85%, 90%, 91%, 92%, 93%, 94%, 95%, 96%, 97%, 98% or 99% identical to SEQ ID NO.3. In an embodiment, the Hla antigen of the invention may comprise an immunogenic fragment of SEQ ID NO. 3 or an amino acid sequence at least 80%, 85%, 90%, 91%, 92%, 93%, 94%, 95%, 96%, 97%, 98% or 99% identical to SEQ ID NO.3 comprising at least about 15, at least about 20, at least about 40, or at least about 60 contiguous amino acid residues of the full length sequence, wherein said polypeptide is capable of eliciting an immune response specific for said amino acid sequence.

In an embodiment, the Hla antigen of the invention may be derived from an amino acid sequence at least 80%, 85%, 90%, 92%, 95%, 96%, 97%, 98% or 99% identical to SEQ ID NO. 3 which is a variant of SEQ ID NO. 3 which has been modified by the deletion and/or addition and/or substitution of one or more amino acids (e.g. 1, 2, 3, 4, 5, 6, 7, 8, 9, 10, 11 or 12 amino acids). Amino acid substitution may be conservative or non-conservative. In one aspect, amino acid substitution is conservative. Substitutions, deletions, additions or any combination thereof may be combined in a single variant so long as the variant is an immunogenic polypeptide. In an embodiment, the modified Hla antigen of the present invention may be derived from a variant in which 1 to 10, 5 to 10, 1 to 5, 1 to 3, 1 to 2 or 1 amino acids are substituted, deleted, or added in any combination. For example, the modified Hla antigen of the invention may be derived from an amino acid sequence which is a variant of any one of SEQ ID NOs. 3 or 8-11 in that it has one or two additional amino acids at the N terminus, for example an initial N-terminal S (e.g. SEQ ID NO. 12). The modified Hla antigen may additionally or alternatively have one or more additional amino acids at the C terminus, for example 1, 2, 3, 4, 5, or 6 amino acids. Such additional amino acids may include a peptide tag to assist in purification, and include for example GSHRHR (e.g. SEQ ID NO: 12).

In an embodiment, the present invention includes fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]).

Because Hla is a toxin, it needs to be detoxified (i.e. rendered non-toxic to a mammal, e.g. human, when provided at a dosage suitable for protection) before it can be administered in vivo. The cell lytic activity of Hla may be reduced by mutation of amino acid residues involved in pore formation, as described in Menzies and Kernodle (Menzies and Kernodle, 1994, Infect Immun 62, 1843-1847). A Hla antigen of the invention may be genetically detoxified (i.e. by mutation). Additionally and/or alternatively, the Hla antigen may be detoxified by conjugation, eg to a S. aureus capsular polysaccharide. The genetically detoxified sequences may remove undesirable activities such as the ability to form a lipid-bilayer penetrating pore, membrane permeation, cell lysis, and cytolytic activity against human erythrocytes and other cells, in order to reduce toxicity, whilst retaining the ability to induce anti-Hla protective and/or neutralising antibodies following administration to a human. For example, as described herein, a Hla antigen may be altered so that it is biologically inactive whilst still maintaining its immunogenic epitopes.

The Hla antigens of the invention may be genetically detoxified by one or more point mutations. For example, residues involved in pore formation been implicated in the lytic activity of Hla. In one aspect, the modified Hla antigens of the invention may be detoxified by amino acid substitutions as described in Menzies and Kernodle (Menzies and Kernodle, 1994, Infect Immun 62, 1843-1847), for example substitution of H35, H48, H114 and/or H259 with another amino acid such as lysine. For example, the modified Hla antigens of the invention may comprise at least one amino acid substitution selected from H35L, H114L or H259L, with reference to the amino acid sequence of SEQ ID NO. 3 (or an equivalent position in an amino acid sequence at least 80%, 85%, 90%, 92%, 95%, 96%, 97%, 98% or 99% identical to SEQ ID NO. 3). Preferably, the modified Hla antigen comprises the substitution H35L (e.g. SEQ ID NOs: 8-12).

The amino acid numbers referred to herein correspond to the amino acids in SEQ ID NO. 3 and as described above, a person skilled in the art can determine equivalent amino acid positions in an amino acid sequence at least 80%, 85%, 90%, 92%, 95%, 96%, 97%, 98% or 99% identical to SEQ ID NO. 3 by alignment.

The haemolytic activity of the Hla antigen of the invention may be assayed and characterised by methods described for example in Menzies and Kernodle, 1994, Infect Immun 62, 1843-1847. An in vitro haemolysis assay may be used to measure the haemolytic (e.g. cytolytic) activity of modified Hla antigen relative to wild-type Hla. A haemolysis inhibition assay may be used to measure the ability of antisera raised against a modified Hla antigen of the invention to inhibit haemolysis by Hla, and (typically) comparing anti-(modified Hla) antisera to anti-(wild-type Hla) antisera. For example, a suitable modified Hla antigen of the invention may be one that exhibits lower haemolytic activity than wild-type Hla (e.g. measured via an in vitro haemolysis assay). For instance, a suitable modified Hla antigen may have a specific activity (as determined using the in vitro haemolysis assay) of about (referring to each of the following values independently) 0%, 0.0005%, 0.001%, 0.005%, 0.01%, 0.05%, 0.1%, 0.5%, 1%, 5% or <10% the specific activity of the wild-type Hla. A suitable modified Hla antigen of the invention may also be one that, following administration to a host, causes the host to produce antibodies that inhibit haemolysis by wild-type Hla (e.g. via a haemolysis inhibition assay), is immunogenic (e.g. induces the production of antibodies against wild-type Hla), and/or protective (e.g. induces an immune response that protects the host against infection by or limits an already-existing infection). Assays may be used as described in the Examples.

In an embodiment of the invention, one or more amino acids (e.g. 1-7 amino acids, e.g. one amino acid) of the modified Hla amino acid sequence (for example, having an amino acid sequence of SEQ ID NO. 3 or a Hla amino acid sequence at least 80%, 85%, 90%, 91%, 92%, 93%, 94%, 95%, 96%, 97%, 98% or 99% identical to SEQ ID NO. 3, e.g. SEQ ID NO: 8 or SEQ ID NO: 10) have been substituted by a D/E-X-N-Z-S/T (SEQ ID NO. 28) or K-D/E-X-N-Z-S/T-K (SEQ ID NO. 29) (e.g. K-D-Q-N-R-T-K (SEQ ID NO. 30)) consensus sequence for a glycosyltransferase enzyme, e.g. PglB. For example, a single amino acid in the Hla amino acid sequence (e.g. SEQ ID NO. 3) may be replaced with a D/E-X-N-Z-S/T (SEQ ID NO. 28) or K-D/E-X-N-Z-S/T-K (SEQ ID NO. 29) (e.g. K-D-Q-N-R-T-K (SEQ ID NO. 30)) consensus sequence (e.g. SEQ ID NO: 9 or SEQ ID NOs: 11-12). Alternatively, 2, 3, 4, 5, 6 or 7 amino acids in the Hla amino acid sequence (e.g. SEQ ID NO. 3 or a Hla amino acid sequence at least 80%, 85%, 90%, 92%, 95%, 96%, 97%, 98% or 99% identical to SEQ ID NO. 3) may be replaced with a D/E-X-N-Z-S/T (SEQ ID NO. 28) or K-D/E-X-N-Z-S/T-K (SEQ ID NO. 29) (e.g. K-D-Q-N-R-T-K (SEQ ID NO. 30)) consensus sequence.

In an embodiment, the consensus sequence(s) selected from D/E-X-N-Z-S/T (SEQ ID NO. 28) and K-D/E-X-N-Z-SIT-K (SEQ ID NO. 29) (e.g. K-D-Q-N-R-T-K (SEQ ID NO. 30)) is added or substituted at a position corresponding to amino acid K131 of SEQ ID NO. 3 or in an equivalent position in an amino acid sequence at least 80%, 85%, 90%, 92%, 95%, 96%, 97%, 98% or 99% identical to SEQ ID NO. 1 (e.g. SEQ ID NOs: 9 and 11-12). In a preferred embodiment, said consensus sequence is substituted for the amino acid corresponding to K131 of SEQ ID NO: 3.

Introduction of a consensus sequence(s) selected from: D/E-X-N-Z-S/T (SEQ ID NO. 28) and K-D/E-X-N-Z-S/T-K (SEQ ID NO. 29) enables the Hla antigen to be glycosylated. Thus, the present invention also provides a Hla antigen of the invention which is glycosylated. In specific embodiments, the consensus sequences are introduced into specific regions of the Hla amino acid sequence, e.g. surface structures of the protein, at the N or C termini of the protein, and/or in loops that are stabilized by disulfide bridges. In an aspect of the invention, the position of the consensus sequence(s) provides improved glycosylation, for example increased yield.

Introduction of such glycosylation sites can be accomplished by, e.g. adding new amino acids to the primary structure of the antigen (i.e. the glycosylation sites are added, in full or in part), or by mutating existing amino acids in the antigen in order to generate the glycosylation sites (i.e. amino acids are not added to the antigen, but selected amino acids of the antigen are mutated so as to form glycosylation sites). Those of skill in the art will recognize that the amino acid sequence of an antigen can be readily modified using approaches known in the art, e.g. recombinant approaches that include modification of the nucleic acid sequence encoding the antigen.

In an embodiment, the Hla antigen may be further modified in that the amino acid sequence comprises one or more consensus sequence(s) selected from: D/E-X-N-Z-S/T (SEQ ID NO. 28) and K-D/E-X-N—Z-S/T-K (SEQ ID NO. 29), wherein X and Z are independently any amino acid apart from proline (e.g. SEQ ID NO. 30). These sequences may be modified by insertion of an N-terminal serine and/or alanine for cloning purposes, as described herein. The sequences may further be modified to contain detoxifying mutations, such as any one or all of the detoxifying mutations described herein. A preferred detoxifying mutation is H35L of SEQ ID No 3.

Thus, in an embodiment, the present invention provides a Hla antigen having an amino acid sequence comprising one or more consensus sequence(s) selected from: D/E-X-N-Z-S/T (SEQ ID NO. 28) and K-D/E-X-N-Z-S/T-K (SEQ ID NO. 29), wherein X and Z are independently any amino acid apart from proline, which have been recombinantly introduced into the Hla amino acid sequence of SEQ ID NO. 3 or a Hla amino acid sequence at least 80%, 85%, 90%, 92%, 95%, 96%, 97%, 98% or 99% identical to SEQ ID NO. 3 (e.g. SEQ ID NOs 9 or 10).

In a preferred embodiment, the Hla antigen of the invention comprises (or consists of) the amino acid sequence of SEQ ID NO. 11. In an embodiment, the modified Hla antigen of the invention comprises (or consists of) the amino acid sequence of any one of SEQ ID NOs. 3 or 8-11 with an N-terminal serine and/or alanine (i.e. S residues added at the N-terminus). In an embodiment, the modified Hla antigen of the invention comprises (or consists of) the amino acid sequence of SEQ ID NO. 12.

In an embodiment, the Hla antigen of the invention further comprises a "peptide tag" or "tag", i.e. a sequence of amino acids that allows for the isolation and/or identification of the modified Hla antigen. For example, adding a tag to a modified Hla antigen of the invention can be useful in the purification of that antigen and, hence, the purification of conjugate vaccines comprising the tagged modified Hla antigen. Exemplary tags that can be used herein include, without limitation, histidine (HIS) tags. In one embodiment, the tag is a hexa-histidine tag. In another embodiment, the tag is a HR tag, for example an HRHR tag. In certain embodiments, the tags used herein are removable, e.g. removal by chemical agents or by enzymatic means, once they are no longer needed, e.g. after the antigen has been purified. Optionally the peptide tag is located at the C-terminus of the amino acid sequence. Optionally the peptide tag comprises six histidine residues at the C-terminus of the amino acid sequence. Optionally the peptide tag comprises four HR residues (HRHR) at the C-terminus of the amino acid sequence. The peptide tag may comprise or be preceded by one, two or more additional amino acid residues, for example alanine, serine and/or glycine residues, e.g. GS. In one aspect, the modified Hla antigen of the invention comprises (or consists of) an amino acid sequence which is at least 80%, 85%, 90%, 92%, 95%, 97%, 98%, 99% or 100% identical to the sequence of SEQ ID NO. 3, said amino acid sequence comprising a D/E-X-N-Z-S/T (SEQ ID NO. 28) consensus sequence wherein X and Z are independently any amino acid apart from proline (e.g. K-D/E-X-N-Z-S/T-K (SEQ ID NO. 29) or K-D-Q-N-R-T-K (SEQ ID NO. 30)) and at least one amino acid substitution selected from H35L, H48C and G122C and a GSHRHR peptide tag at the C-terminus of the amino acid sequence. Optionally, the modified Hla antigen of the invention has an amino acid sequence at least 97%, 98%, 99% or 100% identical to SEQ ID NO. 3 or 9-12.

In an embodiment, a serine and/or alanine residue is added at the N-terminus of the mature protein, e.g. SA or S, preferably S (e.g. SEQ ID NO: 12). Such a residue or residues have the advantage of leading to more efficient cleavage of the leader sequence.

In one aspect, the Hla antigen of the invention comprises (or consists of) an amino acid sequence which is at least 97%, 98%, 99% or 100% identical to the sequence of SEQ ID NO. 3, said amino acid sequence comprising the amino acid substitutions G122 to C, H48 to C, and H35 to L, a K-D-Q-N-R-T-K (SEQ ID NO. 30)) substituted for the amino acid corresponding to position K131 of SEQ ID NO: 3, a HRHR tag (SEQ ID NO: 32) at the C-terminus of the amino acid sequence (E.g. SEQ ID NO: 11 or SEQ ID NO: 12).

In a preferred embodiment, said Hla antigen comprises (or consists of) the amino acid sequence of SEQ ID NO: 11. In a preferred embodiment, said Hla antigen comprises (or consists of) the amino acid sequence of SEQ ID NO: 12.

Polysaccharide Antigens

75% of *S. aureus* strains express either Type 5 or Type 8 capsular polysaccharide, so a vaccine comprising CP5 and CP8 could potentially provide protection against the majority of circulating *S. aureus* strains.

The compositions of the invention thus comprise a bacterial capsular saccharide from *S. aureus*. The bacterial capsular saccharide from *S. aureus* may be selected from a *S. aureus* serotype 5 or 8 capsular saccharide.

In an embodiment of the invention, the antigen is a repeating unit of a bacterial capsular saccharide from *S. aureus*. In an embodiment of the invention, the antigen comprises a repeat unit of a bacterial capsular saccharide from *S. aureus* serotype 5 or 8.

In an embodiment of the invention, the antigen comprises a repeat unit of a bacterial capsular saccharide from *S. aureus* serotype 8. In this embodiment, the antigen comprises:

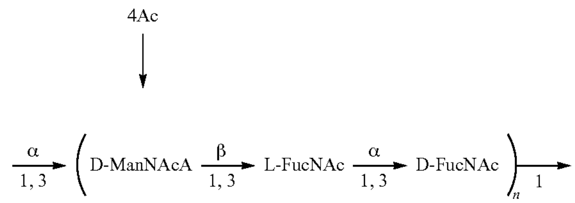

In an embodiment of the invention, the antigen comprises a repeat unit of a bacterial capsular saccharide from *Staphylococcus. aureus* serotype 5. In this embodiment of the invention, the antigen comprises:

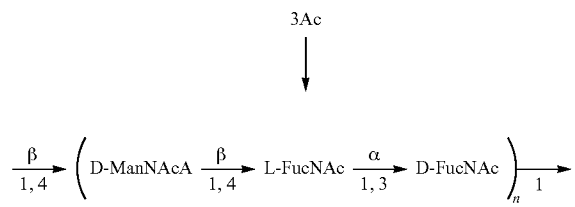

In an embodiment, the antigen is a polysaccharide. In an embodiment, the antigen comprises two or more monosaccharides, for example 3, 4, 5, 6, 7, 8, 9, 10, 12, 15, 20 or more monosaccharides. In an embodiment, the antigen is an polysaccharide containing no more than 20, 15, 12, 10, 9, or 8 monosaccharides.

In an embodiment, said capsular polysaccharide antigen is conjugated to a carrier protein. Conjugates of the invention are described below.

Conjugates

The present invention also provides a conjugate (e.g. bioconjugate) comprising (or consisting of) a capsular saccharide as described herein linked, e.g. covalently linked, to a carrier protein. In an embodiment, the carrier protein is a Hla protein of the invention. In an embodiment, the protein is a ClfA protein of the invention.

In an embodiment, the carrier protein is covalently linked to the polysaccharide antigen through a chemical linkage obtainable using a chemical conjugation method (i.e. the conjugate is produced by chemical conjugation).

In an embodiment, the chemical conjugation method is selected from the group consisting of carbodiimide chemistry, reductive animation, cyanylation chemistry (for example CDAP chemistry), maleimide chemistry, hydrazide chemistry, ester chemistry, and N-hydroysuccinimide chemistry. Conjugates can be prepared by direct reductive amination methods as described in, US200710184072 (Hausdorff) U.S. Pat. No. 4,365,170 (Jennings) and U.S. Pat. No. 4,673,574 (Anderson). Other methods are described in EP-0-161-188, EP-208375 and EP-0-477508. The conjugation method may alternatively rely on activation of the saccharide with 1-cyano-4-dimethylamino pyridinium tetrafluoroborate (CDAP) to form a cyanate ester. Such conjugates are described in PCT published application WO 93/15760 Uniformed Services University and WO 95/08348 and WO 96/29094. See also Chu C. et al Infect. Immunity, 1983 245 256.

In general the following types of chemical groups on a modified ClfA protein can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or $NH_2$. Aldehyde groups can be generated after different treatments such as: periodate, acid hydrolysis, hydrogen peroxide, etc.

Direct coupling approaches:

Saccharide-OH+CNBr or CDAP→cyanate ester+$NH_2$-Protein→conjugate

Saccharide-aldehyde+$NH_2$-Protein→Schiff base+NaCNBH3→conjugate

Saccharide-COOH+$NH_2$-Protein+EDAC→conjugate

Saccharide-$NH_2$+COOH-Protein+EDAC→conjugate

Indirect coupling via spacer (linker) approaches:

Saccharide-OH+CNBr or CDAP→cyanate ester+$NH_2$—$NH_2$→saccharide-$NH_2$+COOH-Protein+EDAC→conjugate Saccharide-OH+CNBr or CDAP→cyanate ester+$NH_2$—SH→saccharide-SH+SH-Protein (native Protein with an exposed cysteine or obtained after modification of amino groups of the protein by SPDP for instance)→saccharide-S—S-Protein Saccharide-OH+CNBr or CDAP→cyanate ester+$NH_2$—SH→saccharide-SH+maleimide-Protein (modification of amino groups)→conjugate Saccharide-OH+CNBr or CDAP→cyanate ester+$NH_2$—SH→Saccharide-SH+haloacetylated-Protein→Conjugate Saccharide-COOH+EDAC+$NH_2$—$NH_2$→saccharide $NH_2$+EDAC+COOH-Protein→conjugate Saccharide-COOH+EDAC+$NH_2$—SH→saccharide-SH+SH-Protein (native Protein with an exposed cysteine or obtained after modification of amino groups of the protein by SPDP for instance)→saccharide-S—S-Protein Saccharide-COOH+EDAC+$NH_2$—SH→saccharide—SH+maleimide-Protein (modification of amino groups)→conjugate Saccharide-COOH+EDAC+$NH_2$—SH→Saccharide-SH+haloacetylated-Protein→Conjugate Saccharide-Aldehyde+$NH_2$—$NH_2$→saccharide-$NH_2$+EDAC+COOH-Protein→conjugate Note: instead of EDAC above, any suitable carbodiimide may be used.

In an embodiment, the antigen is directly linked to the carrier protein.

In an embodiment, the antigen is attached to the carrier protein via a linker. Optionally, the linker is selected from the group consisting of linkers with 4-12 carbon atoms, bifunctional linkers, linkers containing 1 or 2 reactive amino groups at the end, B-proprionamido, nitrophenyl-ethylamine, haloacyl halides, 6-aminocaproic acid and ADH. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS (4-Maleimidobutyric acid N-hydroxysuccinimide ester)) or a haloacetylated carrier protein (for example using SIAB (succinimidyl (4-iodoacetyl)aminobenzoate), or SIA (succinimidyl iodoacetate), or SBAP (succinimidyl-3-(bromoacetamide)propionate)). In an embodiment, the cyanate ester (optionally made by CDAP chemistry) is coupled with hexane diamine or ADH (adipic acid dihydrazide) and the amino-derivatised saccharide is conjugated to the carrier protein using carbodiimide (e.g. 1-Ethyl-3-(3-dimethylaminopropyl)carbodiimide (EDAC or EDC)) chemistry via a carboxyl group on the protein carrier. Such conjugates are described in PCT published application WO 93/15760 Uniformed Services University and WO 95/08348 and WO 96/29094.

In an embodiment, the amino acid residue on the carrier protein to which the antigen is linked is not an asparagine residue and in this case, the conjugate is typically produced by chemical conjugation. In an embodiment, the amino acid residue on the carrier protein to which the antigen is linked is selected from the group consisting of: Ala, Arg, Asp, Cys, Gly, Glu, Gln, His, Ile, Leu, Lys, Met, Phe, Pro, Ser, Thr, Trp, Tyr, and Val. Optionally, the amino acid is: an amino acid containing a terminal amine group, a lysine, an arginine, a glutaminic acid, an aspartic acid, a cysteine, a tyrosine, a histidine or a tryptophan. Optionally, the antigen is covalently linked to amino acid on the carrier protein selected from: aspartic acid, glutamic acid, lysine, cysteine, tyrosine, histidine, arginine or tryptophan.

In an embodiment, the antigen is linked to an amino acid on the carrier protein selected from asparagine, aspartic acid, glutamic acid, lysine, cysteine, tyrosine, histidine, arginine or tryptophan (e.g. asparagine). In an embodiment, the amino acid residue on the carrier protein to which the antigen is linked is an asparagine residue. In an embodiment, the amino acid residue on the carrier protein to which the antigen is linked is part of the D/E-X-N-Z-S/T (SEQ ID NO. 28) and K-D/E-X-N-Z-S/T-K (SEQ ID NO. 29) consensus sequence (e.g. the asparagine in the D/E-X-N-Z-S/T (SEQ ID NO. 28) and K-D/E-X-N-Z-S/T-K (SEQ ID NO. 29) consensus sequence).

The invention provides a bioconjugate comprising a ClfA or Hla protein as described herein linked to a StaphylococcuS. aureus capsular saccharide (e.g. capsular polysaccharide). In a specific embodiment, the bioconjugate comprises a ClfA or Hla protein as described herein and an antigen selected from a capsular saccharide (e.g. capsular polysaccharide) of StaphylococcuS. aureus serotype CP5 or CP8. In an embodiment, the bioconjugate comprises a ClfA antigen of the invention and an antigen from a capsular saccharide (e.g. capsular polysaccharide) of StaphylococcuS. aureus serotype CP8. In an embodiment, the bioconjugate comprises a Hla antigen of the invention and an antigen from a capsular saccharide (e.g. capsular polysaccharide) of StaphylococcuS. aureus serotype CP5.

Methods of producing bioconjugates using host cells are described for example in WO 2003/074687, WO 2006/119987 and WO2011/138361.

Bioconjugates may be produced in a host cell comprising: one or more nucleic acids that encode glycosyltransferase(s); a nucleic acid that encodes an oligosaccharyl transferase; a nucleic acid that encodes a polypeptide of the invention; and optionally a nucleic acid that encodes a polymerase (e.g. wzy).

Host cells that can be used to produce the bioconjugates of the invention include archea, prokaryotic host cells, and eukaryotic host cells. Exemplary prokaryotic host cells for use in production of the bioconjugates of the invention, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell is *E. coli*.

In an embodiment, the host cells used to produce the bioconjugates of the invention are engineered to comprise heterologous nucleic acids, e.g. heterologous nucleic acids that encode one or more carrier proteins and/or heterologous nucleic acids that encode one or more proteins, e.g. genes encoding one or more proteins. In a specific embodiment, heterologous nucleic acids that encode proteins involved in glycosylation pathways (e.g. prokaryotic and/or eukaryotic glycosylation pathways) may be introduced into the host cells. Such nucleic acids may encode proteins including, without limitation, oligosaccharyl transferases, epimerases, flippases, polymerases, and/or glycosyltransferases. Heterologous nucleic acids (e.g. nucleic acids that encode carrier proteins and/or nucleic acids that encode other proteins, e.g. proteins involved in glycosylation) can be introduced into the host cells using methods such as electroporation, chemical transformation by heat shock, natural transformation, phage transduction, and conjugation. In specific embodiments, heterologous nucleic acids are introduced into the host cells using a plasmid, e.g. the heterologous nucleic acids are expressed in the host cells by a plasmid (e.g. an expression vector). In another specific embodiment, heterologous nucleic acids are introduced into the host cells using the method of insertion described in International Patent application No. PCT/EP2013/068737 (published as WO 14/037585).

Additional modifications may be introduced (e.g. using recombinant techniques) into the host cells. For example, host cell nucleic acids (e.g. genes) that encode proteins that form part of a possibly competing or interfering glycosylation pathway (e.g. compete or interfere with one or more heterologous genes involved in glycosylation that are recombinantly introduced into the host cell) can be deleted or modified in the host cell background (genome) in a manner that makes them inactive/dysfunctional (i.e. the host cell nucleic acids that are deleted/modified do not encode a functional protein or do not encode a protein whatsoever). When nucleic acids are deleted from the genome of the host cells, they may be replaced by a desirable sequence, e.g. a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g. Feldman et al. 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-pyrophosphate biosynthesis genes (e.g. uppS (Undecaprenyl pyrophosphate synthase), uppP (Undecaprenyl diphosphatase)), Und-P recycling genes, metabolic enzymes involved in nucleotide activated sugar biosynthesis, enterobacterial common antigen cluster, and prophage O antigen modification clusters like the gtrABS cluster.

Such a modified prokaryotic host cell comprises nucleic acids encoding enzymes capable of producing a bioconjugate comprising an antigen, for example a saccharide antigen attached to a polypeptide of the invention. Such host cells may naturally express nucleic acids specific for production of a saccharide antigen, or the host cells may be made to express such nucleic acids, i.e. in certain embodiments said nucleic acids are heterologous to the host cells. One or more of said nucleic acids specific for production of a saccharide antigen may be heterologous to the host cell and integrated into the genome of the host cell. The host cells may comprise nucleic acids encoding additional enzymes active in the N-glycosylation of proteins, e.g. the host cells further comprise a nucleic acid encoding an oligosaccharyl transferase and/or one or more nucleic acids encoding other glycosyltransferases.

Nucleic acid sequences comprising capsular polysaccharide gene clusters can be inserted into the host cells. For example, the capsular polysaccharide gene cluster inserted into a host cell may be a capsular polysaccharide gene cluster from a staphylococcal strain (e.g. *S. aureus*), as described below.

The host cells comprise, and/or can be modified to comprise, nucleic acids that encode genetic machinery (e.g. glycosyltransferases, flippases, polymerases, and/or oligosaccharyltransferases) capable of producing hybrid polysaccharides, as well as genetic machinery capable of linking antigens to the polypeptide of the invention.

*S. aureus* capsular polysaccharides are assembled on the bacterial membrane carrier lipid undecaprenyl pyrophosphate by a conserved pathway that shares homology to the polymerase-dependent pathway of O polysaccharide synthesis in Gram-negative bacteria. O antigen assembly is initiated by the transfer of a sugar phosphate from a DP-donor to undecaprenyl phosphate. The lipid linked O antigen is assembled at the cytoplasmic side of the inner membrane by sequential action of different glycosyltransferases. The glycolipid is then flipped to the periplasmic space and polymerised. By replacing the O antigen ligase WaaL with the oligosaccharyltransferase PglB, the polymerised O antigen can be transferred to a protein carrier rather than to the lipid A core.

The host cells further comprise nucleic acids that encode glycosyltransferases that produce a polysaccharide repeating unit. Preferably, said repeating unit does not comprise a hexose at the reducing end, and said polysaccharide repeat unit is derived from a donor polysaccharide repeat unit that comprises a hexose at the reducing end.

The host cells may comprise a nucleic acid that encodes a glycosyltransferase that assembles a hexose monosaccharide derivative onto undecaprenyl pyrophosphate (Und-PP). In one aspect, the glycosyltransferase that assembles a hexose monosaccharide derivative onto Und-PP is heterologous to the host cell and/or heterologous to one or more of the genes that encode glycosyltransferase(s). Said glycosyltransferase can be derived from, e.g. *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, Lactococcus species, Lactobacillus species, Pseudomonas species, Corynebacterium species, Streptomyces species, Streptococcus species, Enterococcus species, Staphylococcus species, Bacillus species, Clostridium species, Listeria species, or Campylobacter species. Usually, the glycosyltransferase that assembles a hexose monosaccharide derivative onto Und-PP is wecA, optionally from E. coli (wecA can assemble GlcNAc onto UndP from UDP-GlcNAc). The hexose monosaccharide may be selected from the group consisting of glucose, galactose, rhamnose, arabinotol, fucose and mannose (e.g. galactose).

The host cells may comprise nucleic acids that encode one or more glycosyltransferases capable of adding a monosaccharide to the hexose monosaccharide derivative assembled on Und-PP. For example, said one or more glycosyltransferases capable of adding a monosaccharide to the hexose monosaccharide derivative may be the galactosyltransferase (wfeD) from Shigella boyedii; the galactofuranosyltransferase (wbeY) from E. coli O28; or the galactofuranosyltransferase (wfdK) from E. coli O167. Galf-transferases, such as wfdK and wbeY, can transfer Galf (Galactofuranose) from UDP-Galf to -GlcNAc-P-P-Undecaprenyl. Preferably, said one or more glycosyltransferases capable of adding a monosaccharide to the hexose monosaccharide derivative are the galactofuranosyltransferase (wbeY) from E. coli O28 and the galactofuranosyltransferase (wfdK) from E. coli O167.

The host cells may comprise nucleic acids that encode glycosyltransferases that assemble the donor polysaccharide repeating unit onto the hexose monosaccharide derivative. The glycosyltransferases that assemble the donor polysaccharide repeating unit onto the hexose monosaccharide derivative may comprise a glycosyltransferase that is capable of adding the hexose monosaccharide present at the reducing end of the first repeating unit of the donor polysaccharide to the hexose monosaccharide derivative. Exemplary glycosyltransferases include galactosyltransferases (wciP), e.g. wciP from E. coli O21.

The glycosyltransferases that assemble the donor polysaccharide repeating unit onto the hexose monosaccharide derivative comprise a glycosyltransferase that is capable of adding the monosaccharide that is adjacent to the hexose monosaccharide present at the reducing end of the first repeating unit of the donor polysaccharide to the hexose monosaccharide present at the reducing end of the first repeating unit of the donor polysaccharide. Exemplary glycosyltransferases include glucosyltransferase (wciQ), e.g. wciQ from E. coli O21.

The host cell may comprise glycosyltransferases for synthesis of the repeating units of an polysaccharide selected from the StaphylococcuS. aureus CP5 or CP8 gene cluster. S. aureus CP5 and CP8 have a similar structure to P. aeruginosa O11 antigen synthetic genes, so these genes may be combined with E. coli monosaccharide synthesis genes to synthesise an undecaprenyl pyrophosphate-linked CP5 or CP8 polymer consisting of repeatinging trisaccharide units.

Glycosyltransferases sufficient for synthesis of the repeating units of the CP5 or CP8 saccharide comprise capH, capI, capJ and/or capK from S. aureus CP5 or CP8. Optionally the host cell also comprises capD, capE, capF, capG, capL, capM, capN, capO, capP from S. aureus CP5 or CP8. Alternatively, the host cell also comprises wbjB, wbjC, wbjD, wbjE, wbjF, wbjL, wbpM, wzz and/or wzx from P. aeruginosa O11 and wecB, wecC from E. coli O16.

Glycosyltransferases sufficient for synthesis of the repeating units of the CP5 saccharide comprise capH, capI, capJ and/or capK from S. aureus CP5. Optionally the host cell also comprises capD, capE, capF, capG, capL, capM, capN, capO, capP from S. aureus CP5. Alternatively, the host cell also comprises wbjB, wbjC, wbjD, wbjE, wbjF, wbjL, wbpM, wzz and/or wzx from P. aeruginosa O11 and wecB, wecC from E. coli O16.

The host cell may comprise glycosyltransferases that assemble the donor polysaccharide repeating unit onto the hexose monosaccharide derivative comprise a glycosyltransferase that is capable of adding the hexose monosaccharide present at the reducing end of the first repeating unit of the donor polysaccharide to the hexose monosaccharide derivative.

N-linked protein glycosylation—the addition of carbohydrate molecules to an asparagine residue in the polypeptide chain of the target protein—is accomplished by the enzymatic oligosaccharyltransferase complex (OST) responsible for the transfer of a preassembled oligosaccharide from a lipid carrier (dolichol phosphate) to an asparagine residue of a nascent protein within the conserved sequence Asn-X-Ser/Thr (where X is any amino acid except proline) in the Endoplasmic reticulum.

It has been shown that a bacterium, the food-borne pathogen Campylobacter jejuni, can also N-glycosylate its proteins (Wacker et al. Science. 2002; 298(5599):1790-3) due to the fact that it possesses its own glycosylation machinery. The machinery responsible of this reaction is encoded by a cluster called "pgl" (for protein glycosylation).

The C. jejuni glycosylation machinery can be transferred to E. coli to allow for the glycosylation of recombinant proteins expressed by the E. coli cells. Previous studies have demonstrated how to generate E. coli strains that can perform N-glycosylation (see, e.g. Wacker et al. Science. 2002; 298 (5599):1790-3; Nita-Lazar et al. Glycobiology. 2005; 15(4):361-7; Feldman et al. Proc Natl Acad Sci USA. 2005; 102(8):3016-21; Kowarik et al. EMBO J. 2006; 25(9):1957-66; Wacker et al. Proc Natl Acad Sci USA. 2006; 103(18): 7088-93; International Patent Application Publication Nos. WO2003/074687, WO2006/119987, WO 2009/104074, and WO/2011/06261, and WO2011/138361). PglB mutants having optimised properties are described in WO2016/107818. A preferred mutant is PglB$_{cuoN311V\text{-}K482R\text{-}D483H\text{-}A669V}$.

Oligosaccharyl transferases transfer lipid-linked oligosaccharides to asparagine residues of nascent polypeptide chains that comprise a N-glycosylation consensus motif, e.g. Asn-X-Ser(Thr), wherein X can be any amino acid except Pro; or Asp(Glu)-X-Asn-Z-Ser(Thr), wherein X and Z are independently selected from any natural amino acid except Pro (see WO 2006/119987). See, e.g. WO 2003/074687 and WO 2006/119987.

The host cells comprise a nucleic acid that encodes an oligosaccharyl transferase. The nucleic acid that encodes an oligosaccharyl transferase can be native to the host cell, or can be introduced into the host cell using genetic approaches, as described above. Preferably, the oligosaccharyl transferase is an oligosaccharyl transferase from Campylobacter, specifically Campylobacter jejuni (i.e. pglB; see, e.g. Wacker et al. 2002, Science 298:1790-1793; see also, e.g. NCBI Gene ID: 3231775, UniProt Accession No. O86154).

Hence, bioconjugates of S. aureus capsular polysaccharides may be produced in a prokaryotic host cell comprising (i) a glycosyltransferase derived from an capsular polysaccharide cluster from S. aureus, wherein said glycosyltransferase is integrated into the genome of said host cell; (ii) a nucleic acid encoding an oligosaccharyl transferase (e.g. pglB from Campylobacter jejuni), wherein said nucleic acid encoding an oligosaccharyl transferase is plasmid-borne and/or integrated into the genome of the host cell; and (iii)

a polypeptide of the invention, wherein said polypeptide is either plasmid-borne or integrated into the genome of the host cell. The waaL gene of the host cell may been functionally inactivated or deleted, e.g. replaced by a nucleic acid encoding an oligosaccharyltransferase, for example by C. jejuni pglB.

To produce poly- and oligosaccharides of capsular saccharides, a polymerase (e.g. wzy) is introduced into a host cell (i.e. the polymerase is heterologous to the host cell). For production of S. aureus CP5 and CP8, the polymerase introduced into the host cells is the wzy gene from a capsular polysaccharide gene cluster of S. aureus CP5 or CP8 (cap5J/cap8I).

Finally, a flippase (wzx or homologue) is introduced into the host cell (i.e. the flippase is heterologous to the host cell). Flippases translocate wild type repeating units and/or their corresponding engineered (hybrid) repeating units from the cytoplasm into the periplasm of host cells (e.g. E. coli). Thus, a host cell may comprise a nucleic acid that encodes a flippase (wzx). Preferably, a flippase of a capsular polysaccharide biosynthetic pathway of S. aureus is introduced into a host cell. The flippase introduced into the host cells may be the capK gene from a capsular polysaccharide gene cluster of S. aureus CP5 or CP8. Other flippases that can be introduced into the host cells are for example from Campylobacter jejuni (e.g. pglK).

The bioconjugates of the invention can be purified for example, by chromatography (e.g. ion exchange, cationic exchange, anionic exchange, affinity, and sizing column chromatography), centrifugation, differential solubility, or by any other standard technique for the purification of proteins. See, e.g. Saraswat et al. 2013, Biomed. Res. Int. ID#312709 (p. 1-18); see also the methods described in WO 2009/104074. Further, the bioconjugates may be fused to heterologous polypeptide sequences described herein or otherwise known in the art to facilitate purification. For example, the Hla protein may incorporate a peptide tag such as a HRHR tag for purification by cationic exchange (e.g. SEQ ID NO: 12). The actual conditions used to purify a particular bioconjugate will depend, in part, on the synthesis strategy and on factors such as net charge, hydrophobicity, and/or hydrophilicity of the bioconjugate, and will be apparent to those having skill in the art.

A further aspect of the invention is a process for producing a bioconjugate that comprises (or consists of) a ClfA or Hla antigen linked to a saccharide, said method comprising (i) culturing the host cell of the invention under conditions suitable for the production of proteins (and optionally under conditions suitable for the production of saccharides) and (ii) isolating the bioconjugate produced by said host cell.

A further aspect of the invention is a bioconjugate produced by the process of the invention, wherein said bioconjugate comprises a S. aureus polysaccharide linked to a ClfA or Hla antigen.

Immunogenic Compositions and Vaccines

The immunogenic composition of the present invention may be formulated into pharmaceutical compositions prior to administration to a subject. According to one aspect, the invention provides a pharmaceutical composition comprising an immunogenic composition of the invention and a pharmaceutically acceptable excipient or carrier.

The present invention also provides a vaccine comprising an immunogenic composition of the invention and a pharmaceutically acceptable excipient or carrier.

Also provided is an adjuvant composition for use with the immunogenic compositions and vaccines of the invention as described herein, which composition comprises an adjuvant and a pharmaceutically acceptable excipient or carrier.

Pharmaceutically acceptable excipients and carriers can be selected by those of skill in the art. For example, the pharmaceutically acceptable excipient or carrier can include a buffer, such as Tris (trimethamine), phosphate (e.g. sodium phosphate), acetate, borate (e.g. sodium borate), citrate, glycine, histidine and succinate (e.g. sodium succinate), suitably sodium chloride, histidine, sodium phosphate or sodium succinate. The pharmaceutically acceptable excipient may include a salt, for example sodium chloride, potassium chloride or magnesium chloride. Optionally, the pharmaceutically acceptable excipient contains at least one component that stabilizes solubility and/or stability. Examples of solubilizing/stabilizing agents include detergents, for example laurel sarcosine and/or polysorbate (e.g. TWEEN™ 80). Examples of stabilizing agents also include poloxamer (e.g. poloxamer 124, poloxamer 188, poloxamer 237, poloxamer 338 and poloxamer 407). The pharmaceutically acceptable excipient may include a non-ionic surfactant, for example polyoxyethylene sorbitan fatty acid esters, Polysorbate-80 (TWEEN™ 80), Polysorbate-60 (TWEEN™ 60), Polysorbate-40 (TWEEN™ 40) and Polysorbate-20 (TWEEN™ 20), or polyoxyethylene alkyl ethers (suitably polysorbate-80). Alternative solubilizing/stabilizing agents include arginine, and glass forming polyols (such as sucrose, trehalose and the like). The pharmaceutically excipient may be a preservative, for example phenol, 2-phenoxyethanol, or thiomersal. Other pharmaceutically acceptable excipients include sugars (e.g. lactose, sucrose), and proteins (e.g. gelatine and albumin). Pharmaceutically acceptable carriers include water, saline solutions, aqueous dextrose and glycerol solutions. Numerous pharmaceutically acceptable excipients and carriers are described, for example, in Remington's Pharmaceutical Sciences, by E. W. Martin, Mack Publishing Co. Easton, Pa., 5th Edition (975).

In an embodiment, the compositions comprises a buffer. The pH of a liquid preparation is adjusted in view of the components of the composition and necessary suitability for administration to the subject. Suitably, the pH of a liquid mixture is at least 4, at least 5, at least 5.5, at least 5.8, at least 6. The pH of the liquid mixture may be less than 9, less than 8, less than 7.5 or less than 7. In other embodiments, pH of the liquid mixture is between 4 and 9, between 5 and 8, such as between 5.5 and 8.

An appropriate buffer may be selected from acetate, citrate, histidine, maleate, phosphate, succinate, tartrate and TRIS. In one embodiment, the buffer is a phosphate buffer such as Na/Na$_2$PO$_4$, Na/K$_2$PO$_4$ or K/K$_2$PO$_4$.

The buffer can be present in the liquid mixture in an amount of at least 6 mM, at least 10 mM or at least 40 mM. The buffer can be present in the liquid mixture in an amount of less than 100 mM, less than 60 mM or less than 40 mM.

In an embodiment, the compositions of the invention have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions of the present invention when reconstituted will have an osmolality in the range of 250 to 750 mOsm/kg, for example, the osmolality may be in the range of 250 to 550 mOsm/kg, such as in the range of 280 to 500 mOsm/kg.

Osmolality may be measured according to techniques known in the art, such as by the use of a commercially available osmometer, for example the Advanced® Model 2020 available from Advanced Instruments Inc. (USA).

An "isotonicity agent" is a compound that is physiologically tolerated and imparts a suitable tonicity to a formulation to prevent the net flow of water across cell membranes that are in contact with the formulation. In some embodiments, the isotonicity agent used for the composition is a salt (or mixtures of salts). In other embodiments, however, the composition comprises a non-ionic isotonicity agent and the concentration of sodium chloride in the composition is less than 100 mM, such as less than 80 mM, e.g. less than 50 mM, such as less 40 mM, less than 30 mM and especially less than 20 mM. The ionic strength in the composition may be less than 100 mM, such as less than 80 mM, e.g. less than 50 mM, such as less 40 mM or less than 30 mM.

In a particular embodiment, the non-ionic isotonicity agent is a polyol, such as sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369.

In an embodiment, the compositions of the invention additionally comprise one or more salts, e.g. sodium chloride, calcium chloride, sodium phosphate, monosodium glutamate, and Aluminum salts (e.g. Aluminum hydroxide, Aluminum phosphate, Alum (potassium Aluminum sulfate), or a mixture of such Aluminum salts). In other embodiments, the compositions of the invention does not comprise a salt.

The invention also provides a method of making the immunogenic composition or vaccine of the invention comprising the step of mixing antigens of the invention with a pharmaceutically acceptable excipient or carrier.

Immunogenic compositions comprise an immunologically effective amount of the protein or conjugate (e.g. bioconjugate) of the invention, as well as any other components. By "immunologically effective amount", it is meant that the administration of that amount to an individual, either as a single dose or as part of a series is effective for treatment or prevention. This amount varies depending on the health and physical condition of the individual to be treated, age, the degree of protection desired, the formulation of the vaccine and other relevant factors. It is expected that the amount will fall in a relatively broad range that can be determined through routine trials.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The immunogenic compositions and vaccines of the invention can be included in a container, pack, or dispenser together with instructions for administration. The invention provides a kit comprising (i) a first container comprising an immunogenic composition or a vaccine of the invention; and (ii) a second container comprising an adjuvant as described herein.

Adjuvants

In an embodiment, the immunogenic compositions of the invention comprise, or are administered in combination with, an adjuvant. The adjuvant for administration in combination with an immunogenic composition of the invention may be administered before, concomitantly with, or after administration of said immunogenic composition or vaccine. In an embodiment, said adjuvant is mixed with the immunogenic composition before administration.

Adjuvants can enhance an immune response by several mechanisms including, e.g. lymphocyte recruitment, stimulation of B and/or T cells, and stimulation of macrophages. In an embodiment, the adjuvant is selected to be a preferential inducer of either a TH1 or a TH2 type of response, preferably a TH1 type response. High levels of Th1-type cytokines tend to favour the induction of cell mediated immune responses to a given antigen, whilst high levels of Th2-type cytokines tend to favour the induction of humoral immune responses to the antigen. It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4+ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of 11-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); MPL, e.g. 3D-MPL and the saponin QS21 in a liposome, for example a liposome comprising cholesterol and DPOC; and a combination of monophosphoryl lipid A, for example 3-de-O-acylated monophosphoryl lipid A, together with either an Aluminium salt (for instance Aluminium phosphate or Aluminium hydroxide) or an oil-in-water emulsion. In such combinations, the antigen and 3D-MPL may be contained in the same particulate structures, allowing for more efficient delivery of antigenic and immunostimulatory signals. Studies have shown that 3D-MPL is able to further enhance the immunogenicity of an Alum-adsorbed antigen (Thoelen et al. Vaccine (1998) 16:708-14; EP 689454-B1).

In one embodiment the adjuvant comprises both a TLR4 agonist and immunologically active saponin. In an embodiment, the TLR4 agonist is a lipopolysaccharide. Suitably the saponin comprises an active fraction of the saponin derived from the bark of *Quillaja Saponaria Molina*, such as QS21. Suitably the lipopolysaccharide is a Lipid-A derivative such as 3D-MPL. In a specific embodiment, the lipopolysaccharide is 3D-MPL and the immunologically active saponin is QS21. In an embodiment, said adjuvant composition comprises a lipopolysaccharide and immunologically active saponin in a liposomal formulation. Suitably in one form of this embodiment, the adjuvant consists essentially of 3D-MPL and QS21, with optionally sterol which is preferably cholesterol.

Liposome size may vary from 30 nm to several um depending on the phospholipid composition and the method used for their preparation. In particular embodiments of the invention, the liposome size will be in the range of 50 nm to 500 nm and in further embodiments 50 nm to 200 nm. Optimally, the liposomes should be stable and have a diameter of ~100 nm to allow sterilisation by filtration.

Other TLR4 agonists which may be of use in the present invention include Glucopyranosyl Lipid Adjuvant (GLA) such as described in WO2008/153541 or WO2009/143457 or the literature articles Coler R N et al. (2011) Development and Characterization of Synthetic Glucopyranosyl Lipid Adjuvant System as a Vaccine Adjuvant. PLoS ONE 6(1):

e16333. doi:10.1371/journal.pone.0016333 and Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal-.pone.0041144. WO2008/153541 or WO2009/143457 are incorporated herein by reference for the purpose of defining TLR4 agonists which may be of use in the present invention.

4'-monophosporyl lipid A (MPL), which may be obtained by the acid hydrolysis of LPS extracted from a deep rough mutant strain of gram-negative bacteria, retains the adjuvant properties of LPS while demonstrating a toxicity which is reduced by a factor of more than 1000 (as measured by lethal dose in chick embryo eggs) (Johnson et al. 1987 Rev. Infect. Dis. 9 Suppl:S512-S516). LPS is typically refluxed in mineral acid solutions of moderate strength (e.g. 0.1 M HCl) for a period of approximately 30 minutes. This process results in dephosphorylation at the 1 position, and decarbohydration at the 6' position, yielding MPL.

3-O-deacylated monophosphoryl lipid A (3D-MPL), which may be obtained by mild alkaline hydrolysis of MPL, has a further reduced toxicity while again maintaining adjuvanticity, see U.S. Pat. No. 4,912,094 (Ribi Immunochemicals). Alkaline hydrolysis is typically performed in organic solvent, such as a mixture of chloroform/methanol, by saturation with an aqueous solution of weak base, such as 0.5 M sodium carbonate at pH 10.5. Further information on the preparation of 3D-MPL is available in, for example, U.S. Pat. No. 4,912,094 and WO02/078637 (Corixa Corporation).

*Quillaja* saponins are a mixture of triterpene glycosides extracted from the bark of the tree *Quillaja saponaria*. Crude saponins have been extensively employed as veterinary adjuvants. Quil-A is a partially purified aqueous extract of the *Quillaja* saponin material. Quil A is a saponin preparation isolated from the South American tree *Quillaja Saponaria Molina* and was first described by Dalsgaard et al. in 1974 ("Saponin adjuvants", Archiv. für die gesamte Virusforschung, Vol. 44, Springer Verlag, Berlin, p243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria Molina*, which induces CD8+ cytotoxic T cells (CTLs), Th1 cells and a predominant IgG2a antibody response and is a preferred saponin in the context of the present invention. QS21 is a HPLC purified non toxic fraction of Quil A and its method of production is disclosed (as QA21) in U.S. Pat. No. 5,057,540. Preferably the adjuvant contains QS21 in substantially pure form, that is to say, the QS21 is at least 90% pure, for example at least 95% pure, or at least 98% pure.

Adjuvants containing combinations of lipopolysaccharide and *Quillaja* saponins have been disclosed previously, for example in EP0671948. This patent demonstrated a strong synergy when a lipopolysaccharide (3D-MPL) was combined with a *Quillaja* saponin (QS21). Good adjuvant properties may be achieved with combinations of lipopolysaccharide and *quillaja* saponin as immunostimulants in an adjuvant composition even when the immunostimulants are present at low amounts in a human dose, as described in WO2007/068907.

In a specific embodiment, QS21 is provided in its less reactogenic composition where it is quenched with an exogenous sterol, such as cholesterol for example. Several particular forms of less reactogenic compositions wherein QS21 is quenched with an exogenous cholesterol exist. In a specific embodiment, the saponin/sterol is in the form of a liposome structure (WO 96/33739, Example 1). In this embodiment the liposomes suitably contain a neutral lipid, for example phosphatidylcholine, which is suitably non-crystalline at room temperature, for example egg yolk phosphatidylcholine, dioleoyl phosphatidylcholine (DOPC) or dilauryl phosphatidylcholine. The liposomes may also contain a limited amount of a charged lipid which increases the stability of the liposome-saponin structure for liposomes composed of saturated lipids. In these cases the amount of charged lipid is suitably 1-20% w/w, preferably 5-10% w/w of the liposome composition. Suitable examples of such charged lipids include phosphatidylglycerol and phosphatidylserine. Suitably, the neutral liposomes will contain less than 5% w/w charged lipid, such as less than 3% w/w or less than 1% w/w. The ratio of sterol to phospholipid is 1-50% (mol/mol), suitably 20-25%.

Suitable sterols include β-sitosterol, stigmasterol, ergosterol, ergocalciferol and cholesterol. In one particular embodiment, the adjuvant composition comprises cholesterol as sterol. These sterols are well known in the art, for example cholesterol is disclosed in the Merck Index, 11th Edn., page 341, as a naturally occurring sterol found in animal fat.

Where the active saponin fraction is QS21, the ratio of QS21: sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol.

3D-MPL is sold under the name MPL by GlaxoSmithKline Biologicals S. A. and is referred throughout the document as MPL or 3D-MPL. see, for example, U.S. Pat. Nos. 4,436,727; 4,877,611; 4,866,034 and 4,912,094. 3D-MPL primarily promotes CD4+ T cell responses with an IFN-g (Th1) phenotype. 3D-MPL can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3D-MPL is used. Small particle 3D-MPL has a particle size such that it may be sterile-filtered through a 0.22 μm filter. Such preparations are described in WO 94/21292.

Suitable adjuvant compositions are those wherein liposomes are initially prepared without MPL (as described in WO 96/33739), and MPL is then added, suitably as small particles of below 100 nm particles or particles that are susceptible to sterile filtration through a 0.22 μm membrane. The MPL is therefore not contained within the vesicle membrane (known as MPL out). Compositions where the MPL is contained within the vesicle membrane (known as MPL in) also form an aspect of the invention. The antigen can be contained within the vesicle membrane or contained outside the vesicle membrane.

For a maximum batch size of 12 g, MPL liquid bulk preparation is carried over in sterile glass containers. The dispersion of MPL consists of the following steps: suspend the MPL powder in water for injection: disaggregate any big aggregates by heating (thermal treatment; reduce the particle size between 100 nm and 200 nm by microfluidisation; prefilter the preparation on a Sartoclean Pre-filter unit, 0.8/0.65 μm; sterile filter the preparation at room temperature (Sartobran P unit, 0.22 μm).

MPL powder is lyophilised by microfluidisation resulting in a stable colloidal aqueous dispersion (MPL particles of a size susceptible to sterile filtration). The MPL lyophilised powder is dispersed in water for injection in order to obtain a coarse 10 mg/ml suspension. The suspension then undergoes a thermal treatment under stirring. After cooling to room temperature, the microfluidisation process is started in order to decrease the particle size. Microfluidisation is conducted using Microfluidics apparatus M110EH, by continuously circulating the dispersion through a microfluidisation interaction chamber, at a defined pressure for a minimum amount of passages (number of cycles: $n_{min}$). The microfluidisation duration, representing the number of cycles, is calculated on basis of the measured flow rate and the dispersion volume. On a given equipment at a given pressure, the resulting flow rate may vary from one interaction chamber to another, and throughout the lifecycle of a particular interaction chamber. In the present example the interaction chamber used is of the type F20Y Microfluidics. As the microfluidisation efficiency is linked to the couple pressure—flow rate, the processing time may vary from one batch to another. The time required for 1 cycle is calculated on basis of the flow rate. The flow rate to be considered is the flow rate measured with water for injection just before introduction of MPL into the apparatus. One cycle is defined as the time (in minutes) needed for the total volume of MPL to pass once through the apparatus. The time needed to obtain n cycles is calculated as follows:

$n \times$ quantity of MPL to treat (ml)/flow rate (ml/min)

The number of cycles is thus adapted accordingly. Minimum amount of cycles to perform ($n_{min}$) are described for the preferred equipment and interaction chambers used. The total amount of cycles to run is determined by the result of a particle size measurement performed after $n_{min}$ cycles. A particle size limit ($d_{lim}$) is defined, based on historical data. The measurement is realized by photon correlation spectroscopy (PCS) technique, and $d_{lim}$ is expressed as an unimodal result ($Z_{average}$). Under this limit, the microfluidisation can be stopped after $n_{min}$ cycles. Above this limit, microfluidisation is continued until satisfactory size reduction is obtained, for maximum another 50 cycles.

If the filtration does not take place immediately after microfluidisation, the dispersed MPL is stored at +2 to +8° C. awaiting transfer to the filtration area.

After microfluidisation, the dispersion is diluted with water for injection, and sterile filtered through a 0.22 µm filter under laminal flow. The final MPL concentration is 1 mg/ml (0.80-1.20 mg/ml).

In the process of production of liposomes containing MPL the DOPC (Dioleyl phosphatidylcholine), cholesterol and MPL are dissolved in ethanol. A lipid film is formed by solvent evaporation under vacuum. Phosphate Buffer Saline (9 mM $Na_2HPO_4$, 41 mM $KH_2PO_4$, 100 mM NaCl) at pH 6.1 is added and the mixture is submitted to prehomogenization followed by high pressure homogenisation at 15,000 psi (around 15 to 20 cycles). This leads to the production of liposomes which are sterile filtered through a 0.22 µm membrane in an aseptic (class 100) area. The sterile product is then distributed in sterile glass containers and stored in a cold room (+2 to +8° C.).

In this way the liposomes produced contain MPL in the membrane (the "MPL in" embodiment of WO 96/33739).

QS21 is added in aqueous solution to the desired concentration.

The adjuvant AS01 comprises 3D-MPL and QS21 in a quenched form with cholesterol, and was made as described in WO 96/33739. In particular the AS01 adjuvant was prepared essentially as Example 1.1 of WO 96/33739. The $AS01_B$ adjuvant comprises: liposomes, which in turn comprise dioleoyl phosphatidylcholine (DOPC), cholesterol and 3D MPL [in an amount of 1000 µg DOPC, 250 µg cholesterol and 50 µg 3D-MPL, each value given approximately per vaccine dose], QS21 [50 µg/dose], phosphate NaCl buffer and water to a volume of 0.5 ml.

The $AS01_E$ adjuvant comprises the same ingredients as $AS01_B$ but at a lower concentration in an amount of 500 µg DOPC, 125 µg cholesterol, 25 µg 3D-MPL and 25 µg QS21, phosphate NaCl buffer and water to a volume of 0.5 ml.

In a preferred embodiment, the adjuvant used in the present invention is $AS01_E$.

Method of Administration

In one aspect, the immunogenic composition or vaccine of the invention is administered by the intramuscular delivery route. Intramuscular administration may be to the thigh or the upper arm. Injection is typically via a needle (e.g. a hypodermic needle). A typical intramuscular dose is 0.5 ml, as described below.

Dosage

The amount of conjugate antigen in each immunogenic composition or vaccine dose is selected as an amount which induces an immunoprotective response without significant, adverse side effects in typical vaccines. Such amount will vary depending upon which specific immunogen is employed and how it is presented. The content of each protein antigen will typically be in the range 1-200 µg, suitably 1-100 µg, suitably 5-50 µg. The content of each saccharide antigen will typically be in the range 0.1-50 µg, suitably 0.1-10 µg, suitably 1-5 µg.

A dose which is in a volume suitable for human use is generally between 0.25 and 1.5 ml, although, for administration to the skin a lower volume of between 0.05 ml and 0.2 ml may be used. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the pediatric population, a human dose may be less than 0.5 ml such as between 0.25 and 0.5 ml.

Where the immunogenic composition comprises an adjuvant comprising 3D-MPL and QS21, QS21 and 3D-MPL are preferably present in the same final concentration per human dose of the immunogenic composition. In an embodiment, the human dose of the immunogenic composition comprises 3D-MPL at a level of around 25 µg, for example between 20-30 µg, suitably between 21-29 µg or between 22 and 28 µg or between 23 and 27 µg or between 24 and 26 µg, or 25 µg. In an embodiment, the human dose of the immunogenic composition comprises QS21 at a level of around 25 µg, for example between 20-30 µg, suitably between 21-29 µg or between 22 and 28 µg or between 23 and 27 µg or between 24 and 26 µg, or 25 µg. In a preferred embodiment, a human dose of immunogenic composition comprises a final level of 25 µg of 3D-MPL and 25 µg of QS2. In another embodiment, a human dose of immunogenic composition comprises a final level of 50 µg of 3D-MPL and 50 µg of QS21.

Where the immunogenic composition is for use in combination with an adjuvant composition comprising 3D-MPL and QS21, QS21 and 3D-MPL are preferably present in the same final concentration per human dose of the adjuvant composition. In an embodiment, the human dose of the adjuvant composition comprises 3D-MPL at a level of around 25 µg, for example between 20-30 µg, suitably between 21-29 µg or between 22 and 28 µg or between 23 and 27 µg or between 24 and 26 µg, or 25 µg. In an embodiment, an adjuvant composition in a volume which is suitable for a human dose which human dose of the adjuvant composition comprises QS21 at a level of around 25 µg, for example between 20-30 µg, suitably between 21-29 µg or between 22 and 28 µg or between 23 and 27 µg or between 24 and 26 µg, or 25 µg. In a preferred embodiment, a human dose of adjuvant composition comprises a final level of 25 µg of 3D-MPL and 25 µg of QS21. In another embodiment, a human dose of adjuvant composition comprises a final level of 50 µg of 3D-MPL and 50 µg of QS21.

Where the adjuvant is in a liquid form to be combined with a liquid form of an antigenic composition, the adjuvant composition will be in a human dose suitable volume which is approximately half of the intended final volume of the human dose, for example a 360 µl volume for an intended human dose of 0.7 ml, or a 250 µl volume for an intended human dose of 0.5 ml. The adjuvant composition is diluted when combined with the antigen composition to provide the final human dose of vaccine. The final volume of such dose will of course vary dependent on the initial volume of the adjuvant composition and the volume of antigen composition added to the adjuvant composition. In an alternative embodiment, liquid adjuvant is used to reconstitute a lyophilised antigen composition. In this embodiment, the human dose suitable volume of the adjuvant composition is approximately equal to the final volume of the human dose. The liquid adjuvant composition is added to the vial containing the lyophilised antigen composition. The final human dose can vary between 0.5 and 1.5 ml. In a particular embodiment the human dose is 0.5 ml.

Prophylactic and Therapeutic Uses

The present invention provides methods of treating and/or preventing bacterial infections of a subject comprising administering to the subject an immunogenic composition or vaccine of the invention. In a specific embodiment, the immunogenic composition of the invention is used in the prevention of infection of a subject (e.g. human subjects) by a staphylococcal bacterium. *S. aureus* infects various mammals (including cows, dogs, horses, and pigs), but the preferred subject for use with the invention is a human.

In a specific embodiment, the immunogenic composition of the invention is used to treat or prevent an infection by *Staphylococcus* species, in particular *S. aureus*. For example, the immunogenic composition of the invention may be used to prevent against *S. aureus* infection, including a nosocomial infection.

Also provided are methods of inducing an immune response in a subject against a staphylococcal bacterium, in particular *S. aureus*, comprising administering to the subject an immunogenic composition or vaccine of the invention. In one embodiment, said subject has bacterial infection at the time of administration. In another embodiment, said subject does not have a bacterial infection at the time of administration. The immunogenic composition or vaccine of the invention can be used to induce an immune response against *Staphylococcus* species, in particular *S. aureus*.

Also provided are methods of inducing the production of opsonophagocytic antibodies in a subject against a staphylococcal bacterium, in particular *S. aureus*, comprising administering to the subject an immunogenic composition or vaccine of the invention. In one embodiment, said subject has bacterial infection at the time of administration. In another embodiment, said subject does not have a bacterial infection at the time of administration.

Also provided are methods of inducing the production of antibodies able to neutralise or reduce the activity of staphylococcal Hla, ClfA and/or SpA in a subject, comprising administering to the subject an immunogenic composition or vaccine of the invention. Said Hla activity may be ability to lyse human erythrocytes (haemolysis). Said ClfA activity may be ability to bind to human fibrinogen. Said SpA activity may be ability to bind to Fcγ of immunoglobulin (Ig) and to the Fab portion of $V_H3$-type B cell receptors.

Also provided is a method of immunising a human host against staphylococcal infection, particularly *S. aureus* infection, comprising administering to the host an immunogenic composition or vaccine of the invention.

Also provided is a method of inducing an immune response to a staphylococcal bacterium, in particular *S. aureus*, in a subject, the method comprising administering a therapeutically or prophylactically effective amount of the an immunogenic composition or vaccine of the invention.

Also provided is an immunogenic composition or vaccine of the invention for use in a method of treatment and/or prevention of disease, for example for use a method of treatment or prevention of a disease caused by staphylococcal infection, particularly *S. aureus* infection.

Also provided is an immunogenic composition or vaccine of the invention in the manufacture of a medicament for the treatment or prevention of a disease caused by staphylococcal infection, particularly *S. aureus* infection.

Also provided is the use of an immunogenic composition or vaccine of the invention for the manufacture of a medicament for use in a method of treatment and/or prevention of disease, for example for use a method of treatment or prevention of a disease caused by staphylococcal infection, particularly *S. aureus* infection.

Also provided is a pharmaceutical for treatment or prevention of staphylococcal infection, particularly *S. aureus* infection, comprising an immunogenic composition or vaccine of the invention.

Also provided is an immunogenic composition or vaccine of the invention for use in a method of inducing an immune response in a subject against a staphylococcal bacterium, in particular *S. aureus*.

Also provided is an immunogenic composition or vaccine of the invention for use in a method of inducing the production of opsonophagocytic antibodies in a subject against a staphylococcal bacterium, in particular *S. aureus*.

Also provided is an immunogenic composition or vaccine of the invention for use in a method of inducing the production of antibodies able to neutralise or reduce the activity of staphylococcal Hla, ClfA and/or SpA in a subject, comprising administering to the subject an immunogenic composition or vaccine of the invention. Said Hla activity may be ability to lyse human erythrocytes (haemolysis). Said ClfA activity may be ability to bind to human fibrinogen. Said SpA activity may be ability to bind to Fcγ of immunoglobulin (Ig) and to the Fab portion of $V_H3$-type B cell receptors.

All references or patent applications cited within this patent specification are incorporated by reference herein.

Aspects of the invention are summarised in the subsequent numbered paragraphs:

1. An immunogenic composition comprising
   a. a ClfA antigen;
   b. a Hla antigen;
   c. a SpA antigen; and
   d. a staphylococcal capsular polysaccharide.
2. An immunogenic composition according to paragraph 1, wherein the capsular polysaccharide is conjugated to a carrier protein.

3. An immunogenic composition according to paragraph 1 or paragraph 2, wherein the capsular polysaccharide is a *S. aureus* serotype 5 and/or type 8 capsular polysaccharide.

4. An immunogenic composition according to any one of paragraphs 1 to 3, wherein the capsular polysaccharide is conjugated to one of the antigens (a)-(c) of paragraph 1.

5. An immunogenic composition according to any one of paragraphs 1 to 4, wherein the composition comprises a *S. aureus* serotype 5 capsular polysaccharide and a type 8 capsular polysaccharide.

6. An immunogenic composition according to any one of paragraphs 1 to 5, wherein the composition comprises a *S. aureus* serotype 5 capsular polysaccharide conjugated to a Hla antigen and/or a type 8 capsular polysaccharide conjugated to a ClfA antigen.

7. An immunogenic composition according to any one of paragraphs 1 to 6, wherein
   a. the ClfA antigen is a ClfA protein comprising the amino acid sequence of SEQ ID NO. 2 or an amino acid sequence at least 80%, 85%, 90%, 92%, 95%, 96%, 97%, 98% or 99% identical to SEQ ID NO. 2, or immunogenic fragment thereof;
   b. the Hla antigen is a Hla protein having the amino acid sequence of SEQ ID NO. 3 or an amino acid sequence at least 80%, 85%, 90%, 92%, 95%, 96%, 97%, 98% or 99% identical to SEQ ID NO. 3 or immunogenic fragment thereof; and/or
   c. the SpA antigen is a SpA protein having an amino acid sequence of SEQ ID NO. 13 or SEQ ID NO: 26 or an amino acid sequence at least 80%, 85%, 90%, 92%, 95%, 96%, 97%, 98% or 99% identical to SEQ ID NO. 13 or SEQ ID NO: 26, or immunogenic fragment thereof.

8. A composition according to any of paragraphs 1 to 7, wherein the ClfA antigen comprises at least one amino acid substitution selected from P116 to S and Y118 to A with reference to the amino acid sequence of SEQ ID NO. 2 (or an equivalent position in an amino acid sequence at least 80%, 85%, 90%, 92%, 95%, 96%, 97%, 98% or 99% identical to SEQ ID NO. 2), optionally comprising the sequence of any one of SEQ ID NOs 5-7 or 32.

9. An immunogenic composition according to paragraph 7 or paragraph 8, wherein the ClfA antigen comprises one or more PglB consensus sequence(s) selected from: D/E-X-N-Z-S/T (SEQ ID NO. 28) and K-D/E-X-N-Z-S/T-K (SEQ ID NO. 29), wherein X and Z are independently any amino acid apart from proline.

10. An immunogenic composition according to paragraph 9, wherein said consensus sequence has been added at, or substituted for, one or more amino acids between amino acid residues 313-342 of SEQ ID NO: 2, optionally substituted for the amino acid at position 1337, or at an equivalent position within an amino acid sequence at least 80%, 85%, 90%, 92%, 95%, 96%, 97%, 98% or 99% identical to SEQ ID NO: 2.

11. An immunogenic composition according to paragraph 9 or paragraph 10, wherein X is Q (glutamine) and Z is A (alanine) (e.g. K-D-Q-N-A-T-K, SEQ ID NO: 31.

12. An immunogenic composition according to paragraph 11, wherein the ClfA antigen comprises or consists of the sequence of SEQ ID NO: 7 or SEQ ID NO: 32.

13. An immunogenic composition according to any one of paragraphs 1 to 12, wherein the Hla antigen comprises an amino acid substitution at position H35 of SEQ ID NO. 3 or at an equivalent position within an amino acid sequence at least 80%, 85%, 90%, 92%, 95%, 96%, 97%, 98% or 99% identical to SEQ ID NO. 3, wherein said amino acid substitution is optionally H to L.

14. An immunogenic composition according to any one of paragraphs 1 to 13, wherein the Hla antigen comprises one or more PglB consensus sequence(s) selected from: D/E-X-N-Z-SIT (SEQ ID NO. 28) and K-D/E-X-N-Z-SIT-K (SEQ ID NO. 29), wherein X and Z are independently any amino acid apart from proline.

15. An immunogenic composition according to paragraph 14, wherein said consensus sequence has been added at, or substituted for, one or more amino acids of the amino acid sequence of SEQ ID NO. 3 or an amino acid sequence at least 80%, 85%, 90%, 92%, 95%, 96%, 97%, 98% or 99% identical to SEQ ID NO. 3.

16. An immunogenic composition according to paragraph 14, wherein said consensus sequence has been substituted for the amino acid at position K131 of SEQ ID NO. 3 of SEQ ID NO: 3, or at an equivalent position within an amino acid sequence at least 80%, 85%, 90%, 92%, 95%, 96%, 97%, 98% or 99% identical to SEQ ID NO: 3.

17. An immunogenic composition according to any one of paragraphs 14 to 16, wherein X is Q (glutamine) and Z is R (arginine) (e.g. K-D-Q-N-R-T-K (SEQ ID NO 30)

18. An immunogenic composition according to paragraph 17, wherein the Hla antigen comprises or consists of the sequence of SEQ ID NO: 11 or SEQ ID NO 12.

19. The immunogenic composition according to any one of paragraphs 1 to 18, wherein the SpA antigen comprises (a) one or more amino acid substitutions in a $V_H3$-binding sub-domain of domain E, D, A, B or C that disrupts or decreases binding to $V_H3$, and (b) one or more amino acid substitutions in an IgG Fc binding sub-domain of domain E, D, A, B or C that disrupts or decreases binding to IgG Fc.

20. An immunogenic composition according to any one of paragraphs 1 to 19, wherein the SpA antigen comprises (i) a domain E with an amino acid substitution at the amino acid positions 34 and 35 of SEQ ID NO: 14 or at an equivalent position within an amino acid sequence at least 80%, 85%, 90%, 92%, 95%, 96%, 97%, 98% or 99% identical to SEQ ID NO: 14; a domain D with an amino acid substitution at amino acid positions 39 and 40 of SEQ ID NO: 15 or at an equivalent position within an amino acid sequence at least 80%, 85%, 90%, 92%, 95%, 96%, 97%, 98% or 99% identical to SEQ ID NO: 15; a domain A with an amino acid substitution at positions 36 and 37 of SEQ ID NO: 16 or at an equivalent position within an amino acid sequence at least 80%, 85%, 90%, 92%, 95%, 96%, 97%, 98% or 99% identical to SEQ ID NO: 16; a domain B with an amino acid substitution at positions amino acid positions 36 and 37 of SEQ ID NO: 17 or at an equivalent position within an amino acid sequence at least 80%, 85%, 90%, 92%, 95%, 96%, 97%, 98% or 99% identical to SEQ ID NO: 17, and/or a domain C with an amino acid substitution at positions amino acid positions 36 and 37 of SEQ ID NO: 18 or at an equivalent position within an amino acid sequence at least 80%, 85%, 90%, 92%, 95%, 96%, 97%, 98% or 99% identical to SEQ ID NO: 18; and/or (ii) comprises a domain E with an amino acid substitution at amino acid positions 7 and 8 of SEQ ID NO: 14 or at an equivalent position within an amino acid sequence at least 80%, 85%, 90%, 92%, 95%, 96%, 97%, 98% or 99% identical to SEQ ID NO: 14; a domain D with an amino acid substitution at amino acid positions 12 and 13 of SEQ ID NO: 15 or at an equivalent position within an amino acid sequence at least 80%, 85%, 90%, 92%, 95%, 96%, 97%, 98% or 99% identical to SEQ ID NO: 15; a domain A with an amino acid substitution at positions 9 and 10 of SEQ ID NO: 16 or at an equivalent position within an amino acid sequence at least 80%, 85%, 90%, 92%, 95%, 96%, 97%, 98% or 99% identical to SEQ ID NO: 16; a domain B with an amino acid substitution at positions amino acid positions 9 and 10 of SEQ ID NO: 17 or at an equivalent position within an amino acid sequence at least 80%, 85%, 90%, 92%, 95%, 96%, 97%, 98% or 99% identical to SEQ ID NO: 17, and/or a domain C with an amino acid substitution at positions amino acid positions 9 and 10 of SEQ ID NO: 18 or at an equivalent position within an amino acid sequence at least 80%, 85%, 90%, 92%, 95%, 96%, 97%, 98% or 99% identical to SEQ ID NO: 18.

21. An immunogenic composition according to paragraph 20, wherein said amino acid substitutions are substitution of lysine for glutamine and/or substitution of alanine for aspartic acid.

22. An immunogenic composition of any one of paragraphs 1 to 21, wherein the SpA antigen comprises a domain D with an amino acid substitution at amino acid positions 4 and 5 of SEQ ID NO: 15. or at an equivalent position within an amino acid sequence at least 80%, 85%, 90%, 92%, 95%, 96%, 97%, 98% or 99% identical to SEQ ID NO: 15

23. An immunogenic composition according to paragraph 22, wherein said amino acid substitution is glutamine to lysine and/or glutamine to arginine, e.g. QQ to KR.

24. An immunogenic composition according to any one of paragraphs 1 to 23, wherein said SpA antigen comprises an amino acid sequence of SEQ ID NOs: 19-23, 26 or 27, or an amino acid sequence at least 80%, 85%, 90%, 92%, 95%, 96%, 97%, 98% or 99% identical to SEQ ID NOs: 19-23, 26 or 27.

25. An immunogenic composition according to any one of paragraphs 1 to 24, wherein the immunogenic composition comprises (i) a ClfA antigen comprising the amino acid sequence of SEQ ID NO: 7 or SEQ ID NO: 32; (ii) a Hla antigen comprising the amino acid sequence sequence of SEQ ID NO: 11 or SEQ ID NO: 12; (iii) an SpA antigen comprising the amino acid sequence of SEQ ID NO: 27; (iv) a S. aureus serotype 5 capsular polysaccharide, and (v) a S. aureus serotype type 8 capsular polysaccharide.

26. An immunogenic composition according to paragraph 25, wherein the ClfA antigen is conjugated to the S. aureus serotype type 8 capsular polysaccharide, and the Hla antigen is conjugated to the S. aureus serotype 5 capsular polysaccharide.

27. An immunogenic composition according to paragraph 26, wherein said ClfA-CP8 and Hla-CP5 conjugates are bioconjugates.

28. An immunogenic composition according to any one of paragraphs 1 to 27, which composition comprises an adjuvant.

29. An immunogenic composition according to paragraph 28, wherein the adjuvant comprises a saponin and a lipopolysaccharide.

30. An immunogenic composition according to paragraph 29, wherein the adjuvant comprises a saponin, a lipopolysaccharide in a liposomal formation.

31. An immunogenic composition according to paragraph 29 or paragraph 30, further comprising a sterol.

32. An immunogenic composition according to paragraph any one of paragraphs 29 to 31, wherein the saponin is an immunologically active saponin fraction derived from the bark of Quillaja Saponaria Molina.

33. An immunogenic composition according to paragraph 32, wherein the saponin is QS21.

34. An immunogenic composition according to any one of paragraphs 29 to 33, wherein the lipopolysaccharide is a lipid A derivative.

35. An immunogenic composition according to paragraph 34, wherein the lipopolysaccharide is 3D-MPL.

36. An immunogenic composition according to any one of paragraphs 31 to 35, wherein the sterol is cholesterol.

37. An immunogenic composition according to any one of paragraphs 29 to 36, wherein the immunogenic composition comprises QS21 at a level of 25 µg per human dose.

38. An immunogenic composition according to any one of paragraphs 29 to 37, wherein the immunogenic composition comprises 3D-MPL at a level of 25 µg per human dose.

39. A vaccine comprising an immunogenic composition according to any one of paragraphs 1 to 27 and a pharmaceutically acceptable excipient or carrier.

40. A vaccine comprising an immunogenic composition according to any one of paragraphs 28 to 38 and a pharmaceutically acceptable excipient or carrier.

41. An immunogenic composition according to any one of paragraphs 1 to 27, or a vaccine according to paragraph 39, for use in a method of prevention or treatment of staphylococcal infection, wherein said composition is administered in combination with an adjuvant.

42. An immunogenic composition or vaccine for use according to paragraph 41, wherein the immunogenic composition is mixed with the adjuvant before administration to a subject.

43. An immunogenic composition or vaccine for use according to paragraph 41 or paragraph 42, wherein the adjuvant is as defined in any one of paragraphs 29 to 36.

44. An immunogenic composition or vaccine for use according to paragraph 43, wherein the adjuvant comprises 3D-MPL at a level of 25 µg per human dose and QS21 at a level of 25 µg per human dose.

45. A kit comprising (i) a first container comprising an immunogenic composition of any one of paragraphs 1 to 27 or a vaccine according to paragraph 39; and (ii) a second container comprising an adjuvant.

46. A kit according to paragraph 45, wherein the adjuvant is as defined in any one of paragraphs 29 to 36.

47. A kit according to paragraph 46, wherein the adjuvant comprises 3D-MPL at a level of 25 µg per human dose and QS21 at a level of 25 µg per human dose.

48. A method of prevention or treatment of staphylococcal infection, comprising administering to a subject in need thereof an immunogenic composition according to any one of paragraphs 1 to 27 or a vaccine according to paragraph 39.

49. A method according to paragraph 48, further comprising administering an adjuvant to said subject.

50. A method according to paragraph 49, wherein said adjuvant is administered concomitantly with the immunogenic composition.

51. A method according to paragraph 49 or paragraph 50, wherein the adjuvant is as defined in any one of paragraphs 29 to 36.

52. A method of prevention or treatment of staphylococcal infection, comprising administering to a subject in need thereof an immunogenic composition according to any one of paragraphs 28 to 38 or a vaccine according to paragraph 40.

53. A method of making an immunogenic composition or vaccine according to any one of paragraphs, comprising the steps of mixing antigens, and optionally an adjuvant, with a pharmaceutically acceptable excipient.

EXAMPLES

Example 1: Vaccine Composition and Formulation

Vaccine Components

Bioconjugates of CP5, containing 6 to 20 repeating units, linked to $Hla_{mut}$ containing one glycosylation site, H35L/H48C/G122C mutations and a C-terminal HRHR tag (SEQ ID NO: 12, expressed using a FlgL signal sequence) were produced using fed-batch fermentation of E. coli cells transformed with the plasmids encoding the S. aureus capsular polysaccharide CP5, the S. aureus carrier protein $Hla_{H35L-H48C-G122C}$ carrying a glycosylation site at position 131 and a C-terminal histidine-arginine-histidine-arginine tag, and Campylobacter jejuni oligosaccharyltransferase $PglB_{CuO\ N311V-K482R-D483H-A669V}$.

Bioconjugates of CP8, 5 to 16 repeating units, linked to $ClfA_{mut}$ comprising the ClfA N2/N3 domains with one glycosylation site and P116S/Y118A mutations (SEQ ID NO: 7) were produced by fed-batch fermentation of E. coli cells expressing $PglB_{CuO\ N311V-K482R-D483H-A669V}$ and S. aureus CP8 (W3110 waaL::$pglB_{CuO\ N311V-K482R-D483H-A669V}$; O16::O11_wbjB-wbpM; ΔrmlB-wecG; wecA-wzzE::CP8_p2636(CCW)_Cat) and transformed with the plasmid encoding $ClfA_{mut}$.

Bioconjugates were tested for stability in different formulations The stability of three different formulations for each batch was tested at −80° C. (long term), +4° C. (intermediate) and +25° C. up to 3 months by applying part of the analytical panel reported in the table above to evaluate content, purity, aggregation, degradation with regards to protein and polysaccharide stability.

CP5-Hla and CP8-ClfA bioconjugates were stable at 4° C. and −80° C. for at least 3 months and up to 3 months at 25° C.

A SpA variant ($SpA_{KR-KKAA}$, herein indicated as $SpA_{mut}$ and comprising the sequence of SEQ ID No: 27, described in WO2015/144653) comprising the IgG binding portion (IgG binding domains EDABC) harbouring amino acid substitutions at four key residues in each of the five IgBD (glutamine and aspartate changed into lysine and alanine respectively), which highly impaired IgG and IgM binding, as well as two additional immunoglobulin binding residues corresponding to Q70 and Q71 of the IgG binding portion (Q96 and Q97 of the full-length protein) which were mutated into lysine 70 and arginine 71 respectively (K70 and R71). $SpA_{mut}$ was shown to have no detectable affinity to human IgG and IgM by surface plasmon resonance experiments, making the molecule safer for vaccine usage. $SpA_{mut}$ was expressed in recombinant form by bacterial batch fermentation using a commercial Escherichia coli BL21 (DE3) strain.

Accelerated stability studies were performed by using SDS-PAGE and SE-UPLC for the analysis of the protein after storage for 3, 10 and 30 days at 4° C., at RT and at 37° C. in four suitable formulation buffers.

$SpA_{mut}$ was stable at 4° C. up to 3 months, stable at 25° C. up to 10 days, and stable at 37° C. up to 4 days.

Vaccine Formulation

Formulations for mouse immunisation studies were prepared unadjuvanted and adjuvanted with $AS01_E$ (3D-MPL+QS21 in a liposome composition, as described above) and Alum/TLR7 (TLR7 agonist adsorbed to AlOH, as described in WO2011/027222, Example 20, WO2012/031140 and Bagnoli et al, PNAS, 2015, 112: 3680-3685). The three components (CP5-Hla, CP8-ClfA, $SpA_{mut}$) were formulated in the same vial at a concentration of 200 µg/ml for each component (two fold concentrated, here referred as 2×, with respect to final high dose), based on protein content. To obtain the final different formulations, vial 2× with the three mixed components were reconstituted with formulation buffer (10 mM $NaH_2PO_4$, 150 mM NaCl pH 6.5) or adjuvants (two fold concentrated, with respect to adjuvant final dose) through a bed-side mixing approach prior to immunisation. High protein dosage was reached by reconstituting one volume of vial 2× with an equivalent volume of $AS01_E$ (two fold concentrated compared to $AS01_E$), or Alum/TLR7 (two fold concentrated, Alum/TLR7 at 20 µg/dose) or, alternatively, formulation buffer for the non-adjuvanted group in order to have the desired final protein concentration of 100 µg/ml (equivalent to 10 µg/100 µl). Medium and low protein dosage were instead obtained through a pre-dilution step of vial 2×, respectively one to ten and one to twenty with formulation buffer, prior to final reconstitution with an equivalent volume of $AS01_E$ (2×) or Alum/TLR7 (2×) to reach final concentration of 10 µg/ml (equivalent to 1 µg/100 µl) and 1 µg/ml (equivalent to 0.1 µg/100 µl). Formulation buffer was used as diluent for control group. Compatibility studies were conducted in order to evaluate the short term stability of the formulation (up to 24 hours at 2-8° C. storage condition), both for vial with mix 2× and after the reconstitution process with adjuvants or placebo. Extended analytical panel was applied to characterise the formulations, through evaluation of the following parameters:

1. Physico-chemical (visual inspection, pH and osmolality)
2. Antigen identity (Western Blot for each single component, both protein and saccharide)
3. Total protein content (µBCA)
4. Sterility (microbial contamination through plate growth)
5. AS01 particle size (DLS)
6. Alum/TLR7 recovery (RP-HPLC)

No major incompatibilities were observed for the antigens/adjuvant or placebo combinations considered for evaluation in pre-clinical studies.

Example 2: Immunogenicity in Mice and Pre-Exposed Rabbits to Vaccine Adjuvanted with $AS01_E$ or ALUM/TLR7

The vaccine formulation was used to immunise different animal species:

i) Naïve mice, to investigate in vivo induction of both IgG and T cell response specific for the vaccine components. In these studies the vaccine was tested either non adjuvanted or adjuvanted with $AS01_E$ or Alum/TLR7 at different immunisation doses.

ii) S. aureus pre-exposed rabbits, to evaluate the response to the vaccine in a model in which pre-existing levels of IgG specific for the vaccine components are present. In this study the vaccine was tested at different doses either adjuvanted with $AS01_E$ or non adjuvanted. Alum/TLR7 adjuvant could not be used in this model due to the lack of the agonist receptor on rabbit cells.

The specific immune response was assessed by:
a) Measuring antigen-specific IgG by Luminex technology, both in mouse and rabbit immune sera at different time points after vaccination.
b) Evaluating the presence of $CD4^+$ T cells specific for the vaccine antigens in spleens of immunised mice.

c) Measuring the capability of antibodies present in mouse and rabbit sera to neutralise the biological activities of two of the protein components, the wild-type Hla and ClfA antigens.

An overview of the studies is presented in Table 1.

TABLE 1

Overview of vaccine in vivo preclinical studies in mice and rabbits

| Species, Sex/Age | Objectives | Antigen | Number of animals | Regimen | Dose protein (ug) | Dose polysaccharides (ug)* | Adjuvant[#] | Injection Volume/Route |
|---|---|---|---|---|---|---|---|---|
| BALB/c mice/female/5-week old | IgG quantitation, adjuvants comparison and sera testing in in vitro assays | 1-Vaccine | 30 | 2 injections 4 weeks apart | 10 | 2 | none | 100 μl/IM |
| | | 2-Vaccine | 30 | | 1 | 0.2 | none | 100 μl/IM |
| | | 3-Vaccine | 30 | | 0.1 | 0.02 | none | 100 μl/IM |
| | | 4-Vaccine | 30 | | 10 | 2 | Alum/TLR7 | 100 μl/IM |
| | | 5-Vaccine | 30 | | 1 | 0.2 | Alum/TLR7 | 100 μl/IM |
| | | 6-Vaccine | 30 | | 0.1 | 0.02 | Alum/TLR7 | 100 μl/IM |
| | | 7-Vaccine | 30 | | 10 | 2 | $AS01_E$ | 100 μl/IM |
| | | 8-Vaccine | 30 | | 1 | 0.2 | $AS01_E$ | 100 μl/IM |
| | | 9-Vaccine | 30 | | 0.1 | 0.02 | $AS01_E$ | 100 μl/IM |
| | | 10-Buffer | 15 | | — | — | none | 100 μl/IM |
| | | 11-Buffer | 15 | | — | — | Alum/TLR7 | 100 μl/IM |
| | | 12 Buffer | 15 | | — | — | $AS01_E$ | 100 μl/IM |
| Rabbit (New Zealand)/male/12-14-week old | IgG quantitation, adjuvants comparison and sera testing in in vitro assays | 1-Buffer | 12 | 2 injections 4 weeks apart | buffer | — | none | 500 μl/IM |
| | | 2-Vaccine | 12 | | 1 μg | 0.2 | none | 500 μl/IM |
| | | 3-Vaccine | 12 | | 10 μg | 2 | none | 500 μl/IM |
| | | 4-Vaccine | 12 | | 50 μg | 10 | none | 500 μl/IM |
| | | 5-Vaccine | 12 | | 1 μg | 0.2 | $AS01_E$ | 500 μl/IM |
| | | 6-Vaccine | 12 | | 10 μg | 2 | $AS01_E$ | 500 μl/IM |
| | | 7-Vaccine | 12 | | 50 μg | 10 | $AS01_E$ | 500 μl/IM |
| BALB/c Mice/female/5-week old | T cell response analysis | 1-Vaccine | 15 | 2 injections 4 weeks apart | 10 μg | 2 | none | 100 μl/IM |
| | | 2-Vaccine | 15 | | 10 μg | 2 | ALUM/TLR7 | 100 μl/IM |
| | | 3-Vaccine | 15 | | 10 μg | 2 | $AS01_E$ | 100 μl/IM |
| | | 4-Vaccine | 15 | | 1 μg | 0.2 | none | 100 μl/IM |
| | | 5-Vaccine | 15 | | 1 μg | 0.2 | ALUM/TLR7 | 100 μl/IM |
| | | 6-Vaccine | 15 | | 1 μg | 0.2 | $AS01_E$ | 100 μl/IM |
| | | 7-buffer | 6 | | — | — | none | 100 μl/IM |
| | | 8-buffer | 6 | | — | — | ALUM/TLR7 | 100 μl/IM |
| | | 9-buffer | 6 | | — | — | $AS01_E$ | 100 μl/IM |

*Polysaccharide in the bioconjugates content is about $\frac{1}{5}^{th}$ as compared to protein.
[#]Alum/TLR7 adjuvant dose used is 10 μg of TLR7 agonist adsorbed to Aluminum hydroxide.
$AS01_E$ adjuvant used is 1/20 of the human dose in mice (2.5 μg of MPL and 2.5 μg of QS-21 *Quillaja saponaria* Molina, fraction 21) and ½ of the human dose in rabbits (12.5 μg of MPL and 12.5 μg of QS-21).

Immunisation of Mice

Five week-old female mice were given two doses of 100 μl of either the buffer or the tested formulations (50 μl in each hind leg quadriceps) 28 days apart by the IM route. Blood samples were taken before 1st injection (day 0), 1 week, 2 and 4 weeks after the first injection (1wp1, 2wp1, 4wp1), and 1, 2, 4, 8, 12 and 16 weeks after the second injection (1wp2, 2wp2, 4wp2, 8wp2, 12wp2, 6wp2). The experiment was repeated 3 times in order to assess experimental variability. The statistical analysis was conducted on the pooled sample for each group. An overview of the study with the total number of mice used in the three experiments is shown in Table 2.

TABLE 2

Study Design for determination of IgG titre in immunised mice

| Group | Total Number of mice | Antigen | Protein Dose (μg) | Polysaccharides Dose (μg) | Adjuvant[#] | Injection Volume/Route |
|---|---|---|---|---|---|---|
| 1 | 30 | Vaccine | 10 | 2 | none | 100 μl/IM |
| 2 | 30 | Vaccine | 1 | 0.2 | none | 100 μl/IM |
| 3 | 30 | Vaccine | 0.1 | 0.02 | none | 100 μl/IM |
| 4 | 30 | Vaccine | 10 | 2 | Alum/TLR7 | 100 μl/IM |
| 5 | 30 | Vaccine | 1 | 0.2 | Alum/TLR7 | 100 μl/IM |
| 6 | 30 | Vaccine | 0.1 | 0.02 | Alum/TLR7 | 100 μl/IM |
| 7 | 30 | Vaccine | 10 | 2 | $AS01_E$ | 100 μl/IM |
| 8 | 30 | Vaccine | 1 | 0.2 | $AS01_E$ | 100 μl/IM |
| 9 | 30 | Vaccine | 0.1 | 0.02 | $AS01_E$ | 100 μl/IM |
| 10 | 15 | Buffer | — | — | none | 100 μl/IM |
| 11 | 15 | Buffer | — | — | Alum/TLR7 | 100 μl/IM |
| 12 | 15 | Buffer | — | — | $AS01_E$ | 100 μl/IM |

Evaluation of Vaccine-Specific IgG

The serological analysis to evaluate vaccine-specific IgG in mice and rabbits was based on a multiplex assay by the Luminex technology. This technology has been used to measure antibodies in human sera from subjects immunised with a vaccine against *StaphylococcuS. aureus* (Reediear et al, Clin Vaccine Immuno 2009, 16: 739-49).

The assay analyses five antigens simultaneously (5-plex) using magnetic beads coated with the three SA recombinant proteins ($SPA_{mut}$, $ClfA_{mut}$, $Hla_{mut}$) and the two capsular polysaccharides of different serotypes (CP5 and CP8). Protein antigens are covalently conjugated to the free carboxyl groups of microspheres using an N-hydroxysulfosuccinimide-enhanced carbodiimide (EDC)-mediated conjugation chemistry. CP5 and CP8 are biotinylated using Biotin-Hydrazide (BH) and EDC, purified and subsequently conjugated to Streptavidin beads.

A pentavalent standard serum was prepared by pooling hyperimmune sera collected at D12 Post 2 from 5 mice immunised with $Hla_{H35R}$+$ClfA_{mut}$+CP5-TT+CP8-TT+$SpA_{mut}$-10 μg/Alum/TLR7. An arbitrary titre of 100 RLU/ml was assigned to the pentavalent standard.

The assay was set up accordingly to the following criteria:

No cross-reactivity between the five antigens observed by comparing signals obtained by monoplex versus multiplex setting.

Specificity of the assay confirmed by multiplex pre-adsorption studies.

Intra and inter-assay reproducibility of the assay (% CV<10% and 20% respectively).

Linearity assessment in the linear range of the 5PL MFI curve obtained with standard and test sera: $R^2$ values>0.9.

Lower Limits of Detection (LLOD, see table below) for each antigen were determined as mean RLU from black samples.

Lower Limits of Quantification (LLOQ, see table below): the lower titres that could be determined with acceptable accuracy (CV<20% in spiking experiments) using a Minimum Required dilution (MDR) of 1:1000.

|  | Hla | CP8 | ClFA | SPA | CP5 |
|---|---|---|---|---|---|
|  | RLU/ml (MDR 1:1000) | | | | |
| LOD = Mean + 3SD | 0.03 | 0.01 | 0.04 | 0.05 | 0.02 |
| LLOQ (RLU/ml) prelim based | 0.7 | 0.18 | 3.09 | 0.96 | 0.77 |

For sample testing, up to five increasing dilutions were independently prepared and loaded onto 96 wells plates with an adequate amount of coupled microspheres. Two replicates of each dilution were tested. Antigen specific antibodies were revealed by an anti-mouse IgG Phycoeritrin-labelled secondary antibody and MFI were measured using the Luminex 200 Reader.

The analysis was performed using three experiments for each group at different time-points. In order to assess the biological variability among experiments for each antigen and dose, a 2-way mixed ANOVA was applied ("group" and "experiment" as fixed and "individual mice" as random effects). No significant group-experiment interaction was observed, except for $ClfA_{mut}$ and $Hla_{mut}$ at dose 0.1 μg with p-value=0.001.

The overall results on mouse studies (FIG. 1, data not shown for 0.1 μg dose) indicated that:

All the vaccine components were immunogenic in mice. Control groups (10, 11 and 12) showed no detectable antibodies against any of the five antigens. Similarly, no detectable IgGs were measured in pre-immune sera, except for $Hla_{mut}$ antigen, for which 14% of estimated titres were slightly over the LLOQ.

Responses for vaccine without adjuvants were always inferior to responses to vaccine with adjuvants.

A significant dose effect was observed in all groups with and without adjuvant (1-way ANOVA was applied and the adjustments were made for multiple comparisons, using Tukey's "Honest Significant Difference."). In particular:

Without adjuvant: 0.1 μg<1 μg<10 μg for all antigens at post $2^{nd}$ immunisation (p-value<0.01 Tukey's post-test).

$AS01_E$: 0.1 μg<1 μg<10 μg for $ClfA_{mut}$, $HLA_{mut}$ and $SpA_{mut}$ at any time points (p-value<0.05 Tukey's post-test); 0.02 μg<0.2 μg≤2 μg (polysaccharide-based dose) for CP8 (p-value<0.05 Tukey's post-test). For CP5 0.02 μg=0.2 μg>2 μg at post $2^{nd}$ immunisation (p-value<0.0001 Tukey's post-test).

Alum/TLR7: 0.1 μg<1 μg<10 μg for $ClfA_{mut}$ and $SpA_{mut}$ at any time points (p-value<0.05 Tukey's post-test). While for CP5 0.02 μg=0.2 μg>2 μg (polysaccharide-based) at post $2^{nd}$ immunisation (p-value<0.05 Tukey's post-test), for CP8 0.02 μg<0.2 μg>2 μg at any time points (p-value<0.05 Tukey's post-test), finally 0.1 μg<1 μg 10 μg for $HLA_{mut}$.

Two immunisations were required to obtain the highest IgG titres (p-value<0.01 Tukey's post-test).

Selection of Pre-Exposed Rabbits and Study Design

A total of 350 rabbits were screened by ELISA to measure in the sera pre-existing antibodies against the three protein antigens and the two polysaccharides present in the vaccine. The ELISA analysis showed that absorbance $A_{450nm}$=0.2 was the limit of detection to measure IgG response at 1/100 dilutions, and that all rabbits were positive to at least one antigen.

In order to assemble the rabbit groups according to the study design shown in Table 3, a selection of 84 rabbits was undertaken.

TABLE 3

Rabbit Study Design

| Group | Number of Rabbits | Antigen | Dose protein (μg) | Dose polysaccharides (μg) | Adjuvant[#] | Injection Volume/Route |
|---|---|---|---|---|---|---|
| 1 | 12 | buffer | — | — | none | 500 μl/IM |
| 2 | 12 | Vaccine | 1 μg | 0.2 | none | 500 μl/IM |
| 3 | 12 | Vaccine | 10 μg | 2 | none | 500 μl/IM |
| 4 | 12 | Vaccine | 50 μg | 10 | none | 500 μl/IM |
| 5 | 12 | Vaccine | 1 μg | 0.2 | $AS01_E$ | 500 μl/IM |
| 6 | 12 | Vaccine | 10 μg | 2 | $AS01_E$ | 500 μl/IM |
| 7 | 12 | Vaccine | 50 μg | 10 | $AS01_E$ | 500 μl/IM |

[#]$AS01_E$ adjuvant is composed of 12.5 μg of MPL, a TLR4 activator, and 12.5 μg of QS-21 (*Quillaja saponaria* Molina, fraction 21), which increases antigen presentation to APCs.

The 350 rabbits were divided into 5 subgroups, or strata, based on number of antigens with an ELISA result>0.2 $A_{450nm}$ (i.e., ELISA>0.2 for 5, 4, 3, 2 or ≤1 antigens). All rabbits in each of the two strata 'positive for 5' or 'positive for 4' antigens (total n=35) were selected to be included in the study and randomly allocated to the 7 experimental group (total n=5 to each group). The other required rabbits were taken from the 'positive for 3 antigen' strata (n=102) in which a further selection criteria was applied. In the 'positive for 3 antigens' strata, only rabbits positive for ClfA (n=64) were considered eligible for the study and among these, only rabbits with ELISA result, for both Hla and SpA antigens, within the interquartile range were considered eligible for the study (n=51). Forty-nine of the 51 rabbits were randomly selected and allocated to one of the 7 study groups (total n=7 to each group).

Immunisation of Rabbits

The same bed-side mix approach described above was used for preparing the vaccine formulations to be tested in pre-exposed rabbits, using appropriate concentration and dilution step according to antigens final dose and injection volume.

Pre-exposed rabbits (12-14 week old male) were given two doses of either formulation buffer only (control groups) or one of the six tested vaccine formulations 28 days apart, at day 1 and day 29, by the IM route. Blood samples were taken before $1^{st}$ injection (day 0), 1 week, 2 and 4 weeks after the first injection (1wp1, 2wp1, 4wp1), and 2 and 5 weeks after the second injection (2wp2, 5wp2).

Evaluation of Vaccine-Specific IgG

The assay used for determination of vaccine-specific IgG in rabbits was the Luminex 5-plex described above. The rabbit assay was developed in a 96 well format.

A pentavalent standard serum was prepared by pooling hyperimmune monovalent rabbit polyclonal sera against all 5 antigens. An arbitrary titre of 50000 RLU/ml for all antigens was assigned to the pentavalent standard.

The assay was set up according to the criteria reported above. Inter-assay reproducibility was determined (% CV<15%). Linearity assessment yielded $R^2$ values>0.9. LOQ and LOQ are reported below.

|  | CLFA | CP 5 | CP 8 | HLA | $SPA_{mut}$ |
|---|---|---|---|---|---|
|  | RLU/ml (MDR 1:100) | | | | |
| LOD (mean + 3SD) | 0.01 | 0.01 | 0.01 | 0.01 | 0.01 |
| LLOQ (dilution correct) | 14 | 6 | 57 | 9 | 60 |

For sample testing, 8 serial 3 fold dilutions (starting from 1:100) were automatically prepared and loaded onto single 96 wells plate with an adequate amount of coupled microspheres. Antigen specific antibodies were revealed by an anti-rabbit Fab2 IgG. Phycoeritrin-labelled secondary antibody and MFI were measured using the Luminex Flexmap 3D Reader. IgG titres of each sample/antigen were determined by estimating the median of all valid individual titres obtained from the 5PL curve.

Geometric mean titres (GMTs) for anti-$ClfA_{mut}$, -$Hla_{mut}$, -CPS, -CP8 and -$SpA_{mut}$, at 4 weeks after $1^{st}$ vaccination and 2 weeks after $2^{nd}$ vaccination, showed a statistically significant increase from pre-vaccination in all seven groups (FIG. 3). Antibody titres at 2 weeks post $2^{nd}$ vaccination were higher than after $1^{st}$ vaccination. At 2 weeks after $2^{nd}$ vaccination, all vaccinated groups showed a statistically significant higher antibody response as compared to buffer control group for all antigens except for $Hla_{mut}$ for which antibody titres were similar to buffer control group at any time point. After the $2^{nd}$ vaccination, the GMTs between the adjuvanted and non-adjuvanted did not show a significant difference.

Example 3: Analysis of Functional Antibodies

Sera obtained from the immunised mice and rabbits were tested for the presence of functional antibodies capable of neutralising wild-type Hla and ClfA activities in vitro.

Inhibition of Hla Activity—Mice

The ability of vaccine-specific antibodies to inhibit Hla-induced hemolysis was evaluated in an in vitro red blood cell (RBC)-based hemolysis neutralisation assay, carried out modifying a previously described method (Bagnoli et al, PNAS 2015, 112: 3680-3685). Alpha hemolysin neutralisation assay was performed using three pools of 10 sera each from three different repeated experiments for each immunisation group. Neutralisation titres were determined calculating the effective dilution ($ED_{50}$) defined as the dilution of the serum which neutralises the toxicity of Hla by 50%.

For each group at each time point, the $ED_{50}$ was evaluated by estimation of the inflection point parameter of a four-parameter logistic (4PL) by a non-linear regression of neutralisation curves.

Figure 1A:
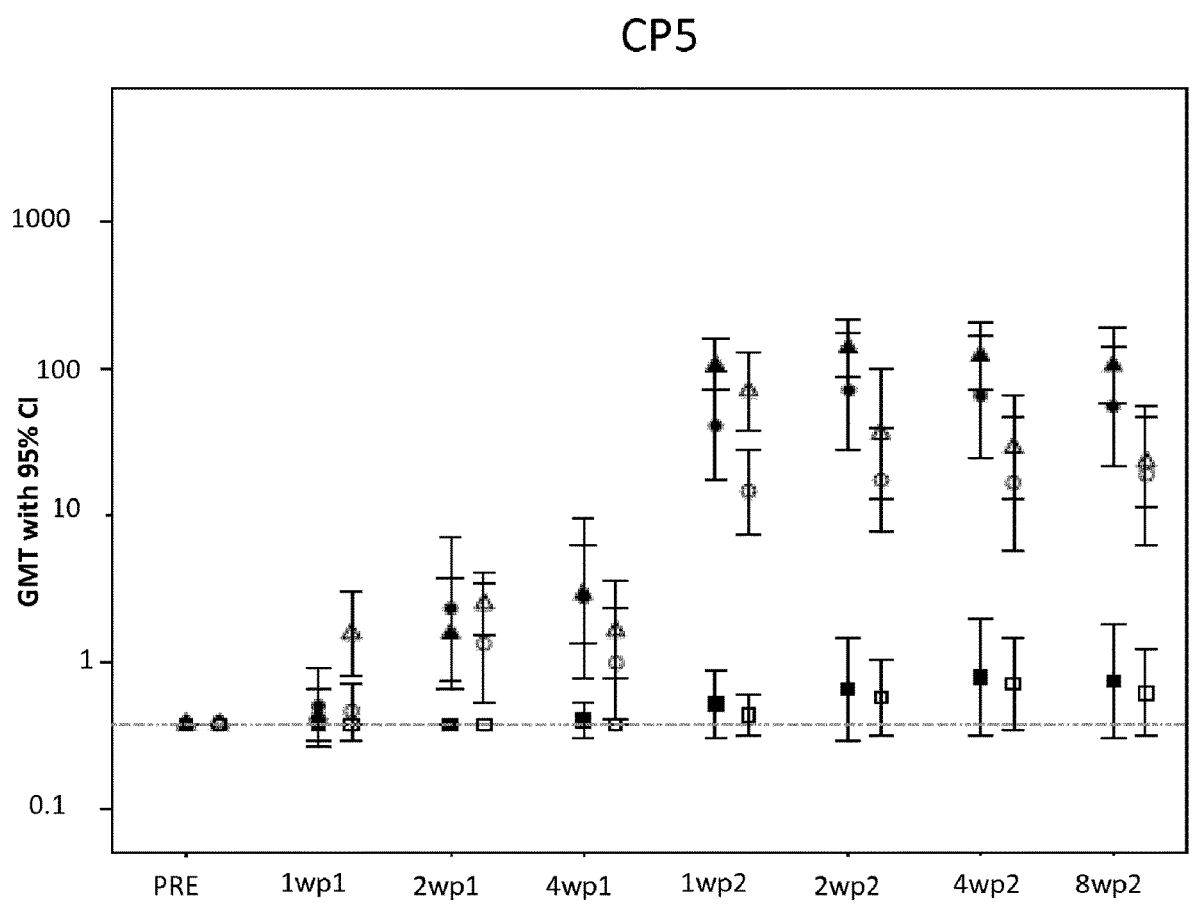
FIG. 1. Vaccine-specific IgG in mice. Antigen-specific IgG titres (anti-CP5 (1A), anti-CP8 (1B), anti-Hla (1C), anti-ClfA (1D), and anti-SpA (1E) in naïve mice immunised with vaccine unadjuvanted and adjuvanted with Alum/TLR7 or $AS01_E$. Each symbol identifies a group of 30 mice, which were immunised at day 1 and 29 with 10 μg (open symbols) or 1 μg (filled symbols) with AS01 (triangles) Alum/TLR7 (circles) or no adjuvant (squares). Y-axis: GMT with 95% CI. Bleedings were taken at different time points after the first and the second immunisation. The GMT of IgG titres and the time points of the bleedings analysed are reported on the y and axis respectively. Dotted line=LLOQ/2: half of the lower limit of quantitation. 30 individual BALB/c sera for each timepoint were analysed by Luminex.
Figure 1B:
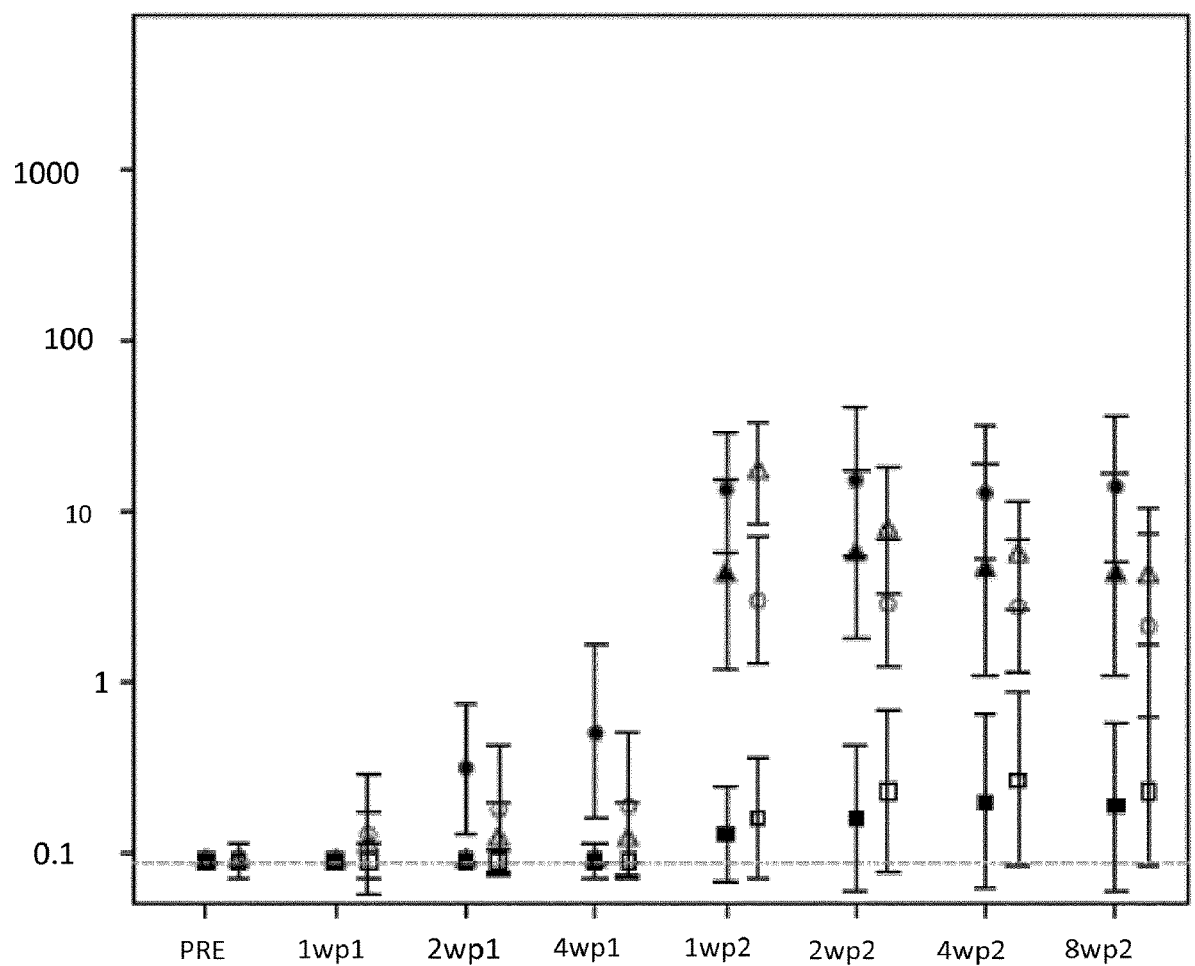
Figure 1C:
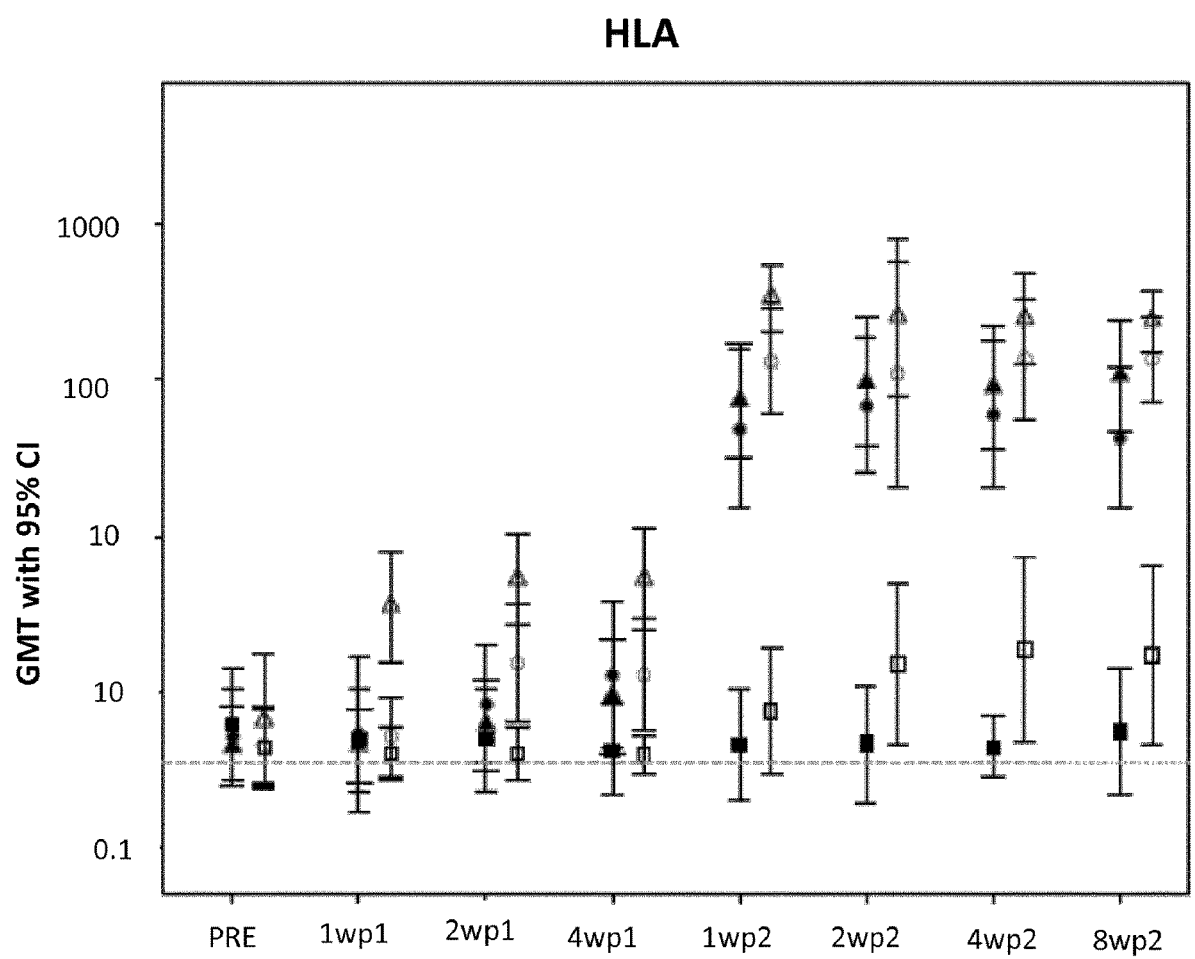
Figure 1E:
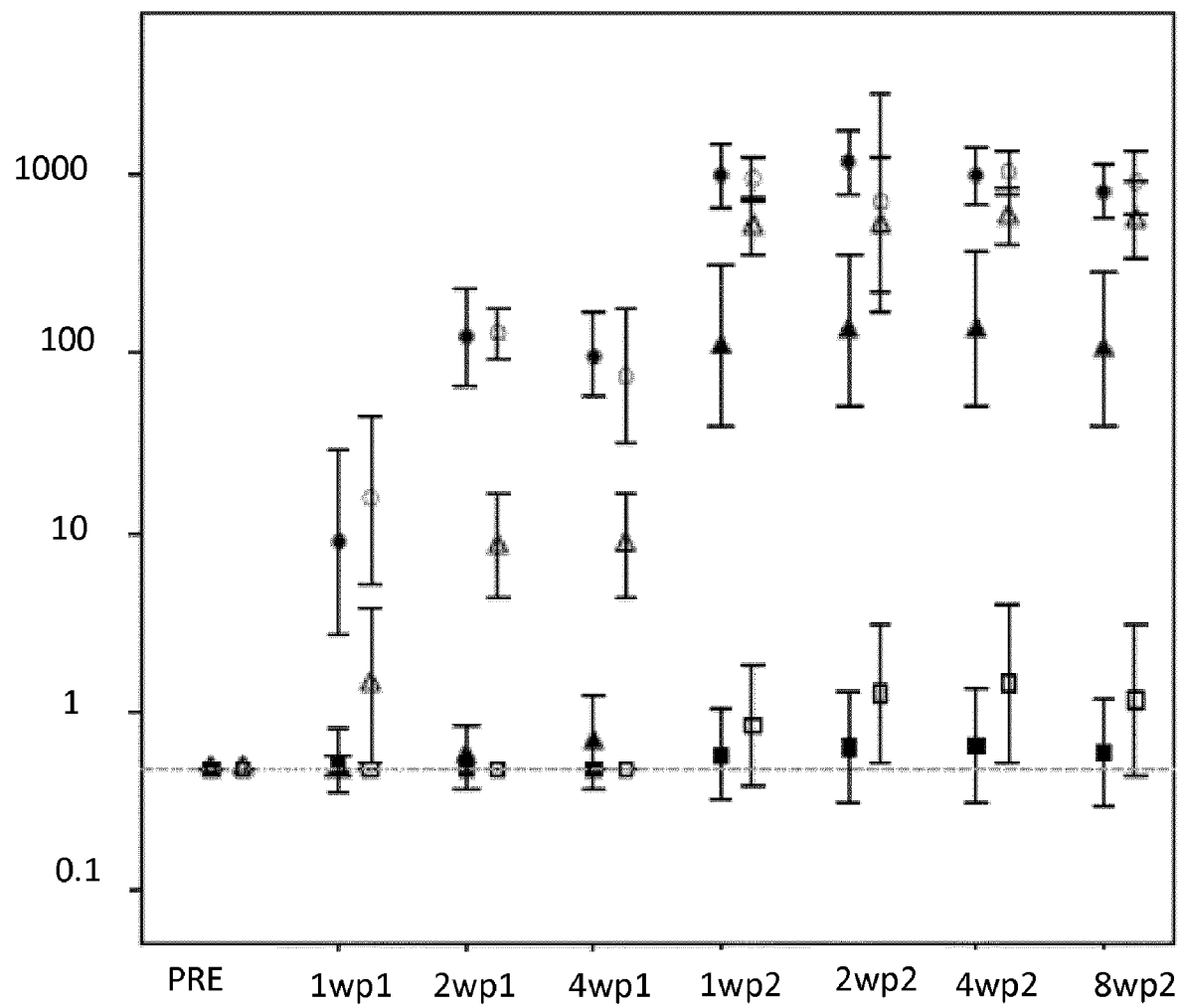
Figure 2A:
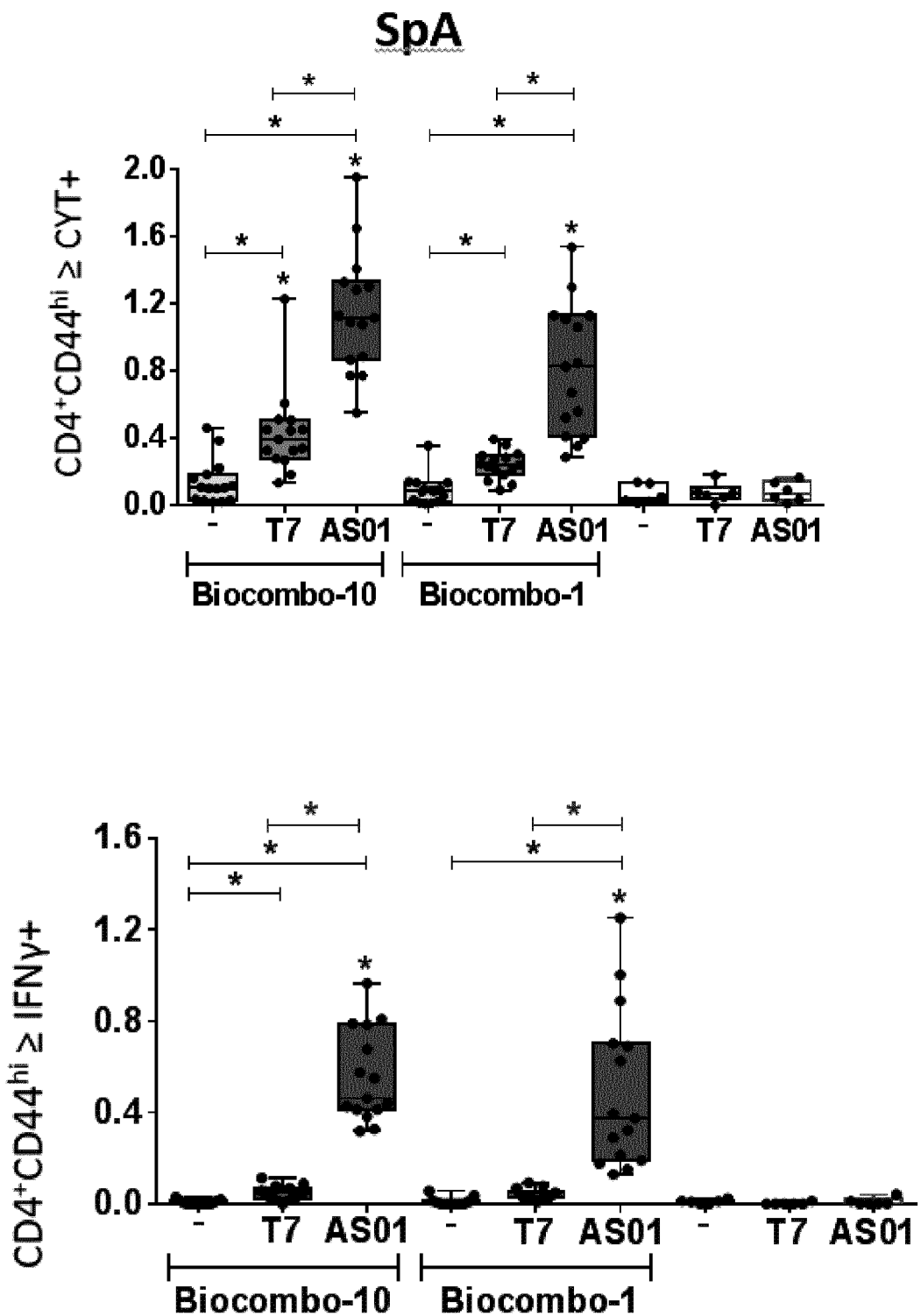
FIG. 2: Magnitude and quality of vaccine-specific CD4 T-cell responses in mice induced by vaccine unadjuvanted and adjuvanted with Alum/TLR7 or $AS01_E$. Splenocytes from single mice sacrificed 12 days after second immunisation were stimulated or not with vaccine proteins in vitro (2A: $SpA_{mut}$, 1 μg/ml; 2B: $Hla_{mut}$, 10 μg/ml; 2C: $ClfA_{mut}$, 10 μg/ml), stained and analysed by ICS. $CD4^+CD44^{high}$ T cells producing IL-2, TNF, IL-4/IL-13, IFN-γ or IL-17A were identified. Upper graph: $CD4^+CD44^{high} \geq CYT+$. Lower graph: $CD4^+CD44^{high} \geq IFN$-γ. The response of unstimulated cells was subtracted from that of stimulated cells. Magnitude: Percentages of $CD4^+CD44^{high}$ T cells producing at least one of the cytokines analysed in response to vaccine protein stimulation. Quality: Percentages of $CD4^+CD44^{high}$ T cells producing at least: IFN-γ but not IL-4/IL-13. Two-way ANOVA of % Geometric Mean ratios, p<0.05 indicated: * Vaccine (with or without adjuvant) vs. control group; * Vaccine with adjuvant vs. Vaccine without adjuvant; * Vaccine with $AS01_E$ vs. Vaccine with Alum/TLR7; * Vaccine-10 μg vs. Vaccine-1 μg.
Figure 2B:
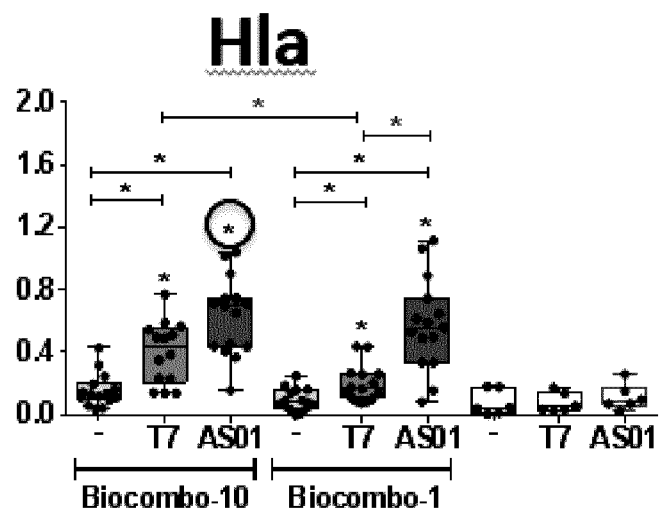
Figure 2B:
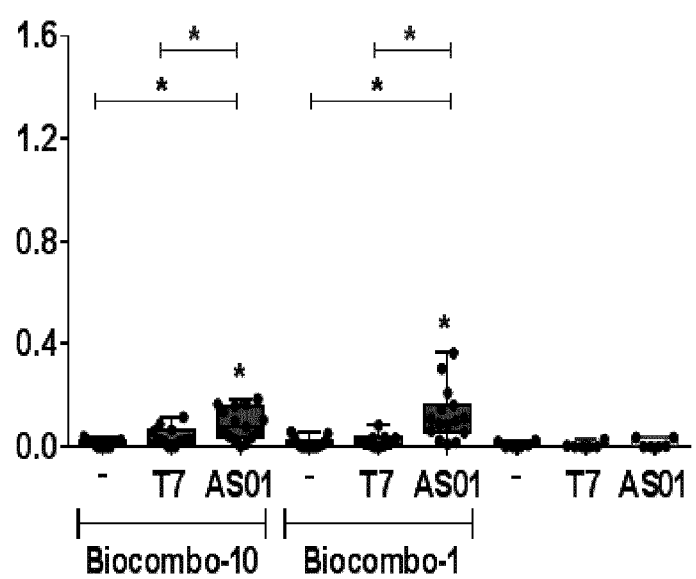
Figure 2C:
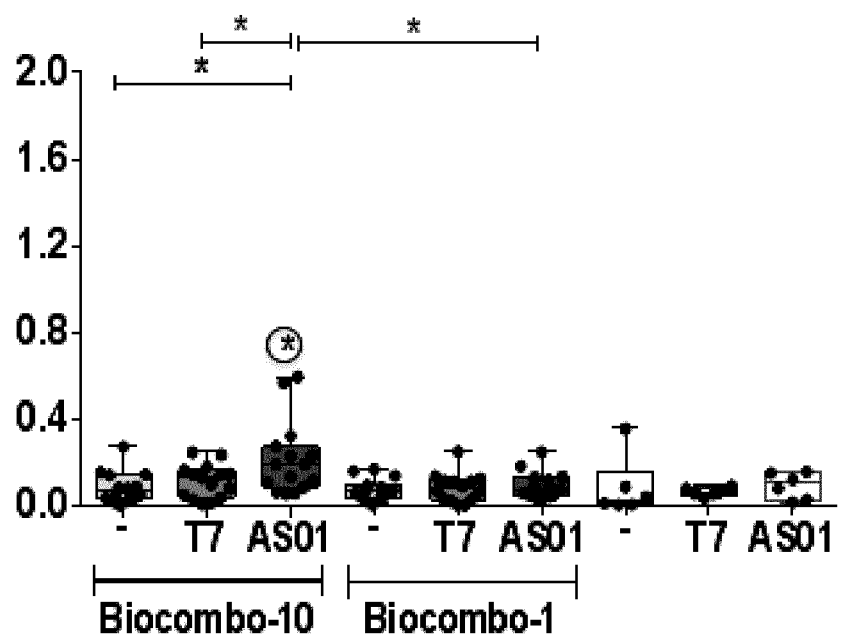
Figure 2C:
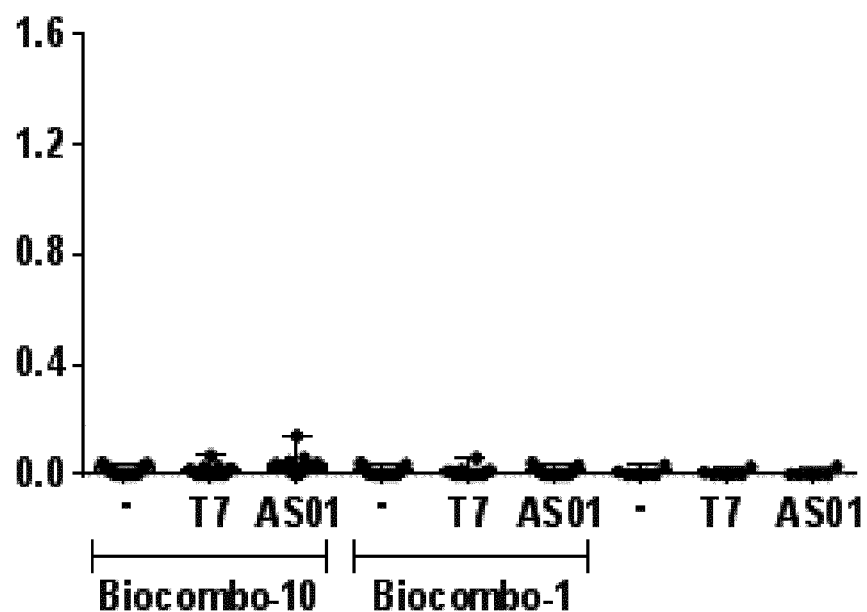
Figure 3A:
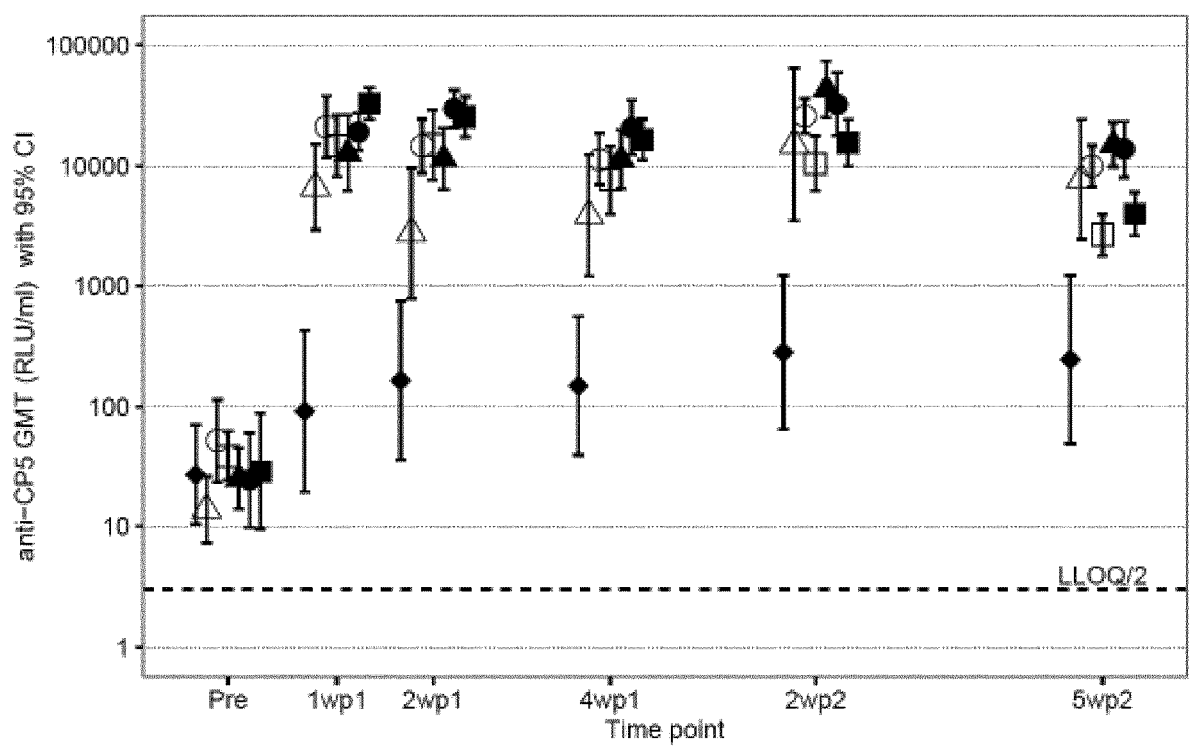
FIG. 3: Vaccine-specific IgG in pre-exposed rabbits. Geometric mean titres anti-CP5 (3A), anti-CP8 (3B), anti-Hla (3C), anti-ClfA (3D), and anti-SpA (3E) in pre-exposed rabbits that received two injections of vaccine with or without $AS01_E$ adjuvant or buffer. Pre: pre-dose 1, 1wp1: 1 week post-dose 1, 2wp1: 2 weeks post-dose 1, 4wp1: 4 weeks post-dose 1, 2wp2: 2 weeks post-dose 2, 4wp2: 4 weeks post-dose 2; 5wp2: 5 weeks post-dose 2. LLOQ2 dotted line: half of the lower limit of quantitation. Triangles: 1 μg dose; Circles: 10 μg dose; squares: 50 μg dose. Open symbols: no adjuvant, Filled symbols: $AS01_E$. Buffer control shown as filled diamonds. The grey dotted line indicates the reciprocal of the lowest dilution used in the assay.
Figure 3B:
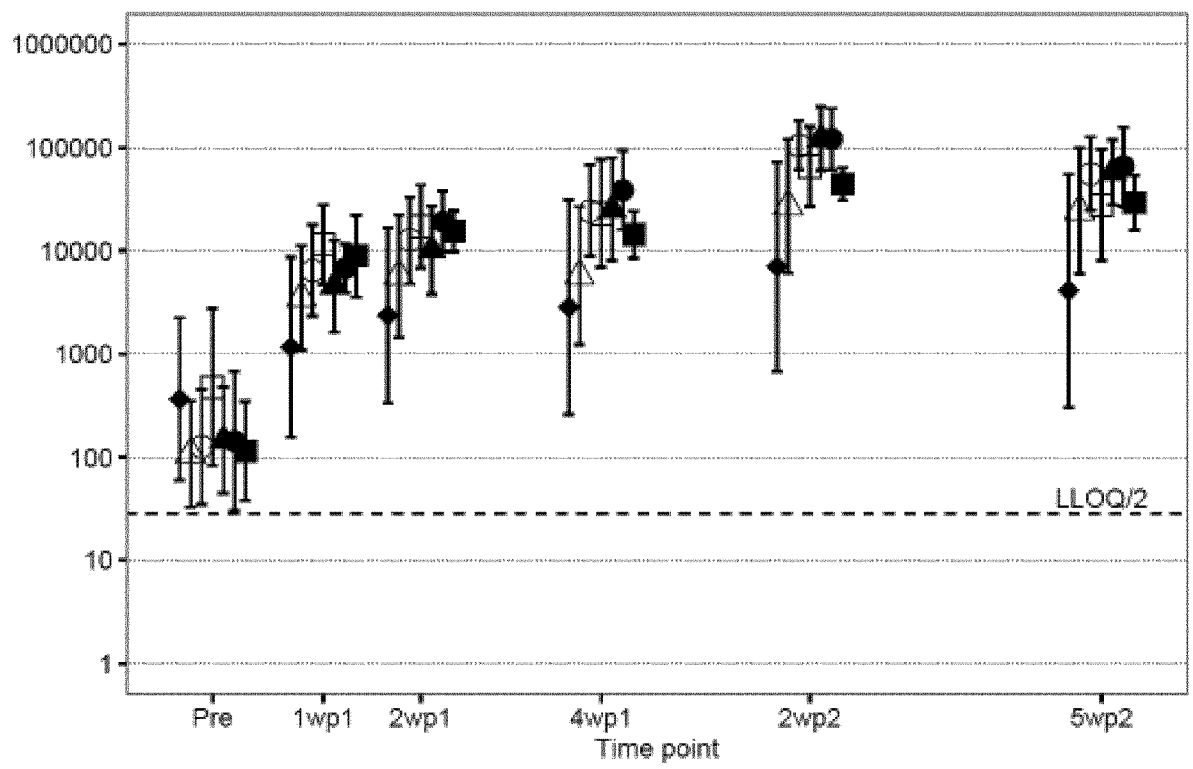
Figure 3C:
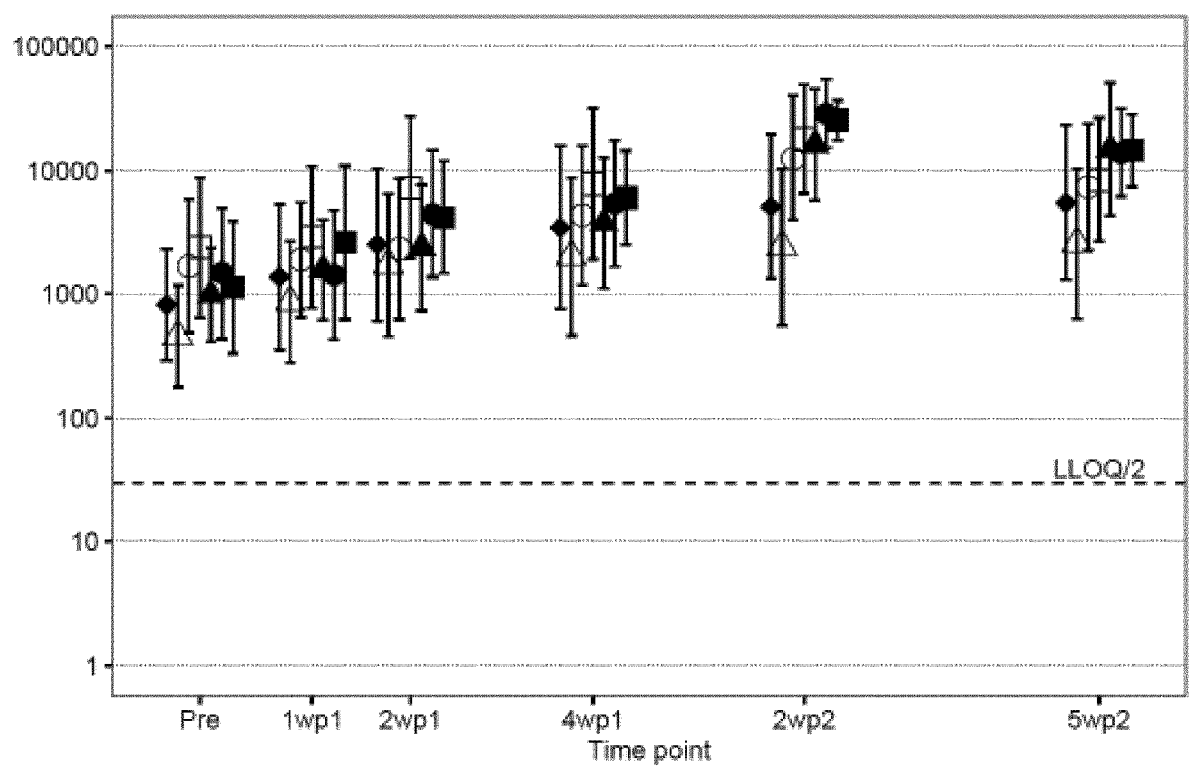
Figure 3D:
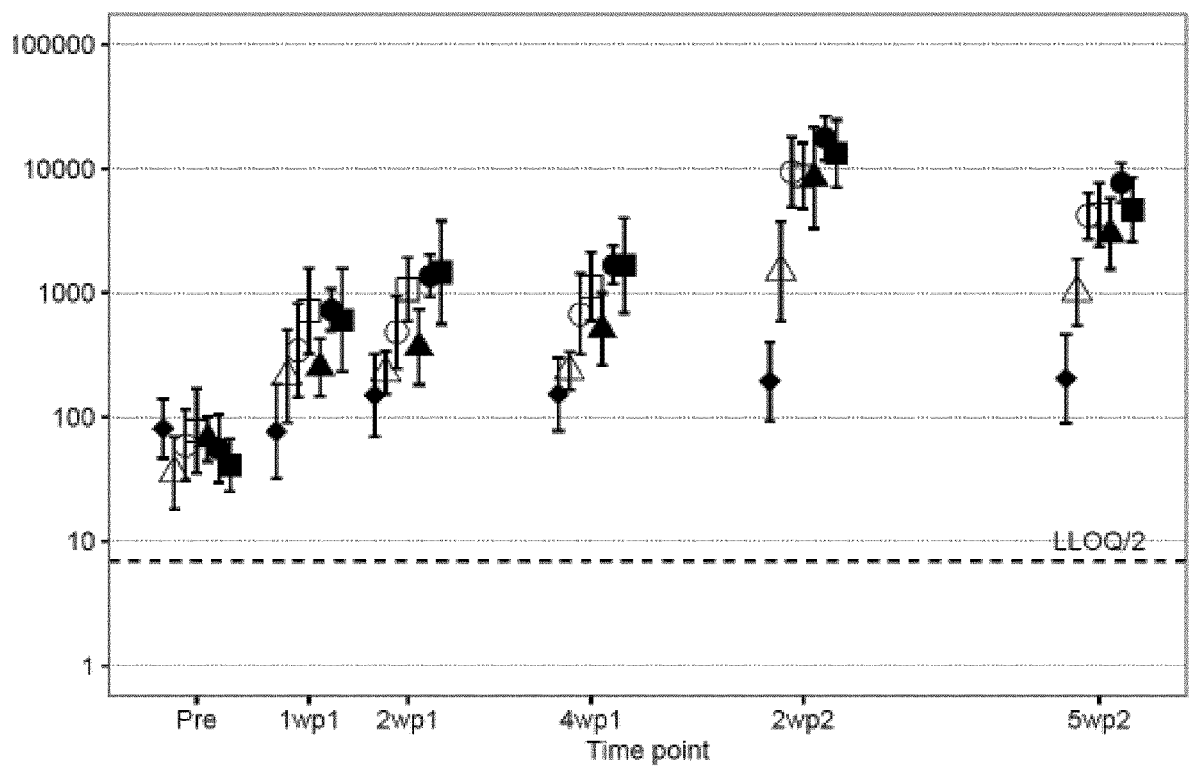
Figure 3E:
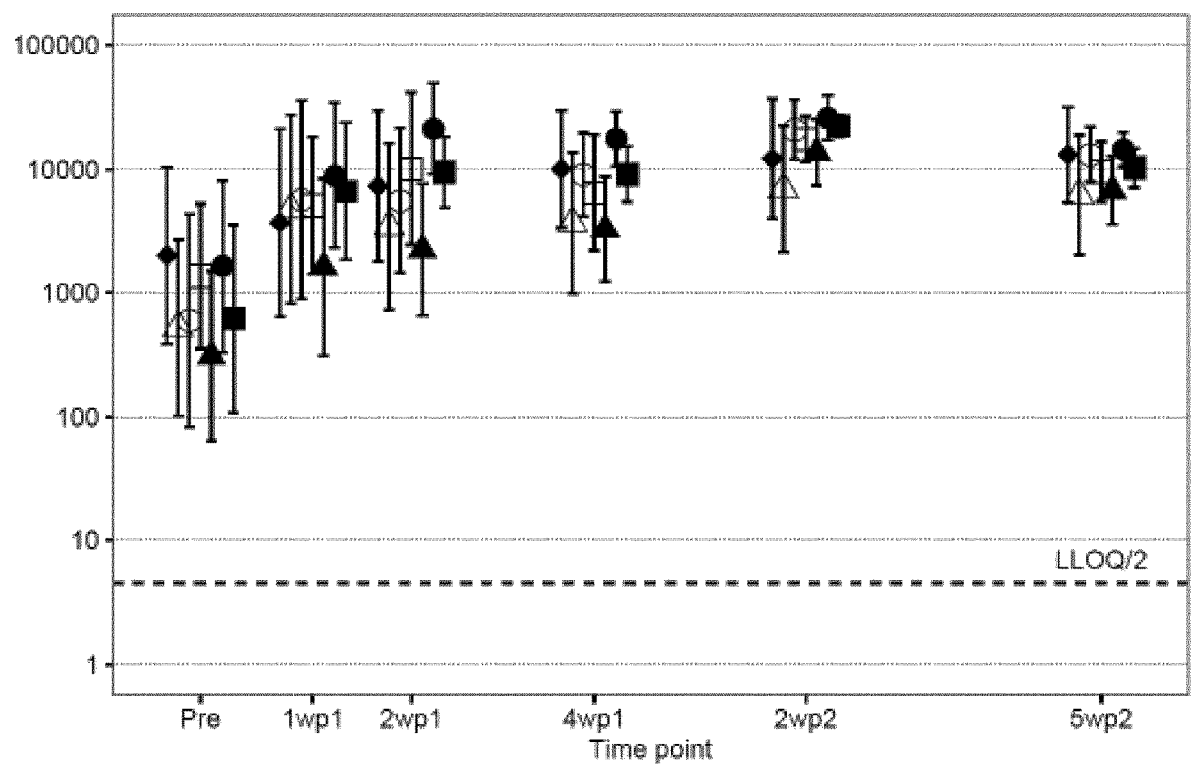
Figure 4A:
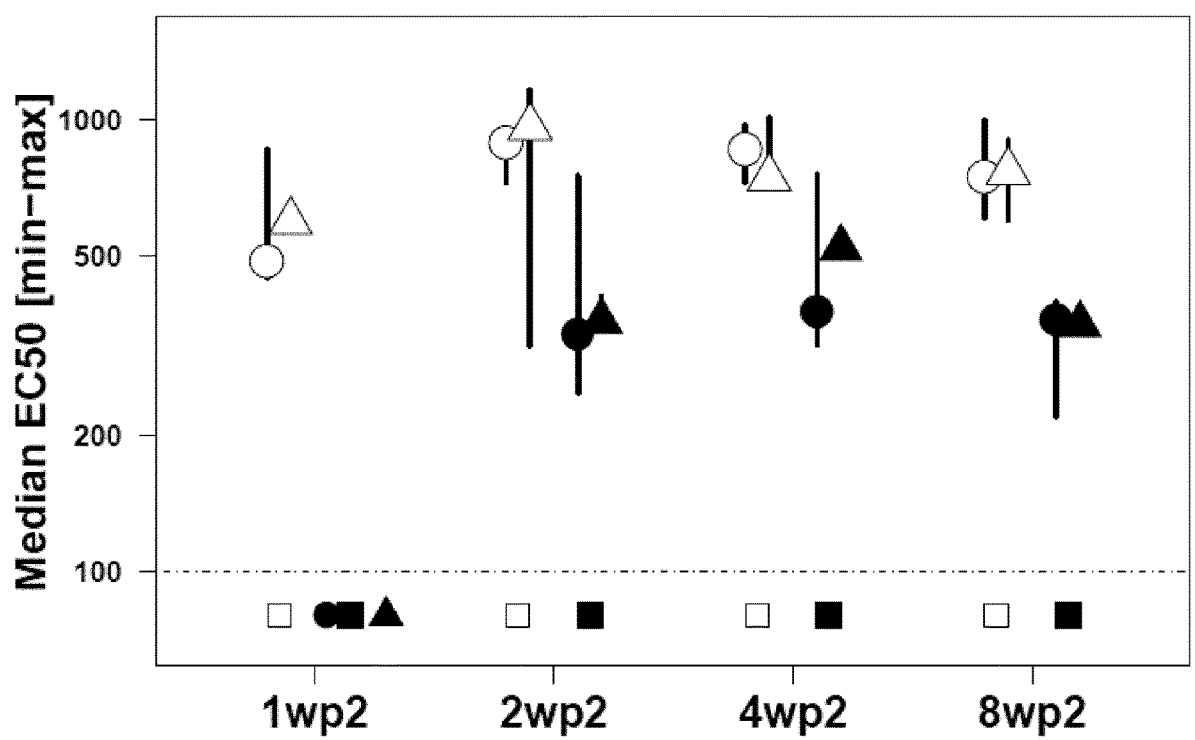
FIG. 4A: Vaccine induces functional IgG neutralising in vitro Hla activity in mice. Mice (10 mice/group) were immunised with the vaccine at indicated dosages without adjuvant or in the presence of either Alum/TLR7 or $AS01_E$ adjuvant. Neutralisation titres of pooled sera were measured at each time point and expressed as median values (red and blue squares and stars) of the three independent studies. Upper and lower values of the bar represent the maximum and the minimum titres, respectively. Open symbols: 10 μg dose; Closed symbols: 1 μg dose. Squares: no adjuvant; Triangles: $AS01_E$ adjuvant; Circles: Alum/TLR7 adjuvant. The grey dotted line indicates the reciprocal of the lowest dilution used in the assay.

The results obtained are shown in FIG. 4A and indicated that:

No functional antibodies were detected in absence of adjuvant and in 0.1 µg adjuvanted groups (data not shown).

Hla neutralisation was observed after two immunisations, using both adjuvants with 1 or 10 µg doses.

Formulation with 10 µg induced statistically significant higher neutralisation titres as compared to formulation with 1 µg (p≤0.05 Wilcoxon test).

Inhibition of ClfA Activity—Mice

A ClfA binding inhibition assay was developed to evaluate whether the vaccine elicited functional antibodies able to inhibit ClfA activity. The assay is an ELISA-based measurement of the ability of antibodies to inhibit the binding of ClfA to fibrinogen. If the antibodies efficiently bind to ClfA, interaction with fibrinogen is inhibited. The sera titres are defined as the reciprocal serum dilution giving 50% reduction of fibrinogen binding ($ED_{50}$). A four-parameter logistic (4PL) non-linear regression model is used for curve-fitting analysis of inhibition curves and the $ED_{50}$ has been evaluated by estimation of the 4PL inflection point.

ClfA binding assay has been applied to sera elicited by vaccine formulation in naïve mice.

Sera collected at the following immunisation time-points were analysed: 4 weeks after the first immunisation (4wp1); and 1-2-4-8-12-16 weeks after the second immunisation (1wp2, 2wp2, . . . )

Figure 5A:
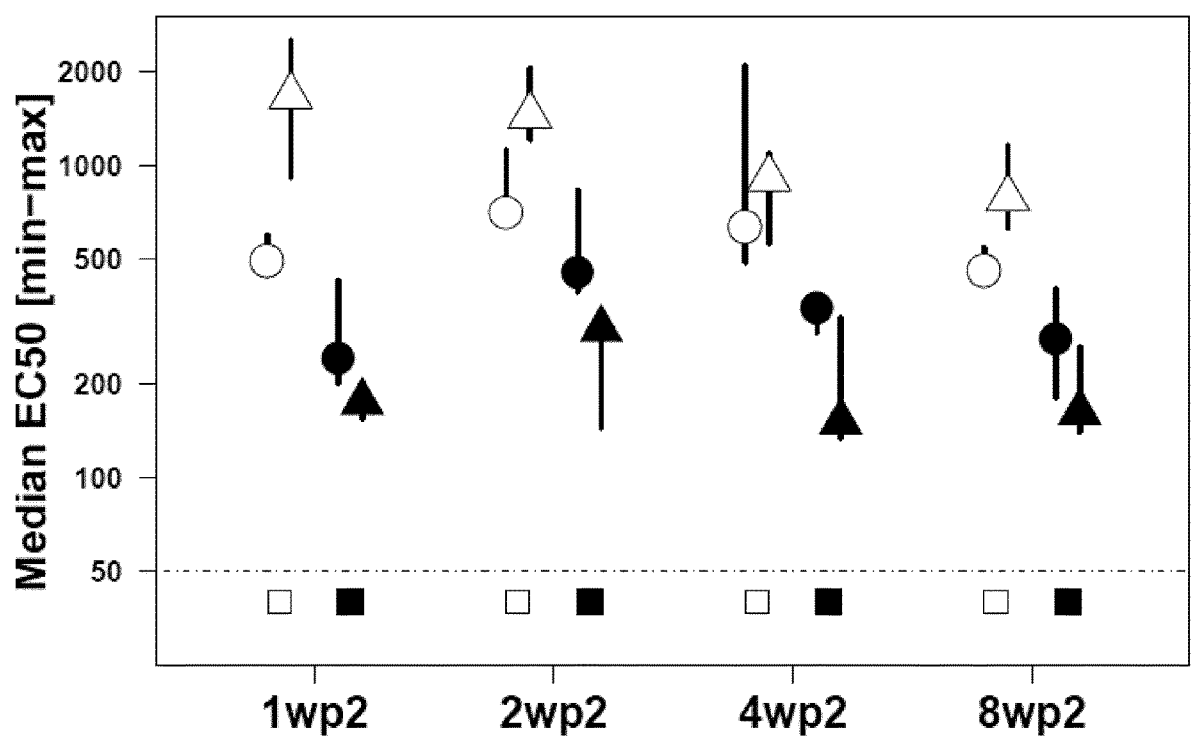
FIG. 5A: Vaccine induces functional IgG neutralising in vitro ClfA activity in mice. Mice (10 mice/group) were immunised with the vaccine at indicated dosages without adjuvant or in the presence of either Alum/TLR7 or $AS01_E$ adjuvant in three independent in-vivo experiments. Neutralisation titres of pooled sera of the three in-vivo experiments were measured at each time point and expressed as median values. Upper and lower values of the bar represent the maximum and the minimum titres, respectively. Open symbols: 10 μg dose; Closed symbols: 1 μg dose. Squares: no adjuvant; Triangles: $AS01_E$ adjuvant; Circles: Alum/TLR7 adjuvant. The grey dotted line indicates the reciprocal of the lowest dilution used in the assay.

The results obtained are shown in FIG. 5A.

Sera from each group were pooled (10 mice each) and neutralisation titres ($ED_{50}$) were measured for each pool at different time-points. The analysis was performed on three independent mouse immunisation experiments for each group at different time-points. Results are shown in FIG. 5A where each dot represents the median value of the three independent experiments; the upper and the lower ends of the bar represent the maximum and the minimum value respectively.

The results obtained indicated that:

No ClfA neutralisation was measured at 0.1 µg dosage and in absence of adjuvants (data not shown).

ClfA neutralisation was observed using both adjuvants with 1 or 10 μg

Formulation with 10 μg dosage (referred to ClfA content) induced statistically significant higher neutralisation titres as compared to the formulation with 1 μg. (p value Wilcoxon test 0.05)

At 10 μg dosage AS01$_E$ outperformed Alum/TLR7 at 1w and 2wp2 (p value Wilcoxon test≤0.05)

Sera obtained from the immunised rabbits were tested for the presence of functional antibodies capable of neutralising wild-type Hla and ClfA activities in vitro, using the assays previously described for mouse sera.

Inhibition of Hla Activity—Rabbits

Rabbits were treated as reported in table 3. All animals were bled before 1st injection (day 0), 1 week, 2 and 4 weeks after the first injection (1wp1, 2wp1, 4wp1), and 2 and 5 weeks after the second injection (2wp2, 5wp2). Neutralisation assays were performed on single sample sera at the different time points described above.

Figure 4B:
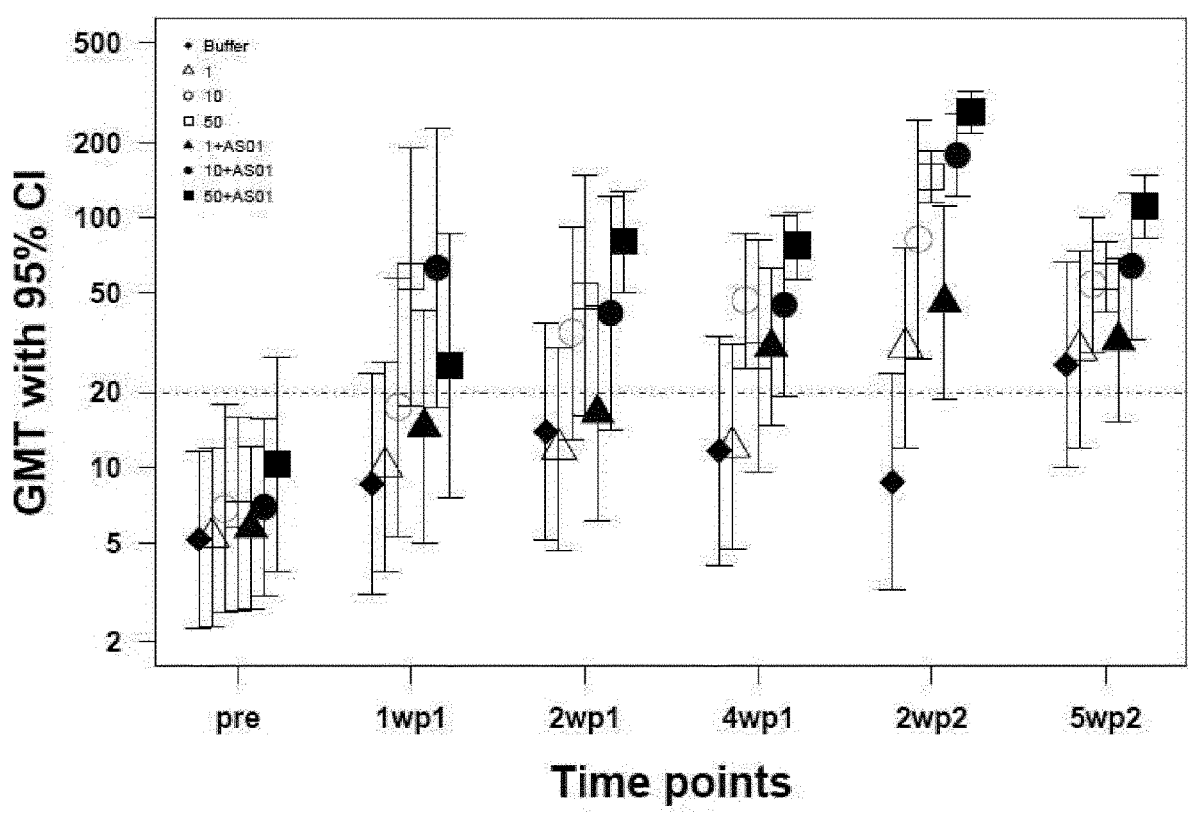
FIG. 4B: Vaccine induces functional IgG neutralising in vitro Hla activity in pre-exposed rabbits. The Hla neutralising titers and the time points of the bleedings analyzed are reported on the y and x axis respectively. The grey dotted line indicates the reciprocal of the lowest dilution used in the assay. An arbitrary titre of 3 was assigned to non-responders. Triangles: 1 μg dose; Circles: 10 μg dose; squares: 50 μg dose. Open symbols: no adjuvant, Filled symbols: $AS01_E$. Buffer control shown as filled diamonds.

Geometric mean titres, at each time point were descriptively summarised, including 95% confidence intervals (CIs). The GMTs and 95% CIs were calculated by back transformations of the confidence limits computed for the mean of the log-transformed titres based on Student's t-distribution (FIG. 4B). The dashed line represents the minimum required dilution established for measurement of each rabbit serum.

Titres Vs. Pre-Immune:

The geometric mean fold rise from pre-vaccination at each post-vaccination time point was calculated based on the log-transformed titres. Student's paired t test was used to analyse the differences between pre and post log-transformed titres.

At 2wp1 all groups with a protein content ≥10 ug induce higher titres as compared to pre-immune (all p values<0.017)

At 2wp2: all immunised groups induce higher titres as compared to pre-immune (all p values<0.005)

Titres Vs. Buffer Group:

Pair-wise comparisons between immunised groups and buffer at each time-point were performed using Welch's Student's t-test.

At 2wp1 only adjuvanted 50 ug dosage induces higher titre as compared to buffer group (all p values<0.003)

At 2wp2 all immunised groups, excluded no-adjuvanted 1 ug dosage, induce higher titre as compared to buffer (all p values<0.013)

Post-1 vs. Post-2:

Significant differences (p value Welch's Student t-test<0.025) where observed between 2wp1 and 2wp2 in the 50 μg, 10 μg+AS01$_E$, 50 μg+AS01E.

Inhibition of ClfA Activity—Rabbits

The ClfA binding inhibition assay was applied to sera elicited by vaccine formulation in pre-exposed rabbits. Titres were determined by estimation of the inflection point parameter of a four-parameter logistic (4PL) by a non-linear regression of the inhibition curves.

Sera collected at the following immunisation time-points were analysed: Pre-immunisation, 4 weeks after the first immunisation (4wp1), 2 weeks after the second immunisation (2wp2).

Sera from each group (12 rabbits each) were collected and neutralisation titres (ED$_{50}$) were measured for each individual rabbit at different time-points.

Geometric mean titres, at each time point were descriptively summarised, including 95% confidence intervals (CIs). The GMTs and 95% CIs were calculated by back transformations of the confidence limits computed for the mean of the log-transformed titres based on Student's t-distribution (FIG. 5B)

Figure 5B:
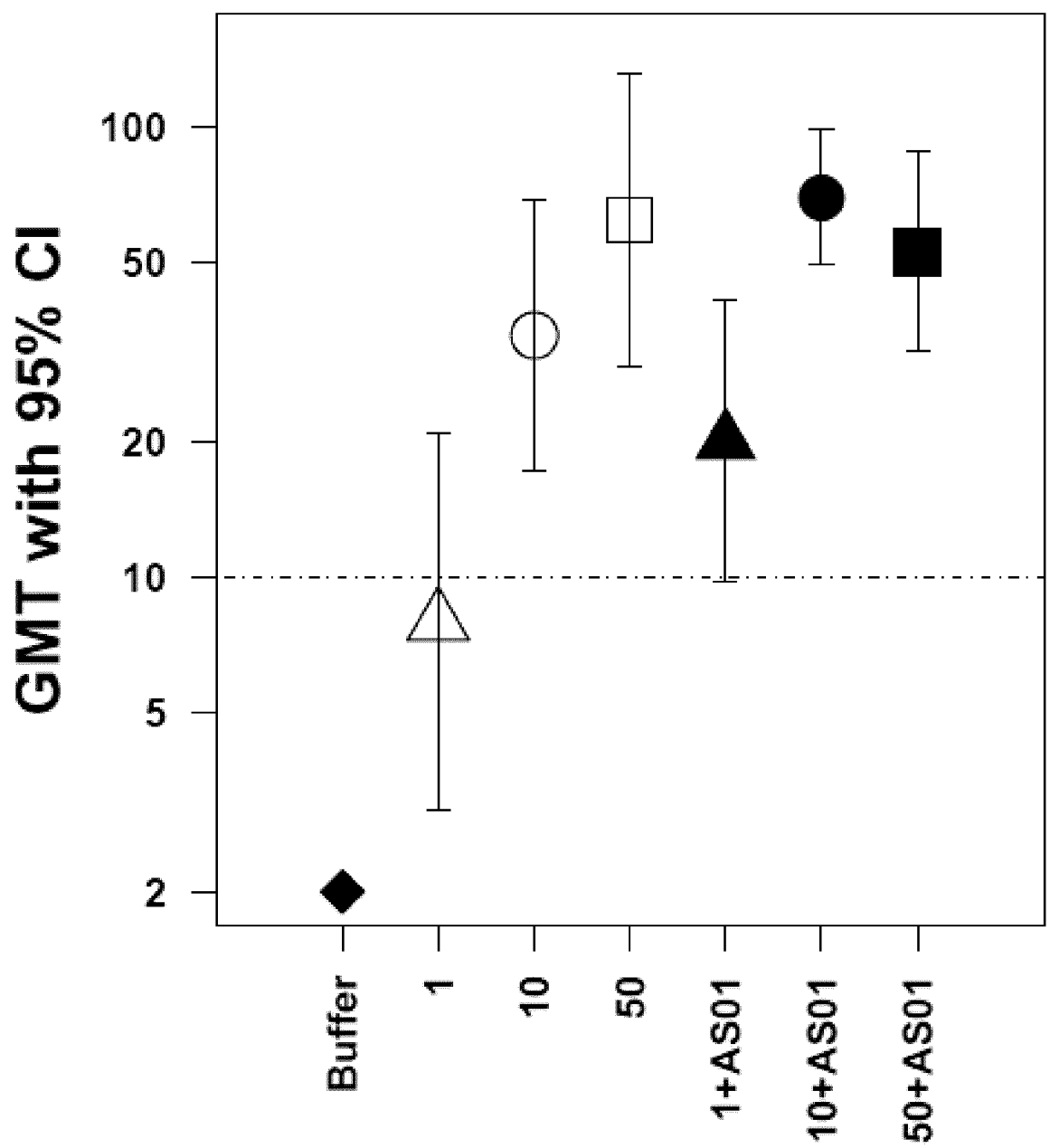
FIG. 5B: Vaccine induces functional IgG neutralising in vitro ClfA activity in pre-exposed rabbits. Neutralisation titres of individual sera were measured pre-vaccination, at 4wp1 and 2wp2. Only at 2wp2 some neutralisation activity is expressed as geometric mean (GMTs) with 95% confidence intervals (CIs). The grey dotted line indicates the reciprocal of the lowest dilution used in the assay. An arbitrary titre of 2 was assigned to non-responders. Triangles: 10 μg dose; Circles: 10 μg dose; squares: 50 μg dose.

The neutralisation results obtained with rabbit sera are shown in FIG. 5B and indicated that: No anti-ClfA functional activity in pre-immune, 4wp1 and Buffer group sera.

Two doses are required to induce ClfA neutralising activity.

The 10 ug dose with adjuvant performs as well as the 50 ug dose without or with adjuvant Overall neutralisation titres are much lower than those measured in mouse sera.

Example 4: CD4 T-Cell Response Versus Vaccine Proteins in Vaccinated Mice

The potential role of pathogen-specific CD4+ T cells in triggering the host immune response against SA is well described. Therefore, the capacity of the vaccine, adjuvanted either with Alum/TLR7 or AS01$_E$, to induce a T cell response in mice was also tested.

In particular the aims of the study were:

See whether immunisation of mice with the vaccine could elicit a T-cell response against the vaccine vaccine proteins (magnitude).

Investigate the Th1, Th2 or Th17 polarization of the response (quality).

Evaluate whether inclusion of an adjuvant in the vaccine formulation improves the magnitude and/or influences the quality of the T cell response.

Compare AS01 and Alum/TLR7 adjuvants for the magnitude and quality of the T-cell response.

To this purpose, five week-old BALB/c female mice were given two immunisations (50 μl in each hind leg quadriceps) at day 1 and 29 by IM route. Two doses of the formulation, vaccine-10 and vaccine-1, consisting of 10 μg or 1 μg (protein-based) of each component were given either alone or with Alum/TLR7 or AS01$_E$ adjuvant. Control groups were injected with PBS, Alum/TLR7 or AS01$_E$ alone. The experiment was repeated 3 times in order to assess experimental variability. An overview of the study with the total number of mice used in the 3 experiments is shown in Table 4.

TABLE 4

Study Design for determination of T cell response in immunised mice

| Group | Total Number of mice | Antigen | Dose protein (μg) | Dose polysaccharides (μg) | Adjuvant[#] | Injection Volume/Route |
|---|---|---|---|---|---|---|
| 1 | 15 | Vaccine | 10 | 2 | none | 100 μl/IM |
| 2 | 15 | Vaccine | 10 | 2 | Alum/TLR7 | 100 μl/IM |
| 3 | 15 | Vaccine | 10 | 2 | AS01$_E$ | 100 μl/IM |
| 4 | 15 | Vaccine | 1 | 0.2 | none | 100 μl/IM |
| 5 | 15 | Vaccine | 1 | 0.2 | Alum/TLR7 | 100 μl/IM |

TABLE 4-continued

Study Design for determination of T cell response in immunised mice

| Group | Total Number of mice | Antigen | Dose protein (µg) | Dose polysaccharides (µg) | Adjuvant[#] | Injection Volume/Route |
|---|---|---|---|---|---|---|
| 6 | 15 | Vaccine | 1 | 0.2 | AS01$_E$ | 100 µl/IM |
| 7 | 6 | Vaccine | — | — | none | 100 µl/IM |
| 8 | 6 | Vaccine | — | — | Alum/TLR7 | 100 µl/IM |
| 9 | 6 | Vaccine | — | — | AS01$_E$ | 100 µl/IM |

The induction of vaccine-specific CD4 T-cell response was evaluated by intracellular cytokine staining (ICS) of splenocytes isolated from single mice 12 days after the second immunisation (d12p2) and then treated in vitro with anti-CD28 and anti-CD49d mAb (2 µg/ml each) alone or together with each vaccine protein (Hla$_{mut}$ and ClfA$_{mut}$ at 10 µg/ml; SpA$_{mut}$ at 1 µg/ml) at 37° C. for 16 h. Brefeldin A, 5 µg/ml, was added for the last 4 h of incubation. Cells were then stained with Live/Dead Nearlr (Invitrogen), fixed and permeabilized with Cytofix/Cytoperm (BD), washed in Perm/Wash buffer (BD), incubated with anti-CD16/CD32 Fc block (BD) for 20 min at RT, and stained with the following mAbs anti:

CD3-BV605, CD4-BV510, CD8-PE-CF594, CD44-V450, IFNγ-BV785, IL-2-PE Cy5, TNF-AF488, IL-17A-PE Cy7, IL-4-PerCP eFluor710, and IL-13-PerCP eFluor710 for 20 min at RT, washed twice in Perm/Wash buffer, and suspended in PBS.

Samples were acquired on a LSRII flow cytometer (BD Biosciences) and CD4 T-cell responses were analysed using FlowJo software (TreeStar).

CD4$^+$CD44$^{high}$ T cells producing IL-2, TNF, IL-4/IL-13, IFN-γ or IL-17A were identified according to a gating strategy.

The magnitude of the T cell response was calculated measuring the frequencies (%) of CD4$^+$CD44$^{high}$ T cells producing at least one of the cytokines analysed in response to in vitro stimulation with vaccine proteins (CD4$^+$CD44$^{high}$ T cells≥1 cytokine$^+$).

The quality of the CD4 T cell response (Th1, Th2 or Th17 polarization) was evaluated measuring the frequencies (%) of CD4$^+$CD44$^{high}$ T cells producing: IFN-γ but not IL-4/IL-13 (≥IFN-γ$^+$, Th1), IL-4/IL-13 but not IFN-γ (≥IL-4/IL-13$^+$, Th2) or at least IL-17A (≥IL-17A$^+$, Th17).

Boolean gates analysis was applied and the response of medium-treated cells was subtracted from that of stimulated cells.

For the analysis of results, a two-way ANOVA was fitted on log$_{10}$ CD4$^+$CD44$^{high}$ percentages including group (9 groups), experiment (3 experiments) and interaction group*experiment as fixed effects and using a heterogeneous variance model (identical variances were not assumed between groups). This model was used to estimate the group geometric means and their 95% CIs as well as geometric mean ratios and their 95% CIs.

Geometric mean ratios above 2-fold were considered as significantly different (p<0.05) if their 95% CIs did not include 1.

The results obtained are illustrated in FIG. 2 in which statistically significant differences are indicated. They can be summarised as follows:

Inclusion of an adjuvant in the vaccine formulation was required to obtain significantly higher frequencies of vaccine-specific T cells as compared to control groups.

AS01 outperformed Alum/TLR7 with each protein antigen.

Only the vaccine adjuvanted with AS01 induced CD4$^+$ T-cells producing IFN-γ (indicating Th1 polarization) specific for each antigen, while Vaccine adjuvanted with Alum/TLR7 induced only SpA$_{mut}$-specific Th1, at significantly lower frequencies.

Very low frequencies of Th2 and Th17 were measured only with AS01 adjuvanted Vaccine.

No major differences in the magnitude and quality of the T-cell response were observed after immunisation either with 1 or 10 µg of unadjuvanted vaccine.

Example 5: Protection in Animal Model: Skin Infection Model

Experiments were carried out in mouse models of *S. aureus* infection to evaluate the efficacy of the 5Ag/AS01$_E$ vaccine (comprising SpA$_{mut}$, ClfA$_{mut}$-CP8 bioconjugate and Hla$_{mut}$-CP5 bioconjugate adjuvanted with AS01$_E$) in protecting against *S. aureus* infection in vivo. The experiments also compared the 5Ag/AS01$_E$ vaccine to a 4Ag/AS01$_E$ vaccine lacking SpA, and the effect of the adjuvant AS01$_E$ in the 5Ag vaccine compared to the 5Ag vaccine adjuvanted with aluminum hydroxide (Al(OH)$_3$). The mouse models used were a skin infection model and a kidney abscess model.

Study Design and Protocol

CD1 mice female 5-week old were used.

For each model three experiments were performed sequentially. A total of 6 experiments were performed, 3 identical studies in the abscess model (Sa-5Ag-7, Sa-5Ag-8, Sa-5Ag-9) and 3 in the skin model (Sa-5Ag-10, Sa-5Ag-11, Sa-5Ag-12). In the skin model, each group was composed of 10 mice, so a total of 30 mice per group was tested in each model.

Mice received two injections given one month apart (at day 0 and day 30) intramuscularly (IM, 30 µl each paw) of one of the different vaccine formulations or PBS.

At 3 weeks after last injection (day 51) mice were infected with an appropriate sub-lethal dose of USA300 bacteria, using the subcutaneous (SC, skin model) infection route. 50 µl of SA USA 300 (theoretical 3×10$^7$ CFU/mouse) was inoculated.

In the skin model, the relevant lesion area was measured 5 days after infection, before being collected 7 days after infection, homogenized and CFU values determined.

TABLE 5

Study design of skin model with S. aureus strain USA 300

| Group (mouse number) | Immunization | | | Infection | | | Readout | |
|---|---|---|---|---|---|---|---|---|
| | Antigen and dose (μg/Ag/mouse) | Adjuvant | Route and volume | Route and volume | Dose (CFU) | | Skin area (days post infection) | |
| | | | | | | | Sizing | Collection |
| 1 (1-10) | PBS | None | IM 60 μl | SC 50 μl | $3 \times 10^7$ | | 5 | 7 |
| 2 (11-20) | Sa-5Ag (10 μg*) | $AS01_E$ | IM 60 μl | SC 50 μl | $3 \times 10^7$ | | 5 | 7 |
| 3 (21-30) | Sa-5Ag (10 μg*) | Al(OH)$_3$ | IM 60 μl | SC 50 μl | $3 \times 10^7$ | | 5 | 7 |
| 4 (31-40) | Sa-4Ag (10 μg*) | $AS01_E$ | IM 60 μl | SC 50 μl | $3 \times 10^7$ | | 5 | 7 |

IM: intramuscular; SC: subcutaneous; $AS01_E$ contains 2.5 μg/dose of MPL and 2.5 μg/dose of QS21; Al(OH)$_3$: Aluminum hydroxide.
*Protein based.

TABLE 6

Schedule of treatments of skin model

| Day | Procedures |
|---|---|
| −1 | Pre-vaccination blood sample collection |
| 0 | $1^{st}$ vaccination |
| 30 | $2^{nd}$ vaccination |
| 50 | Post-$2^{nd}$ vaccination blood sample collection |
| 51 | Subcutaneous infection (USA300) |
| 56 | Lesion area quantitation |
| 58 | Mice sacrifice, collection of the skin lesion area and CFU determination |

Materials and Methods

Bacterial Aliquot Preparation for Storing at −80° C.

20 ml fresh Tryptic Soy Broth (TSB) (prewarmed at 37° C. overnight or at least 1 h before use) was mixed with 0.3 ml of thawed bacteria (old stock) in 50 ml disposable tube. Initial $OD_{600\ nm}$ was 0.03 and bacteria were grown until $OD_{600\ nm}$=0.55. 2 ml of this bacterial suspension was aliquoted in cryovials and stored at −80° C.

Growth Conditions

A stock of bacteria (S. aureus USA300) from −80° C. freezer, prepared as described above, was thawed in a water bath at 37° C. for 10 min. 20 ml fresh Tryptic Soy Broth (TSB) (prewarmed at 37° C. overnight or at least 1 h before to use) was mixed with 0.3 ml of thawed bacteria. Initial $OD_{600\ nm}$ was 0.03 and bacteria were grown in 50 ml disposable tube. Bacteria were incubated about for 2.0 hours at 37° C., 150 rpm agitation until a final $OD_{600\ nm}$ of 0.6, then centrifuged at 4500 rpm, 10 minutes, 4° C. Supernatant was removed and the pellet resuspended in equal volume of PBS and again centrifuged at 4500 rpm, 10 minutes, 4° C. The supernatant was again removed and the bacterial pellet resuspended in 2 ml of PBS (around $5 \times 10^9$ cfu/ml). At this point, a final dilution was made to reach a bacterial concentration of $3 \times 10^7$ cfu/mouse in 50 μl. 100 μl of final bacterial suspension was diluted and $10^{-5}$ and $10^{-6}$ dilutions plated onto Tryptic Soy Agar (TSA) plates to count CFU.

In Vivo Model of Subcutaneous Infection with S. aureus

The day before infection, anaesthetised mice (Zolazepam+Tiletamina/Xylazine) were shaved in dorsal position using electric razor and depilatory cream. The depilatory cream was removed gently by water at 37° C. Bacteria, prepared as described before, were inoculated subcutaneously (50 μl/animal) in mice anaesthetised with Zolazepam+Tiletamina/Xylazine. Animals were followed every day using a dedicated score sheet for clinical symptoms of disease. Pictures of lesions to determine dimension were taken at days 5 post infection with a digital camera. Seven days after infection, mice were sacrificed and the skin with lesion removed using circular scalpel (8 mm); for larger lesions scissors were used to ensure entire lesion recovered. The removed skin was homogenised for CFU counts. Decimal dilutions were prepared up to $10^{-8}$ and 10 μl spots (in duplicate) plated onto TSA plates.

Readouts of the Model

Skin lesion area at days 5: expressed in mm$^2$ measured by ImageJ software.

Clinical score registered every day after infection.

CFU counts (expressed as CFU/sample) at day 7 post infection.

Results

The 5Ag+$AS01_E$ vaccine was effective in preventing skin lesions and reducing CFU counts.

At 5 days after the skin infection none of the mice vaccinated with 5Ag+$AS01_E$ exhibited a skin lesion. 17% of the mice (5/30) vaccinated with 5Ag+Al(OH)$_3$ exhibited a skin lesion while 60% (18/30) and 100% (30/30) of mice vaccinated with 4Ag+$AS01_E$ and PBS respectively, showed a skin lesion. Results are shown in Tables 7-9.

The CFU GM at 7 days after the infection, in the SA vaccine formulation without SpA antigen (Sa-4Ag+$AS01_E$) was almost 3-fold higher (2.84-fold) than in the Sa vaccine formulation with SpA (Sa-5Ag+$AS01_E$) and the difference was statistically significant (the 95% CI of CFU GMs vaccine group ratio between the two vaccine groups didn't include the value 1) (Tables 7 and 8).

There was a difference in the level of viable bacteria in skin between the two Sa-5Ag vaccine formulation adjuvanted with $AS01_E$ or with Al(OH)$_3$, but the difference was not statistically significant. The CFU GM, was 1.6-fold higher in the Sa-5Ag vaccine formulation with Al(OH)$_3$ as adjuvant [Sa-5Ag+Al(OH)$_3$] than the vaccine Sa-5Ag vaccine formulation with $AS01_E$ (Sa-5Ag+$AS01_E$) as adjuvant and the 95% CI of CFU GMs vaccine group ratio included the value 1 (Tables 7 and 8).

In the PBS alone group the level of viable bacteria in skin at 7 days after infection was significantly higher than the level observed in any of the vaccine formulations evaluated. The CFU GM in the PBS group was 40.32- to 114.48-fold higher than the CFU GMs observed in the vaccine formulations. (Tables 7 and 8).

Explorative pairwise comparisons of the median of two groups, performed using a two-sample median test, showed a significative difference between the vaccine formulations with and without SpA (p<0.0001) and between the Sa-5Ag vaccine formulations with $ASO1_E$ and $Al(OH)_3$ (p=0.0206).

TABLE 7

Skin model-CFU Geometric mean and 95% Cl at 4 days after infection with *S. aureus* strain USA 300

| Group Label | Group | N | CFU Geometric Mean | 95% Cl-Lower Limit | 95% Cl-Upper Limit |
|---|---|---|---|---|---|
| PBS | 1 | 30 | 144660225 | 85736457 | 244080306 |
| Sa-5Ag + $ASO1_E$ | 2 | 30 | 1263656 | 748937 | 2132125 |
| Sa-5Ag + $Al(OH)_3$ | 3 | 30 | 2037202 | 1207398 | 3437302 |
| Sa-4Ag + $ASO1_E$ | 4 | 30 | 3587442 | 2126186 | 6052970 |

TABLE 8

Skin model-CFU GM vaccine group ratio and 95% Cl at 4 days after infection with *S. aureus* strain USA 300

| Comparison | Ratio of Geometric Mean | 95% Cl-Lower Limit | 95% Cl-Upper Limit | Statistically significant* |
|---|---|---|---|---|
| Gr1 PBS/Gr2 Sa-5Ag + $ASO1_E$ | 114.48 | 54.63 | 239.89 | v |
| Gr1 PBS/Gr3 Sa-5Ag + $Al(OH)_3$ | 71.01 | 33.89 | 148.80 | v |
| Gr1 PBS/GT4 Sa-4Ag + $ASO1_E$ | 40.32 | 19.24 | 84.50 | v |
| GT4 Sa-4Ag + $ASO1_E$/Gr2 Sa-5Ag + $ASO1_E$ | 2.84 | 1.35 | 5.95 | v |
| Gr3 Sa-5Ag + $Al(OH)_3$/ Gr2 Sa-5Ag + $ASO1_E$ | 1.61 | 0.77 | 3.38 | — |

*When the 95% CI of the GM Ratio does not include the value 1 (i.e., equal GMs) then the difference is statistically significant. In particular, if the 95% CI-Lower limit of the ratio of GM between two groups is >1, the first component is considered statistically significantly higher than the second component of the comparison. Vice versa, if the 95% CI-Upper limit of the ratio of GM between two groups is <1, the first component is considered statistically significantly lower than the second component of the comparison. The symbol v indicates a statistically significant comparison.

TABLE 9

Skin model-Mean, Median, Min, Max of lesion area by group*

| Group | N | Mean lesion area | Median lesion area | Min lesion area | Max lesion area |
|---|---|---|---|---|---|
| Gr1 PBS | 30 | 19.07 | 14.00 | 2.30 | 66.00 |
| Gr2 Sa-5Ag + AS01 | 30 | 0.10 | 0.10 | 0.10 | 0.10 |
| Gr3 Sa-5Ag + AlOH | 30 | 0.39 | 0.10 | 0.10 | 2.30 |
| GT4 Sa-4Ag + AS01 | 30 | 1.08 | 0.80 | 0.10 | 3.70 |

*No lesion area was set to 0.1 for the purpose of the analysis.

CFU could be measured also in mice who did not show any skin lesion, since bacteria are also present in subcutaneous abscesses. In the two vaccine formulations where a subset of mice showed no lesion and the remaining mice in the group showed a lesion (i.e., groups 5Ag+$Al(OH)_3$ and 4Ag+$ASO1_E$) the mean and median CFU count in the skin was lower in the mice with no lesion area than in the mice with a lesion. For each vaccine group, descriptive statistics (mean, median, min, max) of CFU count by presence or absence of lesion area are shown in Table 10.

TABLE 10

Skin model - Mean, Median, Min, Max of CFU count

| Group | Presence of lesion | N | Mean CFU count | Median CFU count | Min CFU count | Max CFU count |
|---|---|---|---|---|---|---|
| Gr1 PBS | Yes Lesion | 30 | 578366667 | 107500000 | 5500000 | 7000000000 |
| Gr2 Sa-5Ag + AS01 | No Lesion | 30 | 2764000 | 1675000 | 85000 | 10500000 |
| Gr3 Sa-5Ag + AlOH | No Lesion | 25 | 2776600 | 2150000 | 80000 | 11500000 |
| Gr3 Sa-5Ag + AlOH | Yes Lesion | 5 | 9500000 | 10500000 | 4000000 | 14500000 |
| Gr4 Sa-4Ag + AS01 | No Lesion | 12 | 2584583 | 2025000 | 365000 | 8500000 |
| Gr4 Sa-4Ag + AS01 | Yes Lesion | 18 | 17522222 | 6950000 | 750000 | 195000000 |

Example 6: Protection in Animal Models: Kidney Abscess Model

Experiments were carried out in a kidney abscess mouse model, as a model of systemic infection, to evaluate the efficacy of the 5Ag/$ASO1_E$ vaccine in protecting against *S. aureus* infection in vivo, as described at Example 5 above.

Protocol and Study Design

CD1 mice female 5-week old were used.

For each model three experiments were performed sequentially. A total of 6 experiments were performed, 3 identical studies in the abscess model (Sa-5Ag-7, Sa-5Ag-8, Sa-5Ag-9). Each group was composed of 12 mice, so a total of 36 mice was tested in each model.

Mice received two injections given one month apart (at day 0 and day 30) intramuscularly (IM, 30 µl each paw) of one of the different vaccine formulations or PBS.

At 3 weeks after last injection (day 51) mice were infected with an appropriate sub-lethal dose of USA300 bacteria, using the intravenous (IV, kidney abscess model) infection route.

100 µl of SA USA 300 (theoretical $1 \times 10^7$ CFU/mouse) strain was inocuated.

The infected mice were sacrificed 4 days post-infection, kidneys were collected, homogenised and CFU number was counted.

TABLE 11

Study design of abscess model with *S. aureus* strain USA 300

| Group (mouse number) | Immunization | | | Infection route and volume | | Kidney collection |
|---|---|---|---|---|---|---|
| | Antigen dose (µg/Ag/mouse) | Adjuvant | Route and volume | Route and volume | Infection dose (CFU)** | (days post-infection) |
| 1 (1-12) | PBS | None | IM 60 µl | IV 100 µl | $1 \times 10^7$ | 4 |
| 2 (13-24) | Sa-5 Ag (10 µg*) | AS01$_E$ | IM 60 µl | IV 100 µl | $1 \times 10^7$ | 4 |
| 3 (25-36) | Sa-5 Ag (10 µg*) | Al(OH)$_3$ | IM 60 µl | IV 100 µl | $1 \times 10^7$ | 4 |
| 4 (37-48) | Sa-4 Ag (10 µg*) | AS01$_E$ | IM 60 µl | IV 100 µl | $1 \times 10^7$ | 4 |

IM: intramuscular; IV: intravenous; AS01$_E$ contains 2.5 µg/dose of MPL and 2.5 µg/dose of QS21; Al(OH)$_3$: Aluminum hydroxide
*Protein based.

TABLE 12

Schedule of treatments of abscess model

| Day | Procedures |
|---|---|
| −1 | Pre-vaccination blood sample collection |
| 0 | 1$^{st}$ vaccination |
| 30 | 2$^{nd}$ vaccination |
| 50 | Post-2$^{nd}$ vaccination blood sample collection |
| 51 | Intravenous infection (1X10$^7$) |
| 55 | Mice sacrificed 4 days after infection, with collection of kidneys and CFU count |

Materials and Methods

Bacterial Aliquot Preparation for Storing at −80° C.

20 ml fresh Tryptic Soy Broth (TSB) (prewarmed at 37° C. overnight or at least 1 h before use) was mixed with 0.3 ml of thawed bacteria (old stock) in 50 ml disposable tube. Initial OD$_{600\ nm}$ is 0.03 and bacteria were grown until OD$_{600\ nm}$=0.55. 2 ml of this bacterial suspension was aliquoted in cryovials and stored at −80° C.

Growth Conditions

A stock of bacteria (*S. aureus* USA300) from −80° C. freezer, prepared as described above, was thawed in a water bath at 37° C. for 10 min. 20 ml fresh Tryptic Soy Broth (TSB) (prewarmed at 37° C. overnight or at least 1 h before use) was mixed with 0.3 ml of thawed bacteria. Initial OD$_{600\ nm}$ was 0.03 and bacteria grown in 50 ml disposable tube. Bacteria were incubated about for 2.0 hours at 37° C., 150 rpm agitation to reach a final OD$_{600\ nm}$ of 0.6. Bacteria were centrifuged at 4500 rpm, 10 minutes, 4° C. Supernatant was removed and the pellet resuspended in equal volume of PBS and again centrifuged at 4500 rpm, 10 minutes, 4° C. Supernatant was again removed and the bacterial pellet resuspended in 2 ml of PBS (around 5×10$^9$ cfu/ml). At this point, a final dilution was made to reach a bacterial concentration of 1×10$^7$ cfu/mouse in 100 µl. 100 µl of final bacterial suspension was diluted and 10$^{-5}$ and 10$^{-6}$ dilutions plated onto Tryptic Soy Agar (TSA) plates to count CFU.

In Vivo Model of Subcutaneous Infection with *S. aureus*

Mice were warmed using an infrared lamp in order to inflate the tail veins. Bacteria, prepared as described above, were inoculated intravenously (100 µl/animal) into the tail vein. Animals were followed every day using a dedicated score sheet for clinical symptoms of disease. Four days after infection, mice were sacrificed and the kidneys recovered. The removed kidneys were homogenised for CFU counts (2 ml PBS). Decimal dilutions were prepared up to 10$^{-8}$ and 10 µl spots (in duplicate) are plated onto TSA plates.

Readouts of the Model

Clinical score registered every day after infection.

CFU counts (expressed as CFU/sample) at day 4 post infection.

Results

The 5Ag+AS01$_E$ vaccine was highly effective in reducing bacterial infection compared to control. The level of viable bacteria in kidney collected at 4 days after the infection, as measured by CFU geometric mean (GM), in the vaccine formulation without the SpA antigen (Sa-4Ag+AS01$_E$) was 6.6-fold higher than in the SA vaccine formulation with SpA (Sa-5Ag+AS01$_E$) and the difference was statistically significant. The CFU GM, was almost 2-fold higher (1.78-fold) in the Sa-5Ag vaccine formulation with Al(OH)$_3$ as adjuvant [Sa-5Ag+Al(OH)$_3$] than in the vaccine Sa-5Ag vaccine formulation with AS01$_E$ as adjuvant (Sa-5Ag+AS01$_E$), but this difference was not statistically significant. In the PBS alone group the level of viable bacteria in kidney at 4 days after infection was at least 4-fold higher than the level observed in any GSK Sa vaccine formulation evaluated in the studies. The results are shown in Table 13.

TABLE 13

Kidney abscess model-CFU Geometric mean and 95% CI at 4 days after infection with *S. aureus* strain USA 300

| Group Label | Group | Number | CFU Geometric Mean* | 95% CI-Lower Limit | 95% CI-Upper Limit |
|---|---|---|---|---|---|
| PBS | 1 | 36 | 93010566 | 60102858 | 143936005 |
| Sa-5Ag + AS01$_E$ | 2 | 36 | 3257105 | 1563051 | 6787196 |
| Sa-5Ag + Al(OH)$_3$ | 3 | 36 | 5811332 | 3119367 | 10826419 |
| Sa-4Ag + AS01$_E$ | 4 | 36 | 21491537 | 12673064 | 36446289 |

*CFU GMs are unadjusted GMs.

SEQUENCE LISTING

SEQ ID NO: 1-Wild-type ClfAN1N2N3
ASENSVTQSDSASNESKSNDSSSVSAAPKTDDTNVSDTKTSSNTNNGETSVAQNPAQQETTQSSSTNATTEETPV
TGEATTTTTNQANTPATTQSSNTNAEELVNQTSNETTFNDTNTVSSVNSPQNSTNAENVSTTQDTSTEATPSNNE
SAPQSTDASNKDVVNQAVNTSAPRMRAFSLAAVAADAPAAGTDITNQLTNVTVGIDSGTTVYPHQAGYVKLNYGF
SVPNSAVKGDTFKITVPKELNLNGVTSTAKVPPIMAGDQVLANGVIDSDGNVIYTFTDYVNTKDDVKATLTMPAY

SEQUENCE LISTING

IDPENVKKTGNVTLATGIGSTTANKTVLVDYEKYGKFYNLSIKGTIDQIDKTNNTYRQTIYVNPSGDNVIAPVLT
GNLKPNTDSNALIDQQNTSIKVYKVDNAADLSESYFVNPENFEDVTNSVNITFPNPNQYKVEFNTPDDQITTPYI
VVVNGHIDPNSKGDLALRSTLYGYNSNIIWRSMSWDNEVAFNNGSGSGDGIDKPVVPEQPDEPGEIEPIPED

SEQ ID NO: 2-Wild-type ClfAN2N3
VAADAPAAGTDITNQLTNVTVGIDSGTTVYPHQAGYVKLNYGFSVPNSAVKGDTFKITVPKELNLNGVTSTAKVP
PIMAGDQVLANGVIDSDGNVIYTFTDYVNTKDDVKATLTMPAYIDPENVKKTGNVTLATGIGSTTANKTVLVDYE
KYGKFYNLSIKGTIDQIDKTNNTYRQTIYVNPSGDNVIAPVLTGNLKPNTDSNALIDQQNTSIKVYKVDNAADLS
ESYFVNPENFEDVTNSVNITFPNPNQYKVEFNTPDDQITTPYIVVVNGHIDPNSKGDLALRSTLYGYNSNIIWRS
MSWDNEVAFNNGSGSGDGIDKPVVPEQPDEPGEIEPIPED SEQ ID NO: 3-Mature wild-type Hla
ADSDINIKTGTTDIGSNTTVKTGDLVTYDKENGMHKKVFYSFIDDKNHNKKLLVIRTKGTIAGQYRVYSEEGANK
SGLAWPSAFKVQLQLPDNEVAQISDYYPRNSIDTKEYMSTLTYGFNGNVTGDDTGKIGGLIGANVSIGHTLKYVQ
PDFKTILESPTDKKVGWKVIFNNMVNQNWGPYDRDSWNPVYGNQLFMKTRNGSMKAADNFLDPNKASSLLSSGFS
PDFATVITMDRKASKQQTNIDVIYERVRDDYQLHWTSTNWKGTNTKDKWIDRSSERYKIDWEKEEMTN SEQ ID NO: 4-WILD-TYPE SpA. Underlined are the QQ and DD residues which may be mutated to
reduce Fcγ and VH3 binding respectively
MKKKNIYSIRKLGVGIASVTLGTLLISGGVTPAANAAQHDEA<u>QQ</u>NAFYQVLNMPNLNADQRNGFIQSLK<u>DD</u>PSQS
ANVLGEAQKLNDSQAPKADA<u>QQ</u>NNFNKD<u>QQ</u>SAFYEILNMPNLNEAQRNGFIQSLK<u>DD</u>PSQSTNVLGEAKKLNESQ
APKADNNFNKE<u>QQ</u>NAFYEILNMPNLNEEQRNGFIQSLK<u>DD</u>PSQSANLLSEAKKLNESQAPKADNKFNKE<u>QQ</u>NAFY
EILNMPNLNEEQRNGFIQSLK<u>DD</u>PSQSANLLAEAKKLNDAQAPKADNKFNKE<u>QQ</u>NAFYEILHLPNLTEEQRNGFI
QSLK<u>DD</u>PSVSKEILAEAKKLNDAQAPKEEDNNKPGKEDNNKPGKEDNNKPGKEDGNKPGKEDGNKPGKEDGNKPG
KEDNKKPGKEDGNKPGKEDNKKPGKEDGNKPGKEDGNKPGKEDGNGVHVVKPGDTVNDIAKANGTTADKIAADNK
LADKNMIKPGQELVVDKKQPANHADANKAQALPETGEENPFIGTTVFGGLSLALGAALLAGRRREL SEQ ID NO: 5-ClfA N2N3 P116S/Y118A
VAADAPAAGTDITNQLTNVTVGIDSGTTVYPHQAGYVKLNYGFSVPNSAVKGDTFKITVPKELNLNGVTSTAKVP
PIMAGDQVLANGVIDSDGNVIYTFTDYVNTKDDVKATLTMSAAIDPENVKKTGNVTLATGIGSTTANKTVLVDYE
KYGKFYNLSIKGTIDQIDKTNNTYRQTIYVNPSGDNVIAPVLTGNLKPNTDSNALIDQQNTSIKVYKVDNAADLS
ESYFVNPENFEDVTNSVNITFPNPNQYKVEFNTPDDQITTPYIVVVNGHIDPNSKGDLALRSTLYGYNSNIIWRS
MSWDNEVAFNNGSGSGDGIDKPVVPEQPDEPGEIEPIPED SEQ ID NO: 6-ClfA N2N3 P116S/Y118A with PglB consensus sequence (KDQNATK, underlined)
substituted for residue I337
VAADAPAAGTDITNQLTNVTVGIDSGTTVYPHQAGYVKLNYGFSVPNSAVKGDTFKITVPKELNLNGVTSTAKVP
PIMAGDQVLANGVIDSDGNVIYTFTDYVNTKDDVKATLTMSAAIDPENVKKTGNVTLATGIGSTTANKTVLVDYE
KYGKFYNLSIKGTIDQIDKTNNTYRQTIYVNPSGDNVIAPVLTGNLKPNTDSNALIDQQNTSIKVYKVDNAADLS
ESYFVNPENFEDVTNSVNITFPNPNQYKVEFNTPDDQITTPYIVVVNGHIDPNSKGDLALRSTLYGYNSNIIWRS
MSWDNEVAFNNGSGSGDGIDKPVVPEQPDEPGEIEPKDQNATKPED SEQ ID NO: 7-ClfA N2N3 P116S/Y118A with PglB consensus sequence (KDQNATK, underlined)
substituted for residue I337 and N-terminal S
SVAADAPAAGTDITNQLTNVTVGIDSGTTVYPHQAGYVKLNYGFSVPNSAVKGDTFKITVPKELNLNGVTSTAKV
PPIMAGDQVLANGVIDSDGNVIYTFTDYVNTKDDVKATLTMSAAIDPENVKKTGNVTLATGIGSTTANKTVLVDY
EKYGKFYNLSIKGTIDQIDKTNNTYRQTIYVNPSGDNVIAPVLTGNLKPNTDSNALIDQQNTSIKVYKVDNAADL
SESYFVNPENFEDVTNSVNITFPNPNQYKVEFNTPDDQITTPYIVVVNGHIDPNSKGDLALRSTLYGYNSNIIWR
SMSWDNEVAFNNGSGSGDGIDKPVVPEQPDEPGEIEPKDQNATKPED SEQ ID NO: 8-Mature Hla H35L
ADSDINIKTGTTDIGSNTTVKTGDLVTYDKENGMLKKVFYSFIDDKNHNKKLLVIRTKGTIAGQYRVYSEEGANK
SGLAWPSAFKVQLQLPDNEVAQISDYYPRNSIDTKEYMSTLTYGFNGNVTGDDTGKIGGLIGANVSIGHTLKYVQ
PDFKTILESPTDKKVGWKVIFNNMVNQNWGPYDRDSWNPVYGNQLFMKTRNGSMKAADNFLDPNKASSLLSSGFS
PDFATVITMDRKASKQQTNIDVIYERVRDDYQLHWTSTNWKGTNTKDKWIDRSSERYKIDWEKEEMTN SEQ ID NO: 9-Mature Hla H35L with PglB consensus sequence (KDQNRTK) substituted for residue
K131
ADSDINIKTGTTDIGSNTTVKTGDLVTYDKENGMLKKVFYSFIDDKNHNKKLLVIRTKGTIAGQYRVYSEEGANK
SGLAWPSAFKVQLQLPDNEVAQISDYYPRNSIDTKEYMSTLTYGFNGNVTGDDTKDQNRTKIGGLIGANVSIGH
TLKYVQPDFKTILESPTDKKVGWKVIFNNMVNQNWGPYDRDSWNPVYGNQLFMKTRNGSMKAADNFLDPNKASSL
LSSGFSPDFATVITMDRKASKQQTNIDVIYERVRDDYQLHWTSTNWKGTNTKDKWIDRSSERYKIDWEKEEMTN SEQ ID NO: 10-Mature Hla H35L/H48C/G122C
ADSDINIKTGTTDIGSNTTVKTGDLVTYDKENGMLKKVFYSFIDDKNCNKKLLVIRTKGTIAGQYRVYSEEGANK
SGLAWPSAFKVQLQLPDNEVAQISDYYPRNSIDTKEYMSTLTYGFNCNVTGDDTGKIGGLIGANVSIGHTLKYVQ
PDFKTILESPTDKKVGWKVIFNNMVNQNWGPYDRDSWNPVYGNQLFMKTRNGSMKAADNFLDPNKASSLLSSGFS
PDFATVITMDRKASKQQTNIDVIYERVRDDYQLHWTSTNWKGTNTKDKWIDRSSERYKIDWEKEEMTN SEQ ID NO: 11-Mature Hla H35L/H48C/G122C with PglB consensus sequence (KDQNRTK)
substituted for residue K131
ADSDINIKTGTTDIGSNTTVKTGDLVTYDKENGMLKKVFYSFIDDKNCNKKLLVIRTKGTIAGQYRVYSEEGANK
SGLAWPSAFKVQLQLPDNEVAQISDYYPRNSIDTKEYMSTLTYGFNCNVTGDDTKDQNRTKIGGLIGANVSIGH
TLKYVQPDFKTILESPTDKKVGWKVIFNNMVNQNWGPYDRDSWNPVYGNQLFMKTRNGSMKAADNFLDPNKASSL
LSSGFSPDFATVITMDRKASKQQTNIDVIYERVRDDYQLHWTSTNWKGTNTKDKWIDRSSERYKIDWEKEEMTN

SEQUENCE LISTING

SEQ ID NO: 12-Hla H35L/H48C/G122C with N-terminal S, C-terminal GSHRHR, and KDQNRTK substituted for residue K131
SADSDINIKTGTTDIGSNTTVKTGDLVTYDKENGMLKKVFYSFIDDKNCNKKLLVIRTKGTIAGQYRVYSEEGAN
KSGLAWPSAFKVQLQLPDNEVAQISDYYPRNSIDTKEYMSTLTYGFNCNVTGDDTGKDQNRTKIGGLIGANVSIG
HTLKYVQPDFKTILESPTDKKVGWKVIFNNMVNQNWGPYDRDSWNPVYGNQLFMKTRNGSMKAADNFLDPNKASS
LLSSGFSPDFATVITMDRKASKQQTNIDVIYERVRDDYQLHWTSTNWKGTNTKDKWIDRSSERYKIDWEKEEMTN
GSHRHR SEQ ID NO: 13-SpA IgG binding portion (domains E, D, A, B, C). Underlined are the QQ and DD residues which may be mutated to reduce Fcγ and VH$_3$ binding respectively.
AQHDEAQQNAFYQVLNMPNLNADQRNGFIQSLKDDPSQSANVLGEAQKLNDSQAPKADAQQNNFNKDQQSAFYEI
LNMPNLNEAQRNGFIQSLKDDPSQSTNVLGEAKKLNESQAPKADNNFNKEQQNAFYEILNMPNLNEEQRNGFIQS
LKDDPSQSANLLSEAKKLNESQAPKADNKFNKEQQNAFYEILHLPNLNEEQRNGFIQSLKDDPSQSANLLAEAKK
LNDAQAPKADNKFNKEQQNAFYEILHLPNLTEEQRNGFIQSLKDDPSVSKEILAEAKKLNDAQAPK SEQ ID NO: 14-SpA E domain. Underlined are the QQ and DD residues which may be mutated to reduce Fcγ and VH$_3$ binding respectively
AQHDEAQQNAFYQVLNMPNLNADQRNGFIQSLKDDPSQSANVLGEAQKLNDSQAPK SEQ ID NO: 15-SpA D domain. Underlined are the QQ and DD residues which may be mutated to reduce Fcγ and VH$_3$ binding respectively
ADAQQNNFNKDQQSAFYEILNMPNLNEAQRNGFIQSLKDDPSQSTNVLGEAKKLNESQAPK SEQ ID NO: 16-SpA A domain. Underlined are the QQ and DD residues which may be mutated to reduce Fcγ and VH$_3$ binding respectively
ADNNFNKEQQNAFYEILNMPNLNEEQRNGFIQSLKDDPSQSANLLSEAKKLNESQAPK SEQ ID NO: 17-SpA B domain. Underlined are the QQ and DD residues which may be mutated to reduce Fcγ and VH$_3$ binding respectively
ADNKFNKEQQNAFYEILHLPNLNEEQRNGFIQSLKDDPSQSANLLAEAKKLNDAQAPK SEQ ID NO: 18-SpA C domain. Underlined are the QQ and DD residues which may be mutated to reduce Fcγ and VH$_3$ binding respectively
ADNKFNKEQQNAFYEILHLPNLTEEQRNGFIQSLKDDPSVSKEILAEAKKLNDAQAPK SEQ ID NO: 19-SpA E domain with QQ-KK substitutions at positions 7 and 8 and DD-AA substitutions at positions 34 and 35
AQHDEAKKNAFYQVLNMPNLNADQRNGFIQSLKAAPSQSANVLGEAQKLNDSQAPK SEQ ID NO: 20-SpA D domain with QQ-KK substitutions at positions 12 and 13 and DD-AA substitutions at positions 39 and 40
ADAQQNNFNKDKKSAFYEILNMPNLNEAQRNGFIQSLKAAPSQSTNVLGEAKKLNESQAPK SEQ ID NO: 21-SpA A domain with QQ-KK substitutions at positions 9 and 108 and DD-AA substitutions at positions 36 and 37
ADNNFNKEKKNAFYEILNMPNLNEEQRNGFIQSLKAAPSQSANLLSEAKKLNESQAPK SEQ ID NO: 22-SpA B domain with QQ-KK substitutions at positions 9 and 10 and DD-AA substitutions at positions 36 and 37
ADNKFNKEKKNAFYEILHLPNLNEEQRNGFIQSLKAAPSQSANLLAEAKKLNDAQAPK SEQ ID NO: 23-SpA C domain with QQ-KK substitutions at positions 9 and 10 and DD-AA substitutions at positions 36 and 37
ADNKFNKEKKNAFYEILHLPNLTEEQRNGFIQSLKAAPSVSKEILAEAKKLNDAQAPK SEQ ID NO: 24-SpA D domain with QQ-KR substitutions at positions 4 and 5, QQ-KK substitutions at positions 12 and 13 and DD-AA substitutions at positions 39 and 40
ADAKRNNFNKDKKSAFYEILNMPNLNEAQRNGFIQSLKAAPSQSTNVLGEAKKLNESQAPK SEQ ID NO: 25-SpA D domain with QQ-KR substitutions at positions 4 and 5
ADAKRNNFNKDQQSAFYEILNMPNLNEAQRNGFIQSLKDDPSQSTNVLGEAKKLNESQAPK SEQ ID NO: 26-SpA IgG binding portion (EDABC domains) with the substitutions of SEQ ID NOs 19-23 (SpA$_{KKAA}$)
AQHDEAKKNAFYQVLNMPNLNADQRNGFIQSLKAAPSQSANVLGEAQKLNDSQAPKADAQQNNFNKDK
KSAFYEILNMPNLNEAQRNGFIQSLKAAPSQSTNVLGEAKKLNESQAPKADNNFNKEKKNAFYEILNM
PNLNEEQRNGFIQSLKAAPSQSANLLSEAKKLNESQAPKADNKFNKEKKNAFYEILHLPNLNEEQRNG
FIQSLKAAPSQSANLLAEAKKLNDAQAPKADNKFNKEKKNAFYEILHLPNLTEEQRNGFIQSLKAAPS
VSKEILAEAKKLNDAQAPK SEQ ID NO: 27-SpA IgG binding portion (EDABC domains) with the substitutions of SEQ ID NOs 19 and 21-24 (SpA$_{KKAA-KR}$)
AQHDEAKKNAFYQVLNMPNLNADQRNGFIQSLKAAPSQSANVLGEAQKLNDSQAPKADAKRNNFNKDK
KSAFYEILNMPNLNEAQRNGFIQSLKAAPSQSTNVLGEAKKLNESQAPKADNNFNKEKKNAFYEILNM
PNLNEEQRNGFIQSLKAAPSQSANLLSEAKKLNESQAPKADNKFNKEKKNAFYEILHLPNLNEEQRNG
FIQSLKAAPSQSANLLAEAKKLNDAQAPKADNKFNKEKKNAFYEILHLPNLTEEQRNGFIQSLKAAPS -continued

SEQUENCE LISTING

VSKEILAEAKKLNDAQAPK

SEQ ID NO: 28-PglB consensus sequence
D/E-X-N-Z-S/T

SEQ ID NO: 29-PglB consensus sequence
K-D/E-X-N-Z-S/T-K

SEQ ID NO: 30-PglB consensus sequence
K-D-Q-N-R-T-K

SEQ ID NO: 1-PglB consensus sequence
K-D-Q-N-A-T-K

SEQ ID NO: 32-ClfAN2N3P116S/Y118A with (underlined) at I337, N-terminal S, C-terminal GS
SVAADAPAAGTDITNQLTNVTGIDSGTTVYPHQAGYVKLNYGFSVPNSAVKGDTFKITVPKELNLNGVTSTAKV
PPIMAGDQVLANGVIDSDGNVIYTFTDYVNTKDDVKATLTMSAAIDPENVKKTGNVTLATGIGSTTANKTVLVDY
EKYGKFYNLSIKGTIDQIDKTNNTYRQTIYVNPSGDNVIAPVLTGNLKPNTDSNALIDQQNTSIKVYKVDNAADL
SESYFVNPENFEDVTNSVNITFPNPNQYKVEFNTPDDQITTPYIVVVNGHIDPNSKGDLALRSTLYGYNSNIIWR
SMSWDNEVAFNNGSGSGDGIDKPVVPEQPDEPGEIEPKDQNATKPEDGS

The invention claimed is:

1. An immunogenic composition comprising
   a. a clumping factor A (ClfA) antigen comprising an amino acid sequence at least 95% identical to SEQ ID NO: 32, wherein the ClfA antigen comprises a serine at a position equivalent to P116 of SEQ ID NO: 2; an alanine at a position equivalent to Y118 of SEQ ID NO: 2, and the sequence KDQNATK (SEQ ID NO: 31) beginning at a position equivalent to I337 of SEQ ID NO: 2;
   b. an alpha-haemolysin (Hla) antigen comprising an amino acid sequence at least 95% identical to SEQ ID NO: 12, wherein the Hla antigen comprises a leucine at a position equivalent to H35 of SEQ ID NO: 3, a cysteine at a position equivalent to H48 of SEQ ID NO: 3, a cysteine at a position equivalent to G122 of SEQ ID NO: 3, and the sequence KDQNRTK (SEQ ID NO: 30) beginning at a position equivalent to K131 of SEQ ID NO: 3; and
   c. a Staphylococcal protein A (SpA) antigen comprising an amino acid sequence at least 95% identical to SEQ ID NO: 27, wherein the SpA antigen comprises a lysine at positions equivalent to positions Q43, Q44, Q96, Q104, Q105, Q162, Q163, Q220, Q221, Q278, and Q279 of SEQ ID NO: 4; an arginine at a position equivalent to position Q97 of SEQ ID NO: 4; and an alanine at positions equivalent to positions D70, D71, D131, D132, D189, D190, D247, D248, D305, and D306;
   wherein the ClfA antigen is conjugated to a *Staphylococcus aureus* serotype 8 capsular polysaccharide, and the Hla antigen is conjugated to a *S. aureus* serotype 5 capsular polysaccharide.

2. The immunogenic composition according to claim 1, wherein
   a. the amino acid sequence of part (a) is at least 96%, 97%, 98% or 99% identical to SEQ ID NO. 32;
   b. the amino acid sequence of part (b) is at least 96%, 97%, 98% or 99% identical to SEQ ID NO. 12; and/or
   c. the amino acid sequence of part (c) is at least 96%, 97%, 98% or 99% identical to SEQ ID NO. 27.

3. The immunogenic composition according to claim 2, wherein the ClfA antigen comprises or consists of the sequence of SEQ ID NO: 7 or SEQ ID NO: 32.

4. The immunogenic composition according to claim 2, wherein the Hla antigen comprises or consists of the sequence of SEQ ID NO: 11 or SEQ ID NO: 12.

5. The immunogenic composition according to claim 2, wherein the SpA antigen comprises or consists of the sequence of SEQ ID NO: 26 or SEQ ID NO: 27.

6. The immunogenic composition according to claim 2, wherein (i) the ClfA antigen comprises the amino acid sequence of SEQ ID NO: 7 or SEQ ID NO: 32; (ii) the Hla antigen comprises the amino acid sequence of SEQ ID NO: 11 or SEQ ID NO: 12; and (iii) the SpA antigen comprises the amino acid sequence of SEQ ID NO: 26 or SEQ ID NO: 27.

7. The immunogenic composition according to claim 1, wherein said ClfA-CP8 and Hla-CP5 conjugates are bioconjugates.

8. The immunogenic composition according to claim 2, further comprising an adjuvant.

9. A kit comprising (i) a first container comprising the immunogenic composition of claim 2; and (ii) a second container comprising an adjuvant.

10. The immunogenic composition of claim 8, wherein the adjuvant comprises a saponin and a Toll Like Receptor 4 (TLR4) agonist.

11. The immunogenic composition of claim 10, wherein the TLR4 agonist is a lipopolysaccharide.

12. The immunogenic composition of claim 11, wherein the lipopolysaccharide is 3-de-O-acylated monophosphoryl lipid A (3D-MPL).

13. The immunogenic composition of claim 10, wherein the saponin comprises an active fraction of the saponin derived from the bark of *Quillaja Saponaria Molina*.

14. The immunogenic composition of claim 13, wherein the active fraction of the saponin derived from the bark of *Quillaja Saponaria Molina* is QS21.

15. The immunogenic composition of claim 8, wherein the adjuvant comprises 3D-MPL and QS21 in a liposome.

16. The immunogenic composition of claim 8, wherein the adjuvant comprises a Toll Like Receptor 7 (TLR7) agonist adsorbed to aluminum hydroxide (AlOH).

* * * * *

SEQUENCE LISTING

<160> NUMBER OF SEQ ID NOS: 32

<210> SEQ ID NO 1
<211> LENGTH: 522
<212> TYPE: PRT
<213> ORGANISM: Staphylococcus aureus

<400> SEQUENCE: 1

```
Ala Ser Glu Asn Ser Val Thr Gln Ser Asp Ser Ala Ser Asn Glu Ser
1               5                   10                  15

Lys Ser Asn Asp Ser Ser Val Ser Ala Ala Pro Lys Thr Asp Asp
            20                  25                  30

Thr Asn Val Ser Asp Thr Lys Thr Ser Ser Asn Thr Asn Asn Gly Glu
        35                  40                  45

Thr Ser Val Ala Gln Asn Pro Ala Gln Gln Glu Thr Thr Gln Ser Ser
    50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Thr Gln Ser Ser
                85                  90                  95

Asn Thr Asn Ala Glu Glu Leu Val Asn Gln Thr Ser Asn Glu Thr Thr
            100                 105                 110

Phe Asn Asp Thr Asn Thr Val Ser Ser Val Asn Ser Pro Gln Asn Ser
        115                 120                 125

Thr Asn Ala Glu Asn Val Ser Thr Thr Gln Asp Thr Ser Thr Glu Ala
    130                 135                 140

Thr Pro Ser Asn Asn Glu Ser Ala Pro Gln Ser Thr Asp Ala Ser Asn
145                 150                 155                 160

Lys Asp Val Val Asn Gln Ala Val Asn Thr Ser Ala Pro Arg Met Arg
                165                 170                 175

Ala Phe Ser Leu Ala Ala Val Ala Ala Asp Ala Pro Ala Ala Gly Thr
            180                 185                 190

Asp Ile Thr Asn Gln Leu Thr Asn Val Thr Gly Ile Asp Ser Gly
        195                 200                 205

Thr Thr Val Tyr Pro His Gln Ala Gly Tyr Val Lys Leu Asn Tyr Gly
    210                 215                 220
```

```
Phe Ser Val Pro Asn Ser Ala Val Lys Gly Asp Thr Phe Lys Ile Thr
225                 230                 235                 240

Val Pro Lys Glu Leu Asn Leu Asn Gly Val Thr Ser Thr Ala Lys Val
            245                 250                 255

Pro Pro Ile Met Ala Gly Asp Gln Val Leu Ala Asn Gly Val Ile Asp
            260                 265                 270

Ser Asp Gly Asn Val Ile Tyr Thr Phe Thr Asp Tyr Val Asn Thr Lys
        275                 280                 285

Asp Asp Val Lys Ala Thr Leu Thr Met Pro Ala Tyr Ile Asp Pro Glu
        290                 295                 300

Asn Val Lys Lys Thr Gly Asn Val Thr Leu Ala Thr Gly Ile Gly Ser
305                 310                 315                 320

Thr Thr Ala Asn Lys Thr Val Leu Val Asp Tyr Glu Lys Tyr Gly Lys
            325                 330                 335

Phe Tyr Asn Leu Ser Ile Lys Gly Thr Ile Asp Gln Ile Asp Lys Thr
            340                 345                 350

Asn Asn Thr Tyr Arg Gln Thr Ile Tyr Val Asn Pro Ser Gly Asp Asn
        355                 360                 365

Val Ile Ala Pro Val Leu Thr Gly Asn Leu Lys Pro Asn Thr Asp Ser
370                 375                 380

Asn Ala Leu Ile Asp Gln Gln Asn Thr Ser Ile Lys Val Tyr Lys Val
385                 390                 395                 400

Asp Asn Ala Ala Asp Leu Ser Glu Ser Tyr Phe Val Asn Pro Glu Asn
            405                 410                 415

Phe Glu Asp Val Thr Asn Ser Val Asn Ile Thr Phe Pro Asn Pro Asn
            420                 425                 430

Gln Tyr Lys Val Glu Phe Asn Thr Pro Asp Asp Gln Ile Thr Thr Pro
        435                 440                 445

Tyr Ile Val Val Asn Gly His Ile Asp Pro Asn Ser Lys Gly Asp
450                 455                 460

Leu Ala Leu Arg Ser Thr Leu Tyr Gly Tyr Asn Ser Asn Ile Ile Trp
465                 470                 475                 480

Arg Ser Met Ser Trp Asp Asn Glu Val Ala Phe Asn Asn Gly Ser Gly
            485                 490                 495

Ser Gly Asp Gly Ile Asp Lys Pro Val Val Pro Glu Gln Pro Asp Glu
        500                 505                 510

Pro Gly Glu Ile Glu Pro Ile Pro Glu Asp
        515                 520

<210> SEQ ID NO 2
<211> LENGTH: 340
<212> TYPE: PRT
<213> ORGANISM: Staphylococcus aureus

<400> SEQUENCE: 2

Val Ala Ala Asp Ala Pro Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
```

```
                65                  70                  75                  80
        Asp Gln Val Leu Ala Asn Gly Val Ile Asp Ser Asp Gly Asn Val Ile
                            85                  90                  95

Tyr Thr Phe Thr Asp Tyr Val Asn Thr Lys Asp Val Lys Ala Thr
                        100                 105                 110

Leu Thr Met Pro Ala Tyr Ile Asp Pro Glu Asn Val Lys Lys Thr Gly
                        115                 120                 125

Asn Val Thr Leu Ala Thr Gly Ile Gly Ser Thr Thr Ala Asn Lys Thr
                    130                 135                 140

Val Leu Val Asp Tyr Glu Lys Tyr Gly Lys Phe Tyr Asn Leu Ser Ile
        145                 150                 155                 160

Lys Gly Thr Ile Asp Gln Ile Asp Lys Thr Asn Asn Thr Tyr Arg Gln
                        165                 170                 175

Thr Ile Tyr Val Asn Pro Ser Gly Asp Asn Val Ile Ala Pro Val Leu
                        180                 185                 190

Thr Gly Asn Leu Lys Pro Asn Thr Asp Ser Asn Ala Leu Ile Asp Gln
                    195                 200                 205

Gln Asn Thr Ser Ile Lys Val Tyr Lys Val Asp Asn Ala Ala Asp Leu
                210                 215                 220

Ser Glu Ser Tyr Phe Val Asn Pro Glu Asn Phe Glu Asp Val Thr Asn
        225                 230                 235                 240

Ser Val Asn Ile Thr Phe Pro Asn Pro Asn Gln Tyr Lys Val Glu Phe
                        245                 250                 255

Asn Thr Pro Asp Asp Gln Ile Thr Thr Pro Tyr Ile Val Val Asn
                    260                 265                 270

Gly His Ile Asp Pro Asn Ser Lys Gly Asp Leu Ala Leu Arg Ser Thr
                275                 280                 285

Leu Tyr Gly Tyr Asn Ser Asn Ile Ile Trp Arg Ser Met Ser Trp Asp
                    290                 295                 300

Asn Glu Val Ala Phe Asn Asn Gly Ser Gly Ser Gly Asp Gly Ile Asp
        305                 310                 315                 320

Lys Pro Val Val Pro Glu Gln Pro Asp Glu Pro Gly Glu Ile Glu Pro
                        325                 330                 335

Ile Pro Glu Asp
                    340

<210> SEQ ID NO 3
<211> LENGTH: 293
<212> TYPE: PRT
<213> ORGANISM: Staphylococcus aureus

<400> SEQUENCE: 3

Ala Asp Ser Asp Ile Asn Ile Lys Thr Gly Thr Thr Asp Ile Gly Ser
        1               5                   10                  15

Asn Thr Thr Val Lys Thr Gly Asp Leu Val Thr Tyr Asp Lys Glu Asn
                        20                  25                  30

Gly Met His Lys Lys Val Phe Tyr Ser Phe Ile Asp Asp Lys Asn His
                    35                  40                  45

Asn Lys Lys Leu Leu Val Ile Arg Thr Lys Gly Thr Ile Ala Gly Gln
                50                  55                  60

Tyr Arg Val Tyr Ser Glu Glu Gly Ala Asn Lys Ser Gly Leu Ala Trp
        65                  70                  75                  80

Pro Ser Ala Phe Lys Val Gln Leu Gln Leu Pro Asp Asn Glu Val Ala
                        85                  90                  95
```

```
Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
        290

<210> SEQ ID NO 4
<211> LENGTH: 516
<212> TYPE: PRT
<213> ORGANISM: Staphylococcus aureus

<400> SEQUENCE: 4

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175
```

```
Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
        355                 360                 365

Glu Asp Gly Asn Lys Pro Gly Lys Glu Asp Asn Lys Pro Gly Lys
    370                 375                 380

Glu Asp Gly Asn Lys Pro Gly Lys Glu Asp Asn Lys Lys Pro Gly Lys
385                 390                 395                 400

Glu Asp Gly Asn Lys Pro Gly Lys Glu Asp Gly Asn Lys Pro Gly Lys
                405                 410                 415

Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
        435                 440                 445

Asn Lys Leu Ala Asp Lys Asn Met Ile Lys Pro Gly Gln Glu Leu Val
    450                 455                 460

Val Asp Lys Lys Gln Pro Ala Asn His Ala Asp Ala Asn Lys Ala Gln
465                 470                 475                 480

Ala Leu Pro Glu Thr Gly Glu Glu Asn Pro Phe Ile Gly Thr Thr Val
                485                 490                 495

Phe Gly Gly Leu Ser Leu Ala Leu Gly Ala Ala Leu Leu Ala Gly Arg
            500                 505                 510

Arg Arg Glu Leu
        515

<210> SEQ ID NO 5
<211> LENGTH: 340
<212> TYPE: PRT
<213> ORGANISM: Artificial Sequence
<220> FEATURE:
<223> OTHER INFORMATION: ClfA N2N3 P116S/Y118A

<400> SEQUENCE: 5

Val Ala Ala Asp Ala Pro Ala Ala Gly Thr Asp Ile Thr Asn Gln Leu
1               5                   10                  15
```

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

Leu Thr Met Ser Ala Ala Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Gly Ser Gly Ser Asp Gly Ile Asp
305                 310                 315                 320

Lys Pro Val Val Pro Glu Gln Pro Asp Glu Pro Gly Glu Ile Glu Pro
                325                 330                 335

Ile Pro Glu Asp
            340

<210> SEQ ID NO 6
<211> LENGTH: 346
<212> TYPE: PRT
<213> ORGANISM: Artificial Sequence
<220> FEATURE:
<223> OTHER INFORMATION: ClfA N2N3 P116S/Y118A with PglB

<400> SEQUENCE: 6

Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
            35                  40                  45

Ala Val Lys Gly Asp Thr Phe Lys Ile Thr Val Pro Lys Glu Leu Asn
 50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

Leu Thr Met Ser Ala Ala Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Asn Gly Ser Gly Ser Gly Asp Gly Ile Asp
305                 310                 315                 320

Lys Pro Val Val Pro Glu Gln Pro Asp Glu Pro Gly Glu Ile Glu Pro
                325                 330                 335

Lys Asp Gln Asn Ala Thr Lys Pro Glu Asp
            340                 345

<210> SEQ ID NO 7
<211> LENGTH: 347
<212> TYPE: PRT
<213> ORGANISM: Artificial Sequence
<220> FEATURE:
<223> OTHER INFORMATION: ClfA N2N3 P116S/Y118A

<400> SEQUENCE: 7

Ser Val Ala Ala Asp Ala Pro Ala Ala Gly Thr Asp Ile Thr Asn Gln
1               5                   10                  15

Leu Thr Asn Val Thr Val Gly Ile Asp Ser Gly Thr Thr Val Tyr Pro
            20                  25                  30

His Gln Ala Gly Tyr Val Lys Leu Asn Tyr Gly Phe Ser Val Pro Asn
        35                  40                  45

-continued

```
Ser Ala Val Lys Gly Asp Thr Phe Lys Ile Thr Val Pro Lys Glu Leu
 50                  55                  60

Asn Leu Asn Gly Val Thr Ser Thr Ala Lys Val Pro Pro Ile Met Ala
 65                  70                  75                  80

Gly Asp Gln Val Leu Ala Asn Gly Val Ile Asp Ser Asp Gly Asn Val
                 85                  90                  95

Ile Tyr Thr Phe Thr Asp Tyr Val Asn Thr Lys Asp Asp Val Lys Ala
            100                 105                 110

Thr Leu Thr Met Ser Ala Ala Ile Asp Pro Glu Asn Val Lys Lys Thr
        115                 120                 125

Gly Asn Val Thr Leu Ala Thr Gly Ile Gly Ser Thr Thr Ala Asn Lys
    130                 135                 140

Thr Val Leu Val Asp Tyr Glu Lys Tyr Gly Lys Phe Tyr Asn Leu Ser
145                 150                 155                 160

Ile Lys Gly Thr Ile Asp Gln Ile Asp Lys Thr Asn Asn Thr Tyr Arg
                165                 170                 175

Gln Thr Ile Tyr Val Asn Pro Ser Gly Asp Asn Val Ile Ala Pro Val
            180                 185                 190

Leu Thr Gly Asn Leu Lys Pro Asn Thr Asp Ser Asn Ala Leu Ile Asp
        195                 200                 205

Gln Gln Asn Thr Ser Ile Lys Val Tyr Lys Val Asp Asn Ala Ala Asp
    210                 215                 220

Leu Ser Glu Ser Tyr Phe Val Asn Pro Glu Asn Phe Glu Asp Val Thr
225                 230                 235                 240

Asn Ser Val Asn Ile Thr Phe Pro Asn Pro Asn Gln Tyr Lys Val Glu
                245                 250                 255

Phe Asn Thr Pro Asp Asp Gln Ile Thr Thr Pro Tyr Ile Val Val Val
            260                 265                 270

Asn Gly His Ile Asp Pro Asn Ser Lys Gly Asp Leu Ala Leu Arg Ser
        275                 280                 285

Thr Leu Tyr Gly Tyr Asn Ser Asn Ile Ile Trp Arg Ser Met Ser Trp
    290                 295                 300

Asp Asn Glu Val Ala Phe Asn Asn Gly Ser Gly Ser Gly Asp Gly Ile
305                 310                 315                 320

Asp Lys Pro Val Val Pro Glu Gln Pro Asp Glu Pro Gly Glu Ile Glu
                325                 330                 335

Pro Lys Asp Gln Asn Ala Thr Lys Pro Glu Asp
            340                 345

<210> SEQ ID NO 8
<211> LENGTH: 293
<212> TYPE: PRT
<213> ORGANISM: Artificial Sequence
<220> FEATURE:
<223> OTHER INFORMATION: Mature Hla H35L

<400> SEQUENCE: 8

Ala Asp Ser Asp Ile Asn Ile Lys Thr Gly Thr Thr Asp Ile Gly Ser
 1               5                  10                  15

Asn Thr Thr Val Lys Thr Gly Asp Leu Val Thr Tyr Asp Lys Glu Asn
                 20                  25                  30

Gly Met Leu Lys Lys Val Phe Tyr Ser Phe Ile Asp Asp Lys Asn His
             35                  40                  45

Asn Lys Lys Leu Leu Val Ile Arg Thr Lys Gly Thr Ile Ala Gly Gln
 50                  55                  60
```

```
Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290
```

<210> SEQ ID NO 9
<211> LENGTH: 299
<212> TYPE: PRT
<213> ORGANISM: Artificial Sequence
<220> FEATURE:
<223> OTHER INFORMATION: Mature Hla H35L with PglB consensus sequence
      substituted for residue K131

<400> SEQUENCE: 9

```
Ala Asp Ser Asp Ile Asn Ile Lys Thr Gly Thr Thr Asp Ile Gly Ser
  1               5                  10                  15

Asn Thr Thr Val Lys Thr Gly Asp Leu Val Thr Tyr Asp Lys Glu Asn
                 20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
```

```
            115                 120                 125
Thr Gly Lys Asp Gln Asn Arg Thr Lys Ile Gly Gly Leu Ile Gly Ala
    130                 135                 140
Asn Val Ser Ile Gly His Thr Leu Lys Tyr Val Gln Pro Asp Phe Lys
145                 150                 155                 160
Thr Ile Leu Glu Ser Pro Thr Asp Lys Lys Val Gly Trp Lys Val Ile
                165                 170                 175
Phe Asn Asn Met Val Asn Gln Asn Trp Gly Pro Tyr Asp Arg Asp Ser
            180                 185                 190
Trp Asn Pro Val Tyr Gly Asn Gln Leu Phe Met Lys Thr Arg Asn Gly
                195                 200                 205
Ser Met Lys Ala Ala Asp Asn Phe Leu Asp Pro Asn Lys Ala Ser Ser
    210                 215                 220
Leu Leu Ser Ser Gly Phe Ser Pro Asp Phe Ala Thr Val Ile Thr Met
225                 230                 235                 240
Asp Arg Lys Ala Ser Lys Gln Gln Thr Asn Ile Asp Val Ile Tyr Glu
                245                 250                 255
Arg Val Arg Asp Asp Tyr Gln Leu His Trp Thr Ser Thr Asn Trp Lys
            260                 265                 270
Gly Thr Asn Thr Lys Asp Lys Trp Ile Asp Arg Ser Ser Glu Arg Tyr
                275                 280                 285
Lys Ile Asp Trp Glu Lys Glu Glu Met Thr Asn
            290                 295

<210> SEQ ID NO 10
<211> LENGTH: 293
<212> TYPE: PRT
<213> ORGANISM: Artificial Sequence
<220> FEATURE:
<223> OTHER INFORMATION: Mature Hla H35L/H48C/G122C

<400> SEQUENCE: 10

Ala Asp Ser Asp Ile Asn Ile Lys Thr Gly Thr Thr Asp Ile Gly Ser
1               5                   10                  15
Asn Thr Thr Val Lys Thr Gly Asp Leu Val Thr Tyr Asp Lys Glu Asn
            20                  25                  30
Gly Met Leu Lys Lys Val Phe Tyr Ser Phe Ile Asp Asp Lys Asn Cys
        35                  40                  45
Asn Lys Lys Leu Leu Val Ile Arg Thr Lys Gly Thr Ile Ala Gly Gln
    50                  55                  60
Tyr Arg Val Tyr Ser Glu Glu Gly Ala Asn Lys Ser Gly Leu Ala Trp
65                  70                  75                  80
Pro Ser Ala Phe Lys Val Gln Leu Gln Leu Pro Asp Asn Glu Val Ala
                85                  90                  95
Gln Ile Ser Asp Tyr Tyr Pro Arg Asn Ser Ile Asp Thr Lys Glu Tyr
            100                 105                 110
Met Ser Thr Leu Thr Tyr Gly Phe Asn Cys Asn Val Thr Gly Asp Asp
        115                 120                 125
Thr Gly Lys Ile Gly Gly Leu Ile Gly Ala Asn Val Ser Ile Gly His
    130                 135                 140
Thr Leu Lys Tyr Val Gln Pro Asp Phe Lys Thr Ile Leu Glu Ser Pro
145                 150                 155                 160
Thr Asp Lys Lys Val Gly Trp Lys Val Ile Phe Asn Asn Met Val Asn
                165                 170                 175
Gln Asn Trp Gly Pro Tyr Asp Arg Asp Ser Trp Asn Pro Val Tyr Gly
```

```
            180                 185                 190
Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
            275                 280                 285

Glu Glu Met Thr Asn
            290

<210> SEQ ID NO 11
<211> LENGTH: 299
<212> TYPE: PRT
<213> ORGANISM: Artificial Sequence
<220> FEATURE:
<223> OTHER INFORMATION: Mature Hla H35L/H48C/G122C with PglB consensus
      sequence substituted for residue K131

<400> SEQUENCE: 11

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn Cys
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Cys Asn Val Thr Gly Asp Asp
            115                 120                 125

Thr Gly Lys Asp Gln Asn Arg Thr Lys Ile Gly Gly Leu Ile Gly Ala
            130                 135                 140

Asn Val Ser Ile Gly His Thr Leu Lys Tyr Val Gln Pro Asp Phe Lys
145                 150                 155                 160

Thr Ile Leu Glu Ser Pro Thr Asp Lys Lys Val Gly Trp Lys Val Ile
            165                 170                 175

Phe Asn Asn Met Val Asn Gln Asn Trp Gly Pro Tyr Asp Arg Asp Ser
            180                 185                 190

Trp Asn Pro Val Tyr Gly Asn Gln Leu Phe Met Lys Thr Arg Asn Gly
            195                 200                 205

Ser Met Lys Ala Ala Asp Asn Phe Leu Asp Pro Asn Lys Ala Ser Ser
            210                 215                 220

Leu Leu Ser Ser Gly Phe Ser Pro Asp Phe Ala Thr Val Ile Thr Met
225                 230                 235                 240
```

```
Asp Arg Lys Ala Ser Lys Gln Gln Thr Asn Ile Asp Val Ile Tyr Glu
            245                 250                 255
Arg Val Arg Asp Asp Tyr Gln Leu His Trp Thr Ser Thr Asn Trp Lys
        260                 265                 270
Gly Thr Asn Thr Lys Asp Lys Trp Ile Asp Arg Ser Ser Glu Arg Tyr
    275                 280                 285
Lys Ile Asp Trp Glu Lys Glu Glu Met Thr Asn
290                 295
```

<210> SEQ ID NO 12
<211> LENGTH: 306
<212> TYPE: PRT
<213> ORGANISM: Artificial Sequence
<220> FEATURE:
<223> OTHER INFORMATION: Hla H35L/H48C/G122C with N-terminal S,
      C-terminal GSHRHR, and KDQNRTK substituted for residue K131

<400> SEQUENCE: 12

```
Ser Ala Asp Ser Asp Ile Asn Ile Lys Thr Gly Thr Thr Asp Ile Gly
1               5                   10                  15
Ser Asn Thr Thr Val Lys Thr Gly Asp Leu Val Thr Tyr Asp Lys Glu
            20                  25                  30
Asn Gly Met Leu Lys Lys Val Phe Tyr Ser Phe Ile Asp Asp Lys Asn
        35                  40                  45
Cys Asn Lys Lys Leu Leu Val Ile Arg Thr Lys Gly Thr Ile Ala Gly
    50                  55                  60
Gln Tyr Arg Val Tyr Ser Glu Glu Gly Ala Asn Lys Ser Gly Leu Ala
65                  70                  75                  80
Trp Pro Ser Ala Phe Lys Val Gln Leu Gln Leu Pro Asp Asn Glu Val
                85                  90                  95
Ala Gln Ile Ser Asp Tyr Tyr Pro Arg Asn Ser Ile Asp Thr Lys Glu
            100                 105                 110
Tyr Met Ser Thr Leu Thr Tyr Gly Phe Asn Cys Asn Val Thr Gly Asp
        115                 120                 125
Asp Thr Gly Lys Asp Gln Asn Arg Thr Lys Ile Gly Gly Leu Ile Gly
    130                 135                 140
Ala Asn Val Ser Ile Gly His Thr Leu Lys Tyr Val Gln Pro Asp Phe
145                 150                 155                 160
Lys Thr Ile Leu Glu Ser Pro Thr Asp Lys Lys Val Gly Trp Lys Val
                165                 170                 175
Ile Phe Asn Asn Met Val Asn Gln Asn Trp Gly Pro Tyr Asp Arg Asp
            180                 185                 190
Ser Trp Asn Pro Val Tyr Gly Asn Gln Leu Phe Met Lys Thr Arg Asn
        195                 200                 205
Gly Ser Met Lys Ala Ala Asp Asn Phe Leu Asp Pro Asn Lys Ala Ser
    210                 215                 220
Ser Leu Leu Ser Ser Gly Phe Ser Pro Asp Phe Ala Thr Val Ile Thr
225                 230                 235                 240
Met Asp Arg Lys Ala Ser Lys Gln Gln Thr Asn Ile Asp Val Ile Tyr
                245                 250                 255
Glu Arg Val Arg Asp Asp Tyr Gln Leu His Trp Thr Ser Thr Asn Trp
            260                 265                 270
Lys Gly Thr Asn Thr Lys Asp Lys Trp Ile Asp Arg Ser Ser Glu Arg
        275                 280                 285
Tyr Lys Ile Asp Trp Glu Lys Glu Glu Met Thr Asn Gly Ser His Arg
    290                 295                 300
```

His Arg
305

<210> SEQ ID NO 13
<211> LENGTH: 291
<212> TYPE: PRT
<213> ORGANISM: Staphylococcus aureus

<400> SEQUENCE: 13

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Gln Gln Ser Ala Phe Tyr Glu Ile Leu Asn Met Pro Asn
65                  70                  75                  80

Leu Asn Glu Ala Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 14
<211> LENGTH: 56
<212> TYPE: PRT
<213> ORGANISM: Staphylococcus aureus

<400> SEQUENCE: 14

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
            35                  40                  45

Leu Asn Asp Ser Gln Ala Pro Lys
    50                  55

<210> SEQ ID NO 15
<211> LENGTH: 61
<212> TYPE: PRT
<213> ORGANISM: Staphylococcus aureus

<400> SEQUENCE: 15

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
            35                  40                  45

Gly Glu Ala Lys Lys Leu Asn Glu Ser Gln Ala Pro Lys
    50                  55                  60

<210> SEQ ID NO 16
<211> LENGTH: 58
<212> TYPE: PRT
<213> ORGANISM: Staphylococcus aureus

<400> SEQUENCE: 16

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
            35                  40                  45

Lys Lys Leu Asn Glu Ser Gln Ala Pro Lys
    50                  55

<210> SEQ ID NO 17
<211> LENGTH: 58
<212> TYPE: PRT
<213> ORGANISM: Staphylococcus aureus

<400> SEQUENCE: 17

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
            35                  40                  45

Lys Lys Leu Asn Glu Ser Gln Ala Pro Lys
    50                  55

<210> SEQ ID NO 18
<211> LENGTH: 58
<212> TYPE: PRT
<213> ORGANISM: Staphylococcus aureus

<400> SEQUENCE: 18

Ala Asp Asn Lys Phe Asn Lys Glu Gln Gln Asn Ala Phe Tyr Glu Ile

```
1               5                   10                  15
Leu His Leu Pro Asn Leu Thr Glu Glu Gln Arg Asn Gly Phe Ile Gln
        20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys
        50                  55

<210> SEQ ID NO 19
<211> LENGTH: 56
<212> TYPE: PRT
<213> ORGANISM: Artificial Sequence
<220> FEATURE:
<223> OTHER INFORMATION: SpA E domain with QQ-KK substitutions at
      positions 7 and 8 and DD-AA substitutions at positions 34 and 35

<400> SEQUENCE: 19

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys
        50                  55

<210> SEQ ID NO 20
<211> LENGTH: 61
<212> TYPE: PRT
<213> ORGANISM: Artificial Sequence
<220> FEATURE:
<223> OTHER INFORMATION: SpA D domain with QQ-KK substitutions at
      positions 12 and 13 and DD-AA substitutions at positions 39 and 40

<400> SEQUENCE: 20

Ala Asp Ala Gln Gln Asn Asn Phe Asn Lys Asp Lys Lys Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Ala Ala Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 21
<211> LENGTH: 58
<212> TYPE: PRT
<213> ORGANISM: Artificial Sequence
<220> FEATURE:
<223> OTHER INFORMATION: SpA A domain with QQ-KK substitutions at
      positions 9 and 108 and DD-AA substitutions at positions 36 and 37

<400> SEQUENCE: 21

Ala Asp Asn Asn Phe Asn Lys Glu Lys Lys Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Ala Ala Pro Ser Gln Ser Ala Asn Leu Leu Ser Glu Ala
        35                  40                  45

Lys Lys Leu Asn Glu Ser Gln Ala Pro Lys
        50                  55
```

<210> SEQ ID NO 22
<211> LENGTH: 58
<212> TYPE: PRT
<213> ORGANISM: Artificial Sequence
<220> FEATURE:
<223> OTHER INFORMATION: SpA B domain with QQ-KK substitutions at
      positions 9 and 10 and DD-AA substitutions at positions 36 and 37

<400> SEQUENCE: 22

Ala Asp Asn Lys Phe Asn Lys Glu Lys Lys Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Ala Ala Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 23
<211> LENGTH: 58
<212> TYPE: PRT
<213> ORGANISM: Artificial Sequence
<220> FEATURE:
<223> OTHER INFORMATION: SpA C domain with QQ-KK substitutions at
      positions 9 and 10 and DD-AA substitutions at positions 36 and 37

<400> SEQUENCE: 23

Ala Asp Asn Lys Phe Asn Lys Glu Lys Lys Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Ala Ala Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 24
<211> LENGTH: 61
<212> TYPE: PRT
<213> ORGANISM: Artificial Sequence
<220> FEATURE:
<223> OTHER INFORMATION: SpA D domain with QQ-KR substitutions at
      positions 4 and 5, QQ-KK substitutions at positions 12 and 13 and
      DD-AA substitutions at positions 39 and 40

<400> SEQUENCE: 24

Ala Asp Ala Lys Arg Asn Asn Phe Asn Lys Asp Lys Lys Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Ala Ala Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 25
<211> LENGTH: 61
<212> TYPE: PRT
<213> ORGANISM: Artificial Sequence
<220> FEATURE:
<223> OTHER INFORMATION: SpA D domain with QQ-KR substitutions at
      positions 4 and 5

<400> SEQUENCE: 25

```
Ala Asp Ala Lys Arg Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
50                  55                  60
```

<210> SEQ ID NO 26
<211> LENGTH: 291
<212> TYPE: PRT
<213> ORGANISM: Artificial Sequence
<220> FEATURE:
<223> OTHER INFORMATION: SpA IgG binding portion with the substitutions
      of SEQ ID NOs 19-23

<400> SEQUENCE: 26

```
Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285
```

```
Ala Pro Lys
    290

<210> SEQ ID NO 27
<211> LENGTH: 291
<212> TYPE: PRT
<213> ORGANISM: Artificial Sequence
<220> FEATURE:
<223> OTHER INFORMATION: SpA IgG binding portion with the substitutions
      of SEQ ID NOs 19 and 21 24

<400> SEQUENCE: 27

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 28
<211> LENGTH: 5
<212> TYPE: PRT
<213> ORGANISM: Artificial Sequence
<220> FEATURE:
<223> OTHER INFORMATION: PglB consensus sequence
```

```
<220> FEATURE:
<221> NAME/KEY: MISC_FEATURE
<222> LOCATION: (1)..(1)
<223> OTHER INFORMATION: Xaa = Asp or Glu
<220> FEATURE:
<221> NAME/KEY: MISC_FEATURE
<222> LOCATION: (2)..(2)
<223> OTHER INFORMATION: Xaa can be any naturally occurring amino acid
      except proline
<220> FEATURE:
<221> NAME/KEY: MISC_FEATURE
<222> LOCATION: (4)..(4)
<223> OTHER INFORMATION: Xaa can be any naturally occurring amino acid
      except proline
<220> FEATURE:
<221> NAME/KEY: MISC_FEATURE
<222> LOCATION: (5)..(5)
<223> OTHER INFORMATION: Xaa = Ser or Thr

<400> SEQUENCE: 28

Xaa Xaa Asn Xaa Xaa
1               5

<210> SEQ ID NO 29
<211> LENGTH: 7
<212> TYPE: PRT
<213> ORGANISM: Artificial Sequence
<220> FEATURE:
<223> OTHER INFORMATION: PglB consensus sequence
<220> FEATURE:
<221> NAME/KEY: MISC_FEATURE
<222> LOCATION: (2)..(2)
<223> OTHER INFORMATION: Xaa = Asp or Glu
<220> FEATURE:
<221> NAME/KEY: MISC_FEATURE
<222> LOCATION: (3)..(3)
<223> OTHER INFORMATION: Xaa can be any naturally occurring amino acid
      except proline
<220> FEATURE:
<221> NAME/KEY: MISC_FEATURE
<222> LOCATION: (5)..(5)
<223> OTHER INFORMATION: Xaa can be any naturally occurring amino acid
      except proline
<220> FEATURE:
<221> NAME/KEY: MISC_FEATURE
<222> LOCATION: (6)..(6)
<223> OTHER INFORMATION: Xaa = Ser or Thr

<400> SEQUENCE: 29

Lys Xaa Xaa Asn Xaa Xaa Lys
1               5

<210> SEQ ID NO 30
<211> LENGTH: 7
<212> TYPE: PRT
<213> ORGANISM: Artificial Sequence
<220> FEATURE:
<223> OTHER INFORMATION: PglB consensus sequence

<400> SEQUENCE: 30

Lys Asp Gln Asn Arg Thr Lys
1               5

<210> SEQ ID NO 31
<211> LENGTH: 7
<212> TYPE: PRT
<213> ORGANISM: Artificial Sequence
<220> FEATURE:
<223> OTHER INFORMATION: PglB consensus sequence

<400> SEQUENCE: 31

Lys Asp Gln Asn Ala Thr Lys
```

<210> SEQ ID NO 32
<211> LENGTH: 349
<212> TYPE: PRT
<213> ORGANISM: Artificial Sequence
<220> FEATURE:
<223> OTHER INFORMATION: ClfAN2N3P116S/Y118A at I337, N-terminal S,
      C-terminal GS

<400> SEQUENCE: 32

```
Ser Val Ala Ala Asp Ala Pro Ala Ala Gly Thr Asp Ile Thr Asn Gln
1               5                   10                  15

Leu Thr Asn Val Thr Val Gly Ile Asp Ser Gly Thr Thr Val Tyr Pro
            20                  25                  30

His Gln Ala Gly Tyr Val Lys Leu Asn Tyr Gly Phe Ser Val Pro Asn
        35                  40                  45

Ser Ala Val Lys Gly Asp Thr Phe Lys Ile Thr Val Pro Lys Glu Leu
    50                  55                  60

Asn Leu Asn Gly Val Thr Ser Thr Ala Lys Val Pro Pro Ile Met Ala
65                  70                  75                  80

Gly Asp Gln Val Leu Ala Asn Gly Val Ile Asp Ser Asp Gly Asn Val
                85                  90                  95

Ile Tyr Thr Phe Thr Asp Tyr Val Asn Thr Lys Asp Asp Val Lys Ala
            100                 105                 110

Thr Leu Thr Met Ser Ala Ala Ile Asp Pro Glu Asn Val Lys Lys Thr
        115                 120                 125

Gly Asn Val Thr Leu Ala Thr Gly Ile Gly Ser Thr Thr Ala Asn Lys
    130                 135                 140

Thr Val Leu Val Asp Tyr Glu Lys Tyr Gly Lys Phe Tyr Asn Leu Ser
145                 150                 155                 160

Ile Lys Gly Thr Ile Asp Gln Ile Asp Lys Thr Asn Asn Thr Tyr Arg
                165                 170                 175

Gln Thr Ile Tyr Val Asn Pro Ser Gly Asp Asn Val Ile Ala Pro Val
            180                 185                 190

Leu Thr Gly Asn Leu Lys Pro Asn Thr Asp Ser Asn Ala Leu Ile Asp
        195                 200                 205

Gln Gln Asn Thr Ser Ile Lys Val Tyr Lys Val Asp Asn Ala Ala Asp
    210                 215                 220

Leu Ser Glu Ser Tyr Phe Val Asn Pro Glu Asn Phe Glu Asp Val Thr
225                 230                 235                 240

Asn Ser Val Asn Ile Thr Phe Pro Asn Pro Asn Gln Tyr Lys Val Glu
                245                 250                 255

Phe Asn Thr Pro Asp Asp Gln Ile Thr Thr Pro Tyr Ile Val Val Val
            260                 265                 270

Asn Gly His Ile Asp Pro Asn Ser Lys Gly Asp Leu Ala Leu Arg Ser
        275                 280                 285

Thr Leu Tyr Gly Tyr Asn Ser Asn Ile Ile Trp Arg Ser Met Ser Trp
    290                 295                 300

Asp Asn Glu Val Ala Phe Asn Asn Gly Ser Gly Ser Gly Asp Gly Ile
305                 310                 315                 320

Asp Lys Pro Val Val Pro Glu Gln Pro Asp Glu Pro Gly Glu Ile Glu
                325                 330                 335

Pro Lys Asp Gln Asn Ala Thr Lys Pro Glu Asp Gly Ser
            340                 345
```